US012274581B2

(12) United States Patent
Cox et al.

(10) Patent No.: US 12,274,581 B2
(45) Date of Patent: Apr. 15, 2025

(54) ULTRASOUND IMAGING SYSTEM HAVING AUTOMATIC IMAGE PRESENTATION

(71) Applicant: C. R. Bard, Inc., Franklin Lakes, NJ (US)

(72) Inventors: Jeremy B. Cox, Salt Lake City, UT (US); Michael A. Randall, Gilbert, AZ (US); Peng Zheng, Chandler, AZ (US); Samuel J. Radochonski, San Francisco, CA (US); Dean M. Addison, Victoria (CA); Bryan A. Matthews, Saanichton (CA); Jeffery L. Addison, Victoria (CA)

(73) Assignee: C. R. Bard, Inc., Franklin Lakes, NJ (US)

( * ) Notice: Subject to any disclaimer, the term of this patent is extended or adjusted under 35 U.S.C. 154(b) by 77 days.

(21) Appl. No.: 18/323,130

(22) Filed: May 24, 2023

(65) Prior Publication Data
US 2023/0293153 A1 Sep. 21, 2023

Related U.S. Application Data

(60) Division of application No. 16/842,930, filed on Apr. 8, 2020, now Pat. No. 11,696,746, which is a division
(Continued)

(51) Int. Cl.
*A61B 8/08* (2006.01)
*A61B 8/00* (2006.01)
*G06T 7/215* (2017.01)

(52) U.S. Cl.
CPC ............ *A61B 8/483* (2013.01); *A61B 8/0841* (2013.01); *A61B 8/0891* (2013.01);
(Continued)

(58) Field of Classification Search
CPC ... A61B 8/0841; A61B 8/0891; A61B 8/4254; A61B 8/4263; A61B 8/4405;
(Continued)

(56) References Cited

U.S. PATENT DOCUMENTS

| 3,927,661 A | 12/1975 | Takemura |
| 4,362,059 A | 12/1982 | Zwyssig |

(Continued)

FOREIGN PATENT DOCUMENTS

| WO | 2010073165 A1 | 7/2010 |
| WO | 2012066470 A1 | 5/2012 |

(Continued)

OTHER PUBLICATIONS

R.B. Peterson, J. Hutchins "The iE33 intelligient echocardiographysystem", MEDICAMUNDI, Nov. 1, 2004 (Nov. 1, 2004), XP002741613, Retrieved from the Internet: http://www.healthcare.philips.com/pwc_hc/main/about/assets/Docs/medicamundi/mm_vol148_no3/11_Petrson.pdf, retrieved on Jun. 30, 2015.
(Continued)

*Primary Examiner* — Michael T Rozanski
(74) *Attorney, Agent, or Firm* — Dinsmore & Shohl LLP

(57) ABSTRACT

An ultrasound imaging system includes an interventional medical device having a first tracking element that generates tip location data based on a locator field. An ultrasound probe has an ultrasound transducer mechanism and a second tracking element. The ultrasound transducer mechanism has an active ultrasound transducer array that generates two-dimensional ultrasound slice data at any of a plurality of discrete imaging locations within a three-dimensional imaging volume. The second tracking element generates probe location data based on the locator field. A processor circuit is configured to execute program instructions to generate an ultrasound image for display, and is configured to generate
(Continued)

a positioning signal based on the tip location data and the probe location data to dynamically position the active ultrasound transducer array so that the two-dimensional ultrasound slice data includes the distal tip of the interventional medical device.

5 Claims, 25 Drawing Sheets

Related U.S. Application Data of application No. 15/525,319, filed as application No. PCT/US2015/060704 on Nov. 13, 2015, now Pat. No. 10,646,201, which is a continuation-in-part of application No. PCT/US2015/018068, filed on Feb. 27, 2015.

(60) Provisional application No. 62/081,530, filed on Nov. 18, 2014, provisional application No. 62/081,275, filed on Nov. 18, 2014.

(52) U.S. Cl.
CPC .......... *A61B 8/4254* (2013.01); *A61B 8/4263* (2013.01); *A61B 8/466* (2013.01); *A61B 8/488* (2013.01); *A61B 8/52* (2013.01); *G06T 7/215* (2017.01); *A61B 8/4405* (2013.01); *G06T 2207/10136* (2013.01); *G06T 2207/30104* (2013.01)

(58) Field of Classification Search
CPC ......... A61B 8/466; A61B 8/483; A61B 8/488; A61B 8/52; G06T 2207/10136; G06T 2207/30104; G06T 7/215
See application file for complete search history.

(56) References Cited

U.S. PATENT DOCUMENTS

| | | |
|---|---|---|
| 4,431,007 A | 2/1984 | Amazeen et al. |
| 4,483,344 A | 11/1984 | Atkov et al. |
| 4,669,482 A | 6/1987 | Ophir |
| 4,796,632 A | 1/1989 | Boyd et al. |
| 4,821,731 A | 4/1989 | Martinelli et al. |
| 4,831,601 A | 5/1989 | Breimesser et al. |
| 4,920,966 A | 5/1990 | Hon et al. |
| 4,974,593 A | 12/1990 | Ng |
| 5,094,243 A | 3/1992 | Puy et al. |
| 5,152,294 A | 10/1992 | Mochizuki et al. |
| 5,191,889 A | 3/1993 | Mornhinweg et al. |
| 5,335,663 A | 8/1994 | Oakley et al. |
| 5,381,794 A | 1/1995 | Tei et al. |
| 5,460,179 A | 10/1995 | Okunuki et al. |
| 5,503,152 A | 4/1996 | Oakley et al. |
| 5,598,845 A | 2/1997 | Chandraratna et al. |
| 5,615,680 A | 4/1997 | Sano |
| 5,626,554 A | 5/1997 | Ryaby et al. |
| 5,669,385 A | 9/1997 | Pesque et al. |
| 5,701,897 A | 12/1997 | Sano |
| 5,715,825 A | 2/1998 | Crowley |
| 5,727,553 A | 3/1998 | Saad |
| 5,769,843 A | 6/1998 | Abela et al. |
| 5,860,929 A | 1/1999 | Rubin et al. |
| 6,048,323 A | 4/2000 | Hon |
| 6,080,108 A | 6/2000 | Dunham |
| 6,132,376 A | 10/2000 | Hossack et al. |
| 6,132,378 A | 10/2000 | Marino |
| 6,241,667 B1 | 6/2001 | Vetter et al. |
| 6,241,675 B1 | 6/2001 | Oxaal et al. |
| 6,248,074 B1 | 6/2001 | Ohno et al. |
| 6,261,231 B1 | 7/2001 | Damphousse et al. |
| 6,263,093 B1 | 7/2001 | Mochizuki |
| 6,413,218 B1 | 7/2002 | Allison et al. |
| 6,423,006 B1 | 7/2002 | Banjanin |
| 6,464,642 B1 | 10/2002 | Kawagishi |
| 6,517,481 B2 | 2/2003 | Hoek et al. |
| 6,524,303 B1 | 2/2003 | Garibaldi |
| 6,527,718 B1 | 3/2003 | Connor et al. |
| 6,565,513 B1 | 5/2003 | Phillips |
| 6,587,709 B2 | 7/2003 | Solf et al. |
| 6,600,948 B2 | 7/2003 | Ben-Haim et al. |
| 6,684,094 B1 | 1/2004 | Lehr et al. |
| 6,685,644 B2 | 2/2004 | Seo et al. |
| 6,690,963 B2 | 2/2004 | Ben-Haim et al. |
| 6,716,166 B2 | 4/2004 | Govari |
| 6,735,465 B2 | 5/2004 | Panescu |
| 6,755,789 B2 | 6/2004 | Stringer et al. |
| 6,757,557 B1 | 6/2004 | Bladen et al. |
| 6,772,001 B2 | 8/2004 | Maschke |
| 6,773,402 B2 | 8/2004 | Govari et al. |
| 6,884,216 B2 | 4/2005 | Abe et al. |
| 6,895,267 B2 | 5/2005 | Panescu et al. |
| 6,951,543 B2 | 10/2005 | Roundhill |
| 6,970,733 B2 | 11/2005 | Willis et al. |
| 6,988,991 B2 | 1/2006 | Kim et al. |
| 7,010,338 B2 | 3/2006 | Ritter et al. |
| 7,051,738 B2 | 5/2006 | Oron et al. |
| 7,081,093 B2 | 7/2006 | Flesch |
| 7,090,639 B2 | 8/2006 | Govari |
| 7,194,294 B2 | 3/2007 | Panescu et al. |
| 7,197,354 B2 | 3/2007 | Sobe |
| 7,214,191 B2 | 5/2007 | Stringer et al. |
| 7,311,679 B2 | 12/2007 | Desilets et al. |
| 7,364,546 B2 | 4/2008 | Panescu et al. |
| 7,433,504 B2 | 10/2008 | Deischinger et al. |
| 7,477,763 B2 | 1/2009 | Willis et al. |
| 7,493,154 B2 | 2/2009 | Bonner et al. |
| 7,517,318 B2 | 4/2009 | Altmann et al. |
| 7,520,857 B2 | 4/2009 | Chalana et al. |
| 7,536,218 B2 | 5/2009 | Govari et al. |
| 7,555,330 B2 | 6/2009 | Gilboa et al. |
| 7,604,601 B2 | 10/2009 | Altmann et al. |
| 7,637,885 B2 | 12/2009 | Maschke |
| 7,677,078 B2 | 3/2010 | Sauer et al. |
| 7,686,767 B2 | 3/2010 | Maschke |
| 7,713,210 B2 | 5/2010 | Byrd et al. |
| 7,735,349 B2 | 6/2010 | Hochmitz |
| 7,740,584 B2 | 6/2010 | Donaldson et al. |
| 7,749,168 B2 | 7/2010 | Maschke et al. |
| 7,766,833 B2 | 8/2010 | Lee et al. |
| 7,766,836 B2 | 8/2010 | Waki |
| 7,769,427 B2 | 8/2010 | Shachar |
| 7,774,043 B2 | 8/2010 | Mills |
| 7,778,688 B2 | 8/2010 | Strommer |
| 7,803,116 B2 | 9/2010 | Sikdar et al. |
| 7,806,828 B2 | 10/2010 | Stringer |
| 7,806,829 B2 | 10/2010 | Hauck |
| 7,819,810 B2 | 10/2010 | Stringer et al. |
| 7,822,464 B2 | 10/2010 | Maschke et al. |
| 7,831,076 B2 | 11/2010 | Altmann et al. |
| 7,837,625 B2 | 11/2010 | Abe |
| 7,848,789 B2 | 12/2010 | Govari et al. |
| 7,854,237 B2 | 12/2010 | Irland |
| 7,871,379 B2 | 1/2011 | Ohtsuka |
| 7,873,401 B2 | 1/2011 | Shachar |
| 7,881,769 B2 | 2/2011 | Sobe |
| 7,927,279 B2 | 4/2011 | Kubota et al. |
| 7,938,847 B2 | 5/2011 | Fanton et al. |
| 7,961,924 B2 | 6/2011 | Viswanathan |
| 7,967,808 B2 | 6/2011 | Fitzgerald et al. |
| 7,969,142 B2 | 6/2011 | Krueger et al. |
| 7,981,038 B2 | 7/2011 | Kanade et al. |
| 7,996,057 B2 | 8/2011 | Govari et al. |
| RE42,856 E | 10/2011 | Karmarkar et al. |
| 8,041,411 B2 | 10/2011 | Camus |
| 8,041,413 B2 | 10/2011 | Barbagli et al. |
| 8,082,021 B2 | 12/2011 | Hyde et al. |
| 8,086,298 B2 | 12/2011 | Whitmore, III et al. |
| 8,126,534 B2 | 2/2012 | Maschke |
| 8,167,810 B2 | 5/2012 | Maschke |
| 8,172,757 B2 | 5/2012 | Jaffe et al. |
| 8,175,682 B2 | 5/2012 | Hamm et al. |

(56) References Cited

U.S. PATENT DOCUMENTS

| | | |
|---|---|---|
| 8,196,471 B2 | 6/2012 | Han et al. |
| 8,206,404 B2 | 6/2012 | De La Rama et al. |
| 8,211,025 B2 | 7/2012 | Donaldson et al. |
| 8,212,554 B2 | 7/2012 | Brazdeikis et al. |
| 8,214,015 B2 | 7/2012 | Macaulay et al. |
| 8,216,149 B2 | 7/2012 | Oonuki et al. |
| 8,228,347 B2 | 7/2012 | Beasley et al. |
| 8,257,261 B2 | 9/2012 | Kawae |
| RE43,750 E | 10/2012 | Martinelli et al. |
| 8,292,817 B2 | 10/2012 | Mori |
| 8,298,149 B2 | 10/2012 | Hastings et al. |
| 8,303,507 B2 | 11/2012 | Baba et al. |
| 8,320,711 B2 | 11/2012 | Altmann et al. |
| 8,332,013 B2 | 12/2012 | Strommer |
| 8,335,555 B2 | 12/2012 | Lehman |
| 8,343,052 B2 | 1/2013 | Kawagishi et al. |
| 8,359,086 B2 | 1/2013 | Maschke |
| 8,366,738 B2 | 2/2013 | Dehnad |
| 8,388,541 B2 | 3/2013 | Stats et al. |
| 8,388,546 B2 | 3/2013 | Rothenberg |
| 8,412,311 B2 | 4/2013 | Kenneth |
| 8,428,690 B2 | 4/2013 | Li et al. |
| 8,428,691 B2 | 4/2013 | Byrd et al. |
| 8,439,840 B1 | 5/2013 | Duffy |
| 8,452,376 B2 | 5/2013 | Elgort et al. |
| 8,473,029 B2 | 6/2013 | Gerhart et al. |
| 8,475,524 B2 | 7/2013 | Schwartz |
| 8,478,382 B2 | 7/2013 | Burnside et al. |
| 8,480,588 B2 | 7/2013 | Kanade et al. |
| 8,485,976 B2 | 7/2013 | Iimura et al. |
| 8,496,586 B2 | 7/2013 | Zhang et al. |
| 8,512,256 B2 | 8/2013 | Rothenberg |
| 8,527,032 B2 | 9/2013 | Li |
| 8,535,229 B2 | 9/2013 | Umemura et al. |
| 8,577,105 B2 | 11/2013 | Abe et al. |
| 8,591,417 B2 | 11/2013 | Suzuki et al. |
| 8,634,619 B2 | 1/2014 | Yoshiara et al. |
| 8,670,816 B2 | 3/2014 | Green et al. |
| 8,693,011 B2 | 4/2014 | Mori |
| 8,781,555 B2 | 7/2014 | Burnside et al. |
| 8,801,693 B2 | 8/2014 | He et al. |
| 8,857,263 B2 | 10/2014 | Both et al. |
| 8,867,808 B2 | 10/2014 | Satoh et al. |
| 8,885,897 B2 | 11/2014 | Xu et al. |
| 8,900,149 B2 | 12/2014 | He et al. |
| 8,945,147 B2 | 2/2015 | Ritchey et al. |
| 8,971,600 B2 | 3/2015 | Yoshikawa et al. |
| 9,005,127 B2 | 4/2015 | Azuma |
| 9,024,624 B2 | 5/2015 | Brunner |
| 9,055,883 B2 | 6/2015 | Tgavalekos et al. |
| 9,082,178 B2 | 7/2015 | Hyun et al. |
| 9,107,607 B2 | 8/2015 | Hansegard et al. |
| 9,119,557 B2 | 9/2015 | Masui et al. |
| 9,149,568 B2 | 10/2015 | Gerg et al. |
| 9,173,638 B2 | 11/2015 | Govari et al. |
| 9,216,299 B2 | 12/2015 | Wolfe |
| 9,220,480 B2 | 12/2015 | Lee et al. |
| 9,241,683 B2 | 1/2016 | Slayton et al. |
| 9,256,947 B2 | 2/2016 | Gauthier et al. |
| 9,282,324 B2 | 3/2016 | Hamada |
| 9,289,187 B2 | 3/2016 | Owen et al. |
| 9,295,449 B2 | 3/2016 | Zhang et al. |
| 9,307,954 B2 | 4/2016 | Nishigaki |
| 9,308,041 B2 | 4/2016 | Altmann et al. |
| 9,314,222 B2 | 4/2016 | Creighton, IV et al. |
| 9,332,965 B2 | 5/2016 | Lee et al. |
| 9,375,163 B2 | 6/2016 | Ludwin et al. |
| 9,380,999 B2 | 7/2016 | Yoshida et al. |
| 9,390,495 B2 | 7/2016 | Lee et al. |
| 9,439,624 B2 | 9/2016 | Caluser |
| 9,445,780 B2 | 9/2016 | Hossack et al. |
| 9,451,933 B2 | 9/2016 | Duffy |
| 9,456,766 B2 | 10/2016 | Cox et al. |
| 9,474,465 B2 | 10/2016 | Ashe |
| 9,492,104 B2 | 11/2016 | Clark et al. |
| 9,521,961 B2 | 12/2016 | Silverstein et al. |
| 9,554,716 B2 | 1/2017 | Burnside et al. |
| 9,572,549 B2 | 2/2017 | Belevich et al. |
| 9,612,142 B2 | 4/2017 | Kristofferson et al. |
| 9,649,048 B2 | 5/2017 | Cox et al. |
| 2002/0019644 A1 | 2/2002 | Hastings et al. |
| 2004/0015079 A1 | 1/2004 | Berger et al. |
| 2004/0097803 A1 | 5/2004 | Panescu |
| 2004/0249287 A1 | 12/2004 | Kawashima et al. |
| 2005/0021063 A1 | 1/2005 | Hall et al. |
| 2005/0027195 A1 | 2/2005 | Govari |
| 2005/0085718 A1 | 4/2005 | Shahidi |
| 2005/0131289 A1 | 6/2005 | Aharoni et al. |
| 2006/0004291 A1 | 1/2006 | Heimdal et al. |
| 2006/0173304 A1 | 8/2006 | Wang |
| 2006/0174065 A1 | 8/2006 | Kuzara et al. |
| 2006/0184029 A1 | 8/2006 | Haim et al. |
| 2006/0241461 A1 | 10/2006 | White et al. |
| 2006/0247522 A1 | 11/2006 | Mcgee |
| 2006/0253031 A1 | 11/2006 | Altmann et al. |
| 2007/0167769 A1 | 7/2007 | Ikuma et al. |
| 2007/0213616 A1 | 9/2007 | Anderson et al. |
| 2007/0238979 A1 | 10/2007 | Huynh et al. |
| 2008/0021297 A1 | 1/2008 | Boosten |
| 2008/0039725 A1 | 2/2008 | Man et al. |
| 2008/0051652 A1 | 2/2008 | Ichioka et al. |
| 2008/0161840 A1 | 7/2008 | Osiroff et al. |
| 2008/0294037 A1 | 11/2008 | Richter |
| 2009/0018448 A1 | 1/2009 | Seo et al. |
| 2009/0093712 A1 | 4/2009 | Busch et al. |
| 2009/0105579 A1 | 4/2009 | Garibaldi |
| 2009/0118620 A1 | 5/2009 | Tgavalekos et al. |
| 2009/0131797 A1 | 5/2009 | Jeong et al. |
| 2009/0137900 A1 | 5/2009 | Bonner et al. |
| 2009/0143676 A1 | 6/2009 | Matsumura |
| 2009/0163810 A1 | 6/2009 | Kanade et al. |
| 2009/0192385 A1 | 7/2009 | Meissner et al. |
| 2009/0306497 A1 | 12/2009 | Manzke et al. |
| 2010/0016726 A1 | 1/2010 | Meier |
| 2010/0049052 A1 | 2/2010 | Sharf et al. |
| 2010/0063398 A1 | 3/2010 | Halmann et al. |
| 2010/0113919 A1 | 5/2010 | Maschke |
| 2010/0160781 A1 | 6/2010 | Carter et al. |
| 2010/0191101 A1 | 7/2010 | Lichtenstein |
| 2010/0222680 A1 | 9/2010 | Hamada |
| 2010/0249602 A1 | 9/2010 | Buckley et al. |
| 2010/0298713 A1 | 11/2010 | Robinson |
| 2010/0305429 A1 | 12/2010 | Shachar et al. |
| 2011/0092862 A1 | 4/2011 | Chivers |
| 2011/0125022 A1 | 5/2011 | Lazebnik |
| 2011/0142319 A1 | 6/2011 | Lee et al. |
| 2011/0194748 A1 | 8/2011 | Tonomura et al. |
| 2011/0196238 A1 | 8/2011 | Jacobson et al. |
| 2011/0196397 A1 | 8/2011 | Frantz et al. |
| 2011/0224550 A1 | 9/2011 | Shinohara |
| 2011/0230763 A1 | 9/2011 | Emery et al. |
| 2011/0230796 A1 | 9/2011 | Emery et al. |
| 2011/0255762 A1 | 10/2011 | Deischinger et al. |
| 2011/0301460 A1 | 12/2011 | Anite |
| 2012/0046553 A9 | 2/2012 | Buckley et al. |
| 2012/0065499 A1 | 3/2012 | Chono |
| 2012/0070051 A1 | 3/2012 | Vincent et al. |
| 2012/0071752 A1 | 3/2012 | Sewell et al. |
| 2012/0143029 A1 | 6/2012 | Silverstein et al. |
| 2012/0165671 A1 | 6/2012 | Hill et al. |
| 2012/0197113 A1 | 8/2012 | Courtney et al. |
| 2012/0209114 A1 | 8/2012 | Staalsen et al. |
| 2012/0220854 A1 | 8/2012 | Stats et al. |
| 2012/0245457 A1 | 9/2012 | Crowley |
| 2012/0259209 A1 | 10/2012 | Harhen |
| 2012/0289830 A1 | 11/2012 | Halmann et al. |
| 2012/0289836 A1 | 11/2012 | Ukimura et al. |
| 2012/0310093 A1 | 12/2012 | Tanabe et al. |
| 2013/0006100 A1 | 1/2013 | Shachar et al. |
| 2013/0006111 A1 | 1/2013 | Sasaki |
| 2013/0009957 A1 | 1/2013 | Arakita |
| 2013/0012820 A1 | 1/2013 | Brown et al. |
| 2013/0018264 A1 | 1/2013 | Gerard et al. |
| 2013/0060116 A1 | 3/2013 | Stats et al. |

(56) References Cited

U.S. PATENT DOCUMENTS

| | | |
|---|---|---|
| 2013/0066193 A1 | 3/2013 | Olson et al. |
| 2013/0085416 A1 | 4/2013 | Mest |
| 2013/0102889 A1 | 4/2013 | Southard et al. |
| 2013/0102903 A1 | 4/2013 | Tanaka et al. |
| 2013/0123614 A1 | 5/2013 | Bernstein et al. |
| 2013/0165782 A1 | 6/2013 | Yawata |
| 2013/0165784 A1 | 6/2013 | Kim et al. |
| 2013/0172745 A1 | 7/2013 | Choi |
| 2013/0172747 A1 | 7/2013 | Kim et al. |
| 2013/0172748 A1 | 7/2013 | Kim |
| 2013/0184569 A1 | 7/2013 | Strommer et al. |
| 2013/0195313 A1 | 8/2013 | Gauthier et al. |
| 2013/0197365 A1 | 8/2013 | Baba |
| 2013/0217997 A1 | 8/2013 | Byrd et al. |
| 2013/0237826 A1 | 9/2013 | Levien |
| 2013/0253319 A1 | 9/2013 | Hamilton et al. |
| 2013/0289411 A1 | 10/2013 | Barnard et al. |
| 2013/0296691 A1 | 11/2013 | Ashe |
| 2013/0303886 A1 | 11/2013 | Ludwin et al. |
| 2013/0303915 A1 | 11/2013 | Barnard et al. |
| 2013/0317334 A1 | 11/2013 | Bar-Tal et al. |
| 2013/0331697 A1 | 12/2013 | Park et al. |
| 2014/0035914 A1 | 2/2014 | Noshi et al. |
| 2014/0039307 A1 | 2/2014 | Harhen |
| 2014/0051984 A1 | 2/2014 | Berger et al. |
| 2014/0107487 A1 | 4/2014 | Kim et al. |
| 2014/0187919 A1 | 7/2014 | Parthasarathy et al. |
| 2014/0187950 A1 | 7/2014 | Torp et al. |
| 2014/0364734 A1 | 12/2014 | Huang |
| 2015/0073266 A1 | 3/2015 | Brannan et al. |
| 2015/0173706 A1 | 6/2015 | Andrews et al. |
| 2015/0320386 A9 | 11/2015 | Liu |
| 2016/0007842 A1 | 1/2016 | Govari et al. |
| 2016/0331351 A1 | 11/2016 | Guracar |
| 2016/0338675 A1 | 11/2016 | Kubota |
| 2018/0279996 A1 | 10/2018 | Cox et al. |
| 2018/0296185 A1 | 10/2018 | Cox et al. |

FOREIGN PATENT DOCUMENTS

| | | |
|---|---|---|
| WO | 2014001963 A1 | 1/2014 |
| WO | 2014099825 A3 | 9/2014 |
| WO | 2014001963 A9 | 2/2015 |
| WO | 2016081023 A1 | 5/2016 |
| WO | 2016081321 A2 | 5/2016 |

OTHER PUBLICATIONS

Anonymous "Aurora", Retrieved from the Internet: http://www.ndigital.com/medical/products/aurora, retrieved on Jun. 30, 2015.
Extended European search report dated May 11, 2022, pertaining to EP Application 22154728.4.

ULTRASOUND IMAGING SYSTEM HAVING AUTOMATIC IMAGE PRESENTATION

CROSS-REFERENCE TO RELATED APPLICATIONS

This application is a divisional of U.S. patent application Ser. No. 16/842,930, filed Apr. 8, 2020, which is a divisional of U.S. patent application Ser. No. 15/525,319, filed May 9, 2017, which is a U.S. national phase of International Application No. PCT/US2015/060704, filed Nov. 13, 2015, which claims priority to international patent application serial no. PCT/US2015/018068, filed Feb. 27, 2015, and to U.S. provisional patent application Ser. Nos. 62/081,275, filed Nov. 18, 2014, and 62/081,530, filed Nov. 18, 2014, each of which is incorporated herein by reference in its entirety.

BACKGROUND OF THE INVENTION

1. Field of the Invention

The present invention relates to ultrasound imaging, and, more particularly, to an ultrasound imaging system that assists in the positioning of an ultrasound probe.

2. Description of the Related Art

Correctly positioning an ultrasound probe such that a diagnostically relevant image is produced is a skill often only obtained after training and consistent ultrasound use. This initial "training period" necessary to become proficient in ultrasound imaging may be a contributing factor to the current underutilization of ultrasound by non-sonographers.

What is needed in the art is an ultrasound imaging system, as in the present invention, which assists a person not experienced in ultrasound imaging in successful image acquisition, via system assisted positioning of an ultrasound probe, such that an image of a location of interest under, i.e., in the imaging view of, the ultrasound probe can be displayed.

SUMMARY OF THE INVENTION

The present invention provides an ultrasound imaging system that assists in image acquisition, and in positioning of an ultrasound probe, such that an image of a location of interest under, i.e., in the imaging view of, the probe can be displayed. For example, the ultrasound imaging system assists in the positioning of an ultrasound probe such that a specific image containing a medical device and/or the surrounding area can automatically be presented to the user. The system may further be used to create three-dimensional (3D) images of underlying structures, which may convey additional information regarding the state of the underlying anatomy. This may assist one performing peripheral arterial disease (PAD) or other interventional procedures.

The invention in one form is directed to an ultrasound imaging system that includes an electromagnetic (EM) field generator configured to generate an EM locator field. An interventional medical device is defined by an elongate body having a distal tip and a distal end portion extending proximally from the distal tip. The interventional medical device has a first tracking element mounted at the distal end portion of the interventional medical device. The first tracking element is configured to generate tip location data based on the EM locator field. An ultrasound probe has a probe housing, an ultrasound transducer mechanism, and a second tracking element. The probe housing has a handle portion and a head portion. The ultrasound transducer mechanism and the second tracking element are mounted to the probe housing. The ultrasound transducer mechanism has an active ultrasound transducer array configured to generate two-dimensional ultrasound slice data at any of a plurality of discrete imaging locations within a three-dimensional imaging volume associated with the head portion. The second tracking element is configured to generate probe location data based on the EM locator field. A display screen is configured to display an ultrasound image. A processor circuit is communicatively coupled to the first tracking element, the second tracking element, the ultrasound transducer mechanism, and the display screen. The processor circuit is configured to execute program instructions to process the two-dimensional ultrasound slice data to generate the ultrasound image for display at the display screen. Also, the processor circuit is configured to generate a positioning signal based on the tip location data and the probe location data to dynamically position the active ultrasound transducer array at a desired imaging location of the plurality of discrete imaging locations so that the two-dimensional ultrasound slice data includes at least the distal tip of the interventional medical device so long as a location of the distal tip of the interventional medical device remains in the three-dimensional imaging volume.

A further version of the invention lies in the electromagnetic field generator adapted for use in such a system, the interventional medical device adapted for use in such a system, an ultrasound probe adapted for use in such a system, a display screen adapted for use in such a system, and a processor circuit adapted for use in such a system. An alternative version of the invention lies in a system comprising a combination of any of the objects recited in the previous sentence.

The invention in another form is directed to a method of operating an ultrasound imaging system, including acquiring a position of a first tracking element associated with an interventional medical device; acquiring a position of a second tracking element associated with an ultrasound probe; determining an ultrasound imaging plane position of the ultrasound probe based on the position of the second tracking element; determining an offset distance between the position of first tracking element of the interventional medical device and the ultrasound plane position; and driving an ultrasound transducer mechanism to position an active ultrasound transducer array of the ultrasound probe at a determined point of convergence as defined by the offset distance.

In accordance with another aspect of the invention, a motion indicator is located on at least one of the ultrasound probe and the display screen. The processor circuit is operably coupled to the motion indicator, wherein if the distal tip of the interventional medical device is presently located outside the three-dimensional imaging volume, a visual prompt is generated at the motion indicator to prompt the user to move the head portion of the ultrasound probe in a particular direction to a general location such that the distal tip of the interventional medical device resides in the three-dimensional imaging volume.

In accordance with another aspect of the invention, a third tracking element is attached to a patient, wherein when the third tracking element is energized by the EM field generator. The third tracking element generates six axis patient location data, which is supplied to the processor circuit. The processor circuit processes the six-axis patient location data and assigns location information for images captured by the active ultrasound transducer array to known positions within a 3D volume referenced from the third tracking element.

In accordance with another aspect of the invention, the ultrasound imaging system has a three-dimensional imaging mode, wherein with the ultrasound probe held in a fixed position over an area of interest, a scanning signal is supplied to the ultrasound transducer mechanism to scan the active ultrasound transducer array over at least a portion of the possible imaging volume located below the transducer array. The active transducer array is repeatedly actuated during the scan to generate a plurality of sequential two-dimensional ultrasound data slices which are combined to form three-dimensional ultrasound volumetric data from which a three-dimensional ultrasound image is generated.

In accordance with another aspect of the invention, the active ultrasound transducer array is operated to generate multiple sets of ultrasound image data that includes metadata describing the location of the scan within the three-dimensional volume. The multiple sets of ultrasound image data are summed to generate composite ultrasound image data.

In accordance with another aspect of the invention, a desired image plane is defined in the three-dimensional ultrasound volumetric data. At least one synthetic scan plane is generated corresponding to the desired image plane.

In accordance with another aspect of the invention, a first two-dimensional ultrasound image slice is generated from a series of two-dimensional B-scan ultrasound image slices acquired from the three-dimensional ultrasound volumetric data. The first two-dimensional ultrasound image slice includes a particular region of interest. The first two-dimensional ultrasound image slice lies in a first imaging plane different from that of the native B-scan imaging plane of the series of two-dimensional ultrasound image slices. At least one slice selection slider provides a sequential parallel variation from the first two-dimensional ultrasound image slice to manually select a second two-dimensional ultrasound image slice parallel to the first two-dimensional ultrasound image, wherein the second two-dimensional ultrasound image slice lies on either side of the first two-dimensional ultrasound image slice.

In accordance with another aspect of the invention, an orientation of the ultrasound image that is displayed on a display screen is adjusted such that a vertical top of the acquired ultrasound image data is always rendered as "up" on the display screen relative to the position of the patient, and regardless of the actual orientation of ultrasound probe relative to the patient.

Another aspect of the invention is directed to a method of operating an ultrasound imaging system, including acquiring a position of a first tracking element associated with an interventional medical device; acquiring a position of a second tracking element associated with an ultrasound probe; determining an ultrasound imaging plane position of the ultrasound probe based on the position of the second tracking element; determining an offset distance between the position of first tracking element of the interventional medical device and the ultrasound plane position; and using the offset distance to dynamically control at least one ultrasound imaging setting of the ultrasound imaging system in near real time. As used herein, the term "near real time" means real time as limited by data acquisition and processing speed of the processing system. The at least one ultrasound imaging setting may include ultrasound focus, such that a lateral resolution is optimized at a depth that contains the interventional medical device. Also, the at least one ultrasound imaging setting may include a depth setting, such that a depth of imaging is automatically adjusted to match a depth of the interventional medical device. Also, the at least one ultrasound imaging setting may include zoom, wherein an imaging window can be "zoomed" such that a larger view of an area of interest is automatically displayed to the user.

Another aspect of the invention is directed to a method of generating a 3D ultrasound image and providing an interventional medical device aligned mode, including acquiring a 3D volumetric data set corresponding to a 3D imaging volume of an ultrasound probe in a 3D detection volume; acquiring a position of the ultrasound probe with respect to the 3D detection volume; acquiring a position of an interventional medical device with respect to the 3D detection volume; determining a position of interventional medical device relative to the 3D imaging volume of the ultrasound probe; determining an interventional medical device-aligned plane that intersects with a longitudinal axis of the interventional device; extracting a texture slice from the 3D imaging volume for a corresponding interventional medical device-aligned plane positional and rotational orientation; mapping the texture slice onto the interventional medical device-aligned plane; and rendering the interventional medical device-aligned plane as a 3D ultrasound image and displaying the rendered 3D ultrasound image on a display screen.

Another aspect of the invention is directed to a method of using an ultrasound imaging system having an ultrasound probe and a display screen for imaging a region of interest in a patient, including operating the ultrasound probe to generate a 3D image volume from a plurality of individual 2D ultrasound image slices; detecting a Doppler shift that is created in an ultrasound return signal due to motion of surrounding tissues that resonate as a result of a vibration source positioned inside the patient; selecting a 2D ultrasound image slice, of plurality of individual 2D ultrasound image slices, that contains the Doppler shift, the selected 2D ultrasound image slice providing a visualization of the vibration source and the surrounding tissues; and displaying the selected 2D ultrasound image slice on the display screen.

Another aspect of the invention is directed to a method of using an ultrasound imaging system having an ultrasound probe and a display screen for imaging a region of interest in a patient, including operating the ultrasound probe to acquire a sequence of 3D data sets from a fixed location relative to the patient, each 3D data set representing the same 3D image volume, the 3D image volume being formed from a plurality of individual 2D ultrasound image slices; processing the sequence of 3D data sets in a spatiotemporal domain using a motion filter algorithm to identify Cartesian coordinates of a location of motion within the 3D image volume; selecting a 2D ultrasound image slice, of plurality of individual 2D ultrasound image slices, that contains the Cartesian coordinates of the location of motion; and displaying the selected 2D ultrasound image slice on the display screen.

Another aspect of the invention is directed to a method for generation of a virtual segmented representation of a vasculature, including acquiring a 3D volume of 3D ultrasound data which includes metadata for a location of each 2D ultrasound image within the 3D volume to form a 3D data set; displaying, at predetermined stepwise increments within the 3D dataset, a 2D ultrasound image to a user; selecting an open lumen of interest of the vasculature on the displayed 2D ultrasound image; selecting a beginning point in the selected open lumen of interest of the vasculature; invoking a segmentation algorithm to expand and designate a full luminal area of the open lumen of interest of a current 2D ultrasound image slice; displaying the full luminal area of the open lumen of interest of the current 2D ultrasound image slice to the user for evaluation; saving data associated with the full luminal area; calculating a center point of full luminal area; projecting the center point onto an adjacent 2D ultrasound image slice; and repeating the steps of invoking, saving, calculating and projecting until an ending point has been reached, at which time a first 2D virtual image segment has been generated.

The method may further include, prior to the act of repeating, stitching the adjacent 2D ultrasound image slices together to form a 3D segmentation model; and displaying the 3D segmentation model on a display screen.

In accordance with another aspect of the invention, an ultrasound probe includes a housing, a first one-dimensional ultrasound transducer array, and a second one-dimensional ultrasound transducer array. The first one-dimensional ultrasound transducer array and a second one-dimensional ultrasound transducer array are contained in the housing. The first one-dimensional ultrasound transducer array and the second one-dimensional ultrasound transducer array are oriented in a first direction. The second one-dimensional ultrasound transducer array is arranged in parallel with the first one-dimensional ultrasound transducer array. A first electromechanical drive is contained within the housing, and is configured to move the first one-dimensional ultrasound transducer array in a transverse direction perpendicular to the first direction to define a first sweep pattern. A second electromechanical drive is contained within the housing, and is configured to move the second one-dimensional ultrasound transducer array in a transverse direction perpendicular to the first direction to define a second sweep pattern. An electronic control circuit is electrically coupled to the first electromechanical drive and to the second electromechanical drive. The electronic control circuit is configured to provide first control signals to each of the first electromechanical drive and the second electromechanical drive to generate a first composite sweep pattern of the first one-dimensional ultrasound transducer array and the second one-dimensional ultrasound transducer array as a combination of the first sweep pattern and the second sweep pattern.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
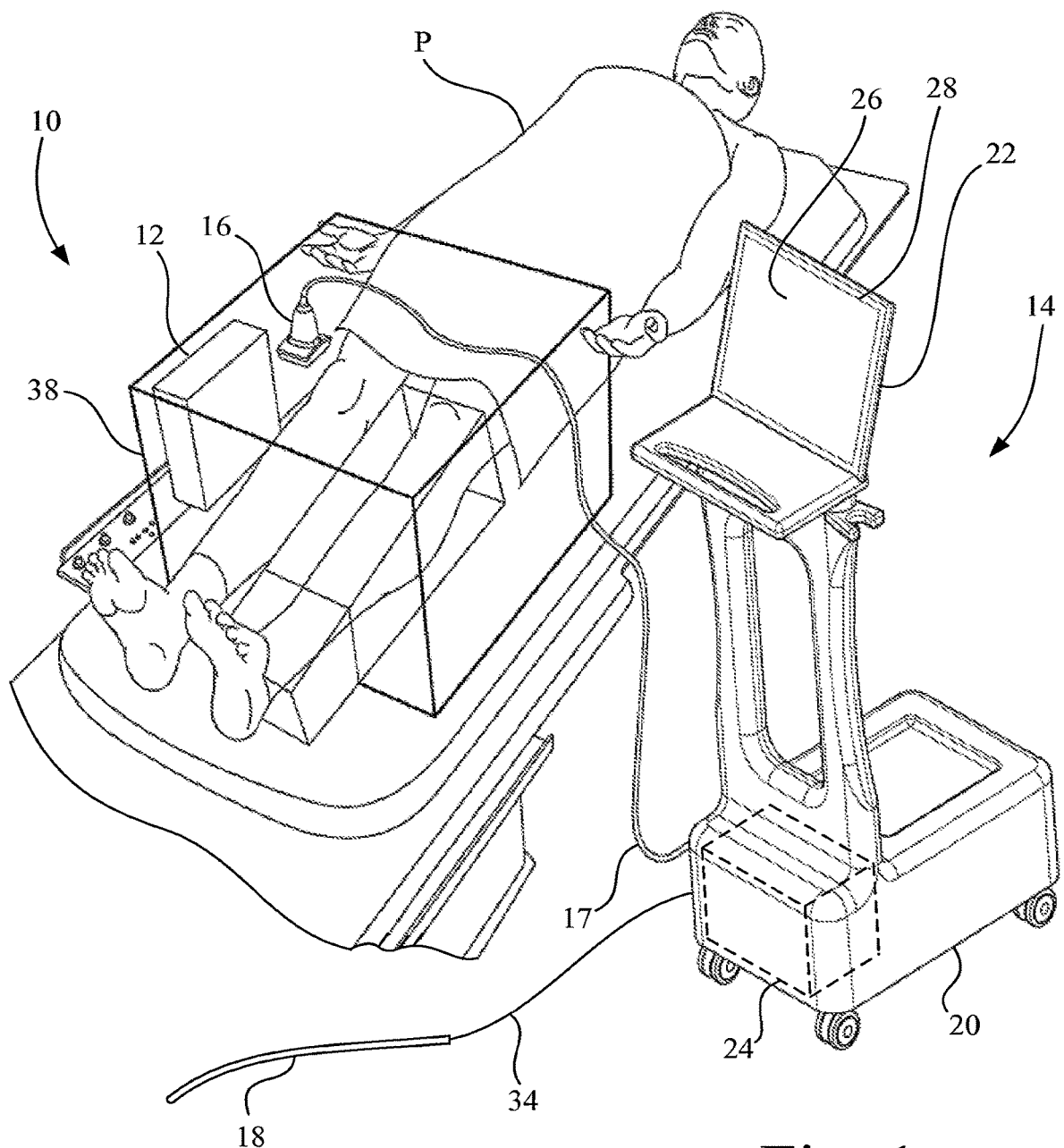
FIG. 1 is an illustration of an ultrasound imaging system in accordance with an aspect of the present invention.
Figure 2:
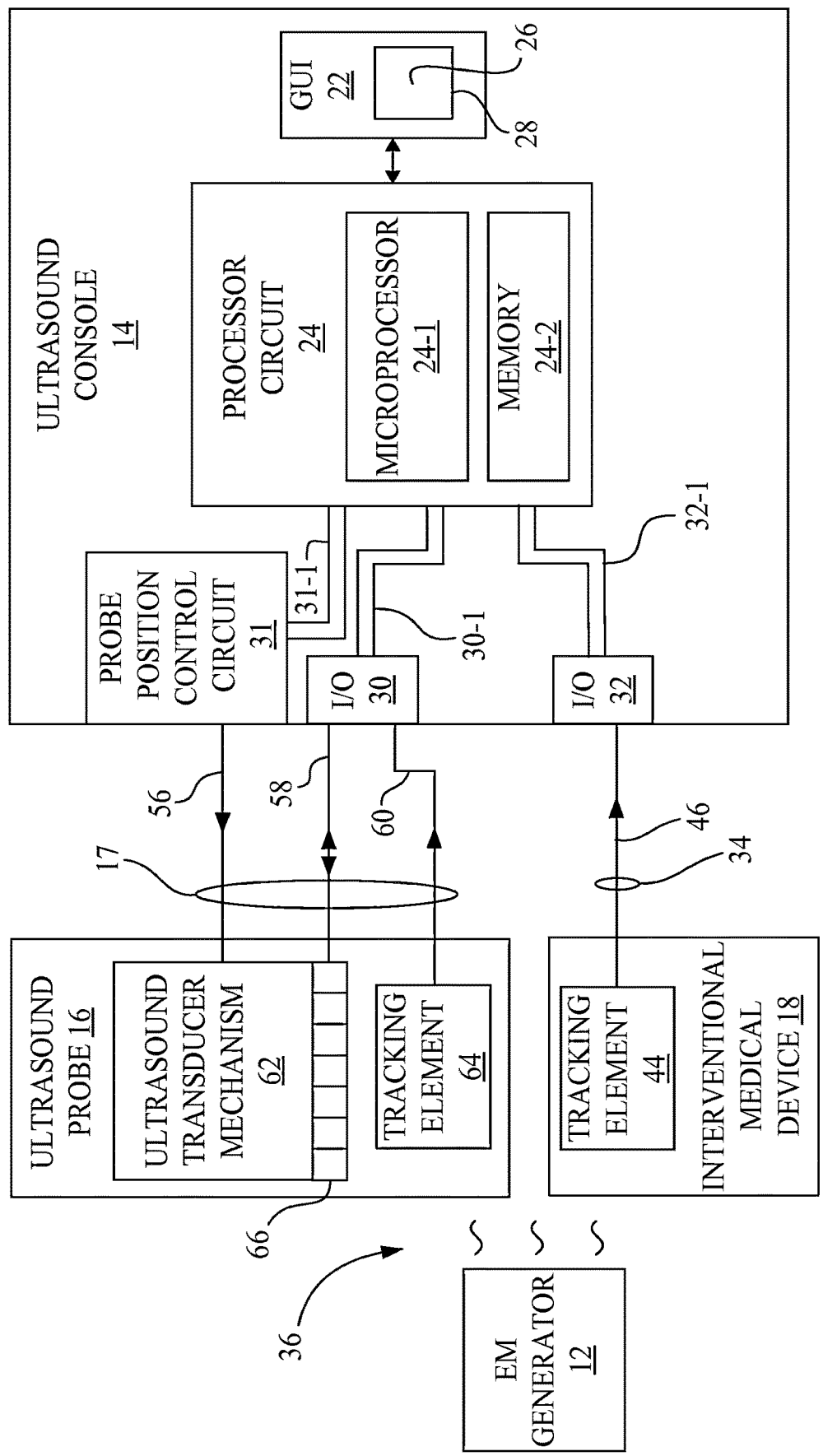
FIG. 2 is an electrical block diagram of the ultrasound imaging system of FIG. 1.

Referring now to the drawings, and more particularly to FIGS. 1 and 2, there is shown an ultrasound imaging system 10 in accordance with the present invention.

Ultrasound imaging system 10 includes an electromagnetic (EM) field generator 12, an ultrasound console 14, and an ultrasound probe 16 (handheld). Ultrasound probe 16 is connected to an ultrasound console 14 by a flexible electrical cable 17. Supplemental to ultrasound imaging system 10 is an interventional medical device 18.

As used herein, the term "interventional medical device" is an elongate intrusive medical device that is configured to be inserted into the tissue, vessel or cavity of a patient. In the context of the present invention, interventional medical device 18 may be, for example, a catheter, a lesion crossing catheter such as the CROSSER® Catheter available from C. R. Bard, Inc., a guide wire, a sheath, an angioplasty balloon, a stent delivery catheter, or a needle. It is intended that the interventional medical device 18 may be considered as a part of the overall ultrasound imaging system 10, but alternatively, also may be considered as an auxiliary part of ultrasound imaging system 10 as a separately provided item.

Ultrasound imaging system 10 is configured to track the location of the ultrasound probe 16 and interventional medical device 18, and in turn, to operate ultrasound probe 16 such that an active ultrasound transducer array of ultrasound probe 16 is dynamically positioned to image a desired portion of interventional medical device 18, as further described below.

In the present embodiment, ultrasound console 14 includes a mobile housing 20, to which is mounted a graphical user interface 22, and a processor circuit 24. Graphical user interface 22 may be in the form of a touch-screen display 26 having a display screen 28. Graphical user interface 22 is used in displaying information to the user, and accommodates user input via the touch-screen 26. For example, touch-screen 26 is configured to display an ultrasound image formed from two-dimensional ultrasound slice data provided by ultrasound probe 16, to display virtual location information of tracked elements within a 3D volume, and to display prompts intended to guide the user in the correct positioning of the ultrasound probe 16 above the area of interest. In addition, display screen 28 may be configured as a standard 2D display, or optionally, may be configured as a 3D display. For example, it is envisioned that the 3D dataset captured by ultrasound imaging system 10 may be presented to the user via an autostereoscopic or other display method that presents a 3D image to the user.

Processor circuit 24 is an electrical circuit that has data processing capability and command generating capability, and in the present embodiment has a microprocessor 24-1 and associated non-transitory electronic memory 24-2. Microprocessor 24-1 and associated non-transitory electronic memory 24-2 are commercially available components, as will be recognized by one skilled in the art. Microprocessor 24-1 may be in the form of a single microprocessor, or two or more parallel microprocessors, as is known in the art. Non-transitory electronic memory 24-2 may include multiple types of digital data memory, such as random access memory (RAM), non-volatile RAM (NVRAM), read only memory (ROM), and/or electrically erasable programmable read-only memory (EEPROM). Non-transitory electronic memory 24-2 may further include mass data storage in one or more of the electronic memory forms described above, or on a computer hard disk drive or optical disk. Alternatively, processor circuit 24 may be assembled as one or more Application Specific Integrated Circuits (ASIC).

Processor circuit 24 processes program instructions received from a program source, such as software or firmware, to which processor circuit 24 has electronic access. More particularly, processor circuit 24 is configured, as more fully described below, to process location signals received from ultrasound probe 16 and interventional medical device 18, and to generate a digital positioning signal that is conditioned and provided as a control output to ultrasound probe 16. More particularly, the digital positioning signal and control output correspond to a coordinate in the scan axis, e.g., the y-axis, of ultrasound probe 16 where the active ultrasound transducer array of ultrasound probe 16 is to be positioned.

Processor circuit 24 is communicatively coupled to a probe input/output (I/O) interface circuit 30, a probe position control circuit 31, and a device input/output (I/O) interface circuit 32 via an internal bus structure 30-1, 31-1, and 32-1, respectively. As used herein, the term "communicatively coupled" means connected for communication over a communication medium, wherein the communication medium may be a direct wired connection having electrical conductors and/or printed circuit electrical conduction paths, or a wireless connection, and may be an indirect wired or wireless connection having intervening electrical circuits, such as amplifiers or repeaters. Probe input/output (I/O) interface circuit 30 and probe position control circuit 31 are configured to connect to electrical cable 17, which in turn is connected to ultrasound probe 16. In the present embodiment, device input/output (I/O) interface circuit 32 is configured to connect to a flexible electrical cable 34, which in turn is connected to interventional medical device 18.

Referring again to FIG. 1, EM field generator 12 is placed near the area of interest of the patient P, and is used in triangulating the location of one or more tracked elements, such as the position of ultrasound probe 16 and interventional medical device 18. EM field generator 12 may be, for example, the field generator of an Aurora® Electromagnetic Tracking System available from Northern Digital Inc. (NDI), which generates a base electromagnetic field that radiates in a known orientation to facilitate electromagnetic spatial measurement, which will be referred to hereinafter as an EM locator field 36 (see FIG. 2). The field strength of the EM locator field 36 defines a detection volume 38, as diagrammatically illustrated as a cube volume, for convenience, in FIG. 1.

Figure 3:
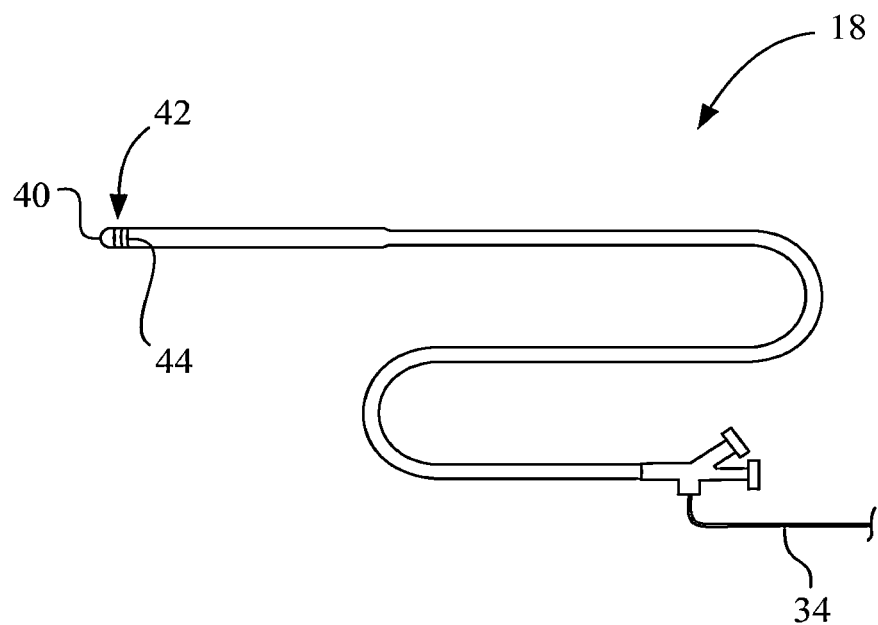
FIG. 3 shows an interventional medical device, such as a catheter or sheath, having a tracking element near its distal tip.

Referring also to FIG. 3, interventional medical device 18 has a distal tip 40 and a distal end portion 42 extending proximally from the distal tip 40. In the present embodiment, a tracking element 44 (i.e., a wire electrical tracking coil) is mounted at distal end portion 42 of interventional medical device 18 near distal tip 40. In the context of the preceding sentence, the term "near" is a range of zero to 2 centimeters (cm), and the extent of distal end portion 42 is in a range of 1 millimeter (mm) to 3 cm. Those skilled in the art will recognize, however, that the exact location of the placement of tracking element 44 on interventional medical device 18 will depend on the portion of interventional medical device 18 that is to be tracked by ultrasound imaging system 10. Tracking element 44 allows the location of interventional medical device 18 to be known relative to ultrasound probe 16, as more fully described below.

Tracking element 44 is configured to generate tip location data defining five degrees of freedom based on the EM locator field 36 generated by EM field generator 12. The five degrees of freedom are the X-axis, Y-axis, Z-axis, pitch, and yaw. A sixth degree of freedom, i.e., roll, may be also included, if desired. Tracking element 44 of interventional medical device 18 is communicatively coupled to processor circuit 24 of ultrasound console 14 via electrical cable 34, serving as a communication link 46 between processor circuit 24 and tracking element 44. As used herein, "communications link" refers to an electrical transmission of data, i.e., information, and/or electrical power signals, over a wired or wireless communication medium. In the present embodiment, the communication link 46 provided by electrical cable 34 is a multi-conductor electrical cable that physically connects tracking element 44 to the ultrasound console 14, and in turn to processor circuit 24.

Figure 4:
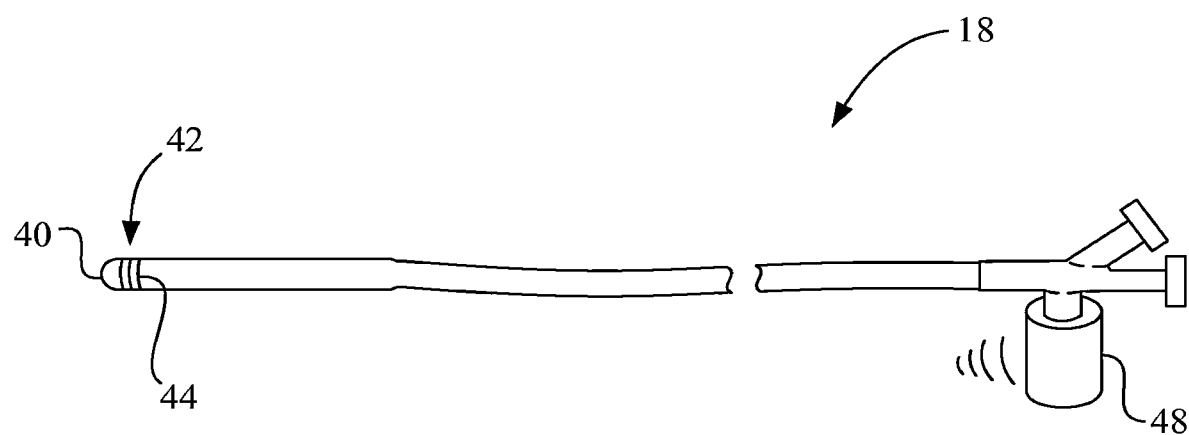
FIG. 4 shows an interventional medical device, such as a catheter, having a wireless dongle.

Alternatively, as depicted in FIG. 4, in place of a physical connection, communication link 46 may be in the form of a short range wireless connection, such as Bluetooth, via a Bluetooth dongle 48 attached to interventional medical device 18. The Bluetooth dongle 48 is configured as a Bluetooth transmitter using Bluetooth protocol, and a corresponding Bluetooth receiver is connected to processor circuit 24. Bluetooth dongle 48 communicates tracking information from tracking element 44, and other information associated with interventional medical device 18, such as an operating state, to processor circuit 24 of ultrasound imaging system 10. Also, Bluetooth dongle 48 may be used to provide power to the EM tracking components incorporated into interventional medical device 18, in the case where the EM tracking component is an active circuit requiring a power source.

Bluetooth dongle 48 may be disposable, and included with each interventional medical device 18. Alternatively, Bluetooth dongle 48 may be reusable. Sterility requirements for the reusable dongle are addressed by placing the sterilized dongle in a sterile bag through which a sterile connection to interventional medical device 18 is made.

Figure 5A:
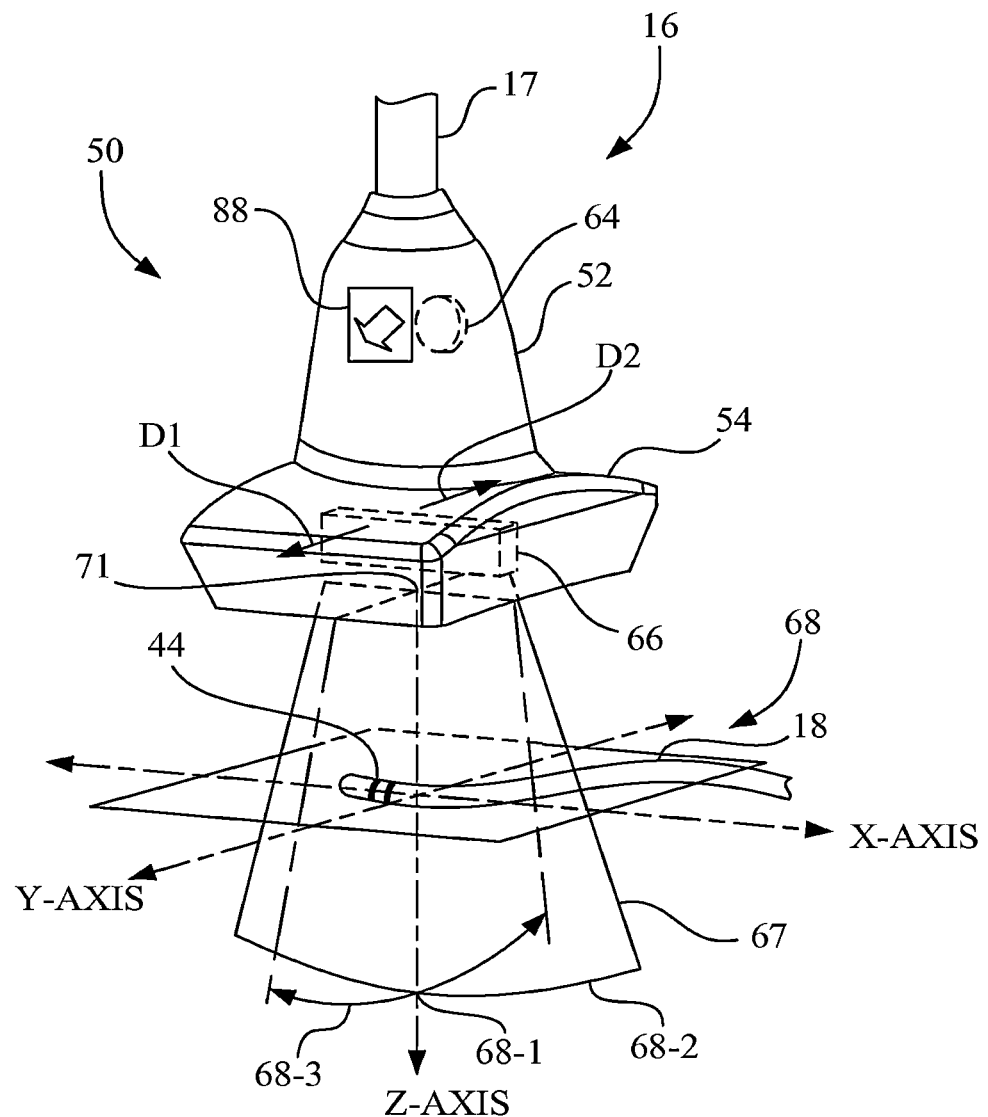
FIG. 5A shows the ultrasound probe of FIG. 1 having an ultrasound transducer mechanism with an active ultrasound transducer array configured to generate two-dimensional ultrasound slice data.

As shown in FIG. 5A, ultrasound probe 16 includes a probe housing 50 having a handle portion 52 joined with a head portion 54. In the present embodiment, handle portion 52 has an extent that is generally perpendicular (range of ±5 degrees) to the extent of head portion 54.

Ultrasound probe 16 is communicatively coupled to processor circuit 24 of ultrasound console 14 via electrical cable 17, which may be a wired or a wireless connection. In the present embodiment, with reference to FIG. 2, electrical cable 17 is depicted as a multi-conductor electrical cable that physically connects ultrasound probe 16 to ultrasound console 14, and includes a communication link 56, a communication link 58, and a communication link 60, each formed with wire conductors. However, it is contemplated that one or more of communication link 56, communication link 58, and communication link 60 may be in the form of a (short range) wireless connection, such as Bluetooth. Portions of the processor circuit 24 could also be embedded in the ultrasound probe to analyze or process the received/transmitted signal to the ultrasound emitting element. The analyzed or processed signal is then transmitted back to the console via electrical cable.

Referring to FIG. 2, ultrasound probe 16 includes an ultrasound transducer mechanism 62 and a tracking element 64. Both ultrasound transducer mechanism 62 and tracking element 64 are mounted to probe housing 50 (see also FIG. 5A), and may be contained within probe housing 50, which may be formed from plastic. Also, tracking element 64 may be embedded in the plastic of probe housing 50. Ultrasound transducer mechanism 62 is communicatively coupled to processor circuit 24 via communication links 56 and 58.

Referring to FIGS. 2 and 5A, ultrasound transducer mechanism 62 has an active ultrasound transducer array 66 configured to generate two-dimensional ultrasound slice data representing a two-dimensional ultrasound imaging slice 67 at any of a plurality of discrete imaging locations within a three-dimensional imaging volume 68 associated with head portion 54 of ultrasound probe 16. The three-dimensional imaging volume 68 is defined by a depth 68-1 of penetration of the ultrasound emission in the direction of the z-axis, a width 68-2 of ultrasound emission in the x-axis, and an ultrasound transducer scan extent 68-3 along the y-axis. Active ultrasound transducer array 66 may be, for example, a one-dimensional transducer array in the form of a linear ultrasound transducer array, or alternatively, may be in the form of a convex or concave ultrasound transducer array. As used herein, the term "one-dimensional transducer array" is an array of ultrasound transducer elements arranged in a single row, wherein the row may be linear or curved.

Active ultrasound transducer array 66 is communicatively coupled to processor circuit 24 via communication link 58, and supplies two-dimensional ultrasound data to processor circuit 24 via communication link 58. Automatically, or alternatively based on a user input at graphical user interface 22, processor circuit 24 executes program instructions to store the two-dimensional ultrasound data in mass storage provided in non-transitory electronic memory 24-2.

Figure 5B:
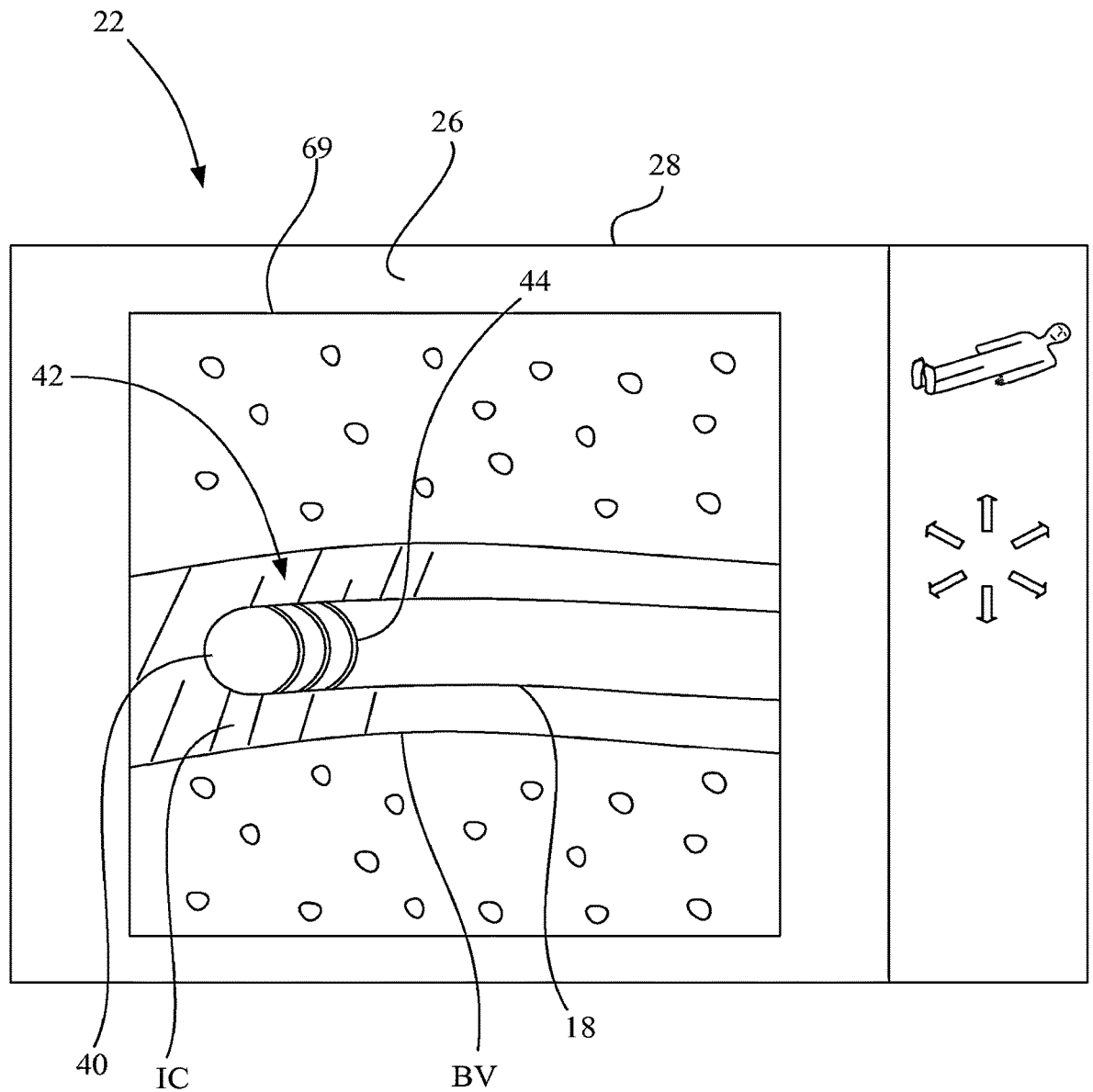
FIG. 5B shows a graphical user interface having a display screen showing a two-dimensional ultrasound image of the two-dimensional ultrasound slice data acquired by the ultrasound probe depicted in FIG. 5A.

Referring also to FIG. 5B, processor circuit 24 includes circuitry, or alternatively executes program instructions, to convert the two-dimensional ultrasound data to a form for viewing as a two-dimensional ultrasound image 69 on display screen 28 of graphical user interface 22. The two-dimensional ultrasound image 69 depicts interventional medical device 18 having tracking element 44 located in a blood vessel BV, and depicts distal tip 40 of distal end portion 42 of interventional medical device 18 engaged with an intravascular occlusion IC.

Referring again to FIGS. 2 and 5A, tracking element 64 (i.e., a wire electrical tracking coil) is configured to generate probe location data defining six degrees of freedom based on the EM locator field 36 generated by EM field generator 12. The six degrees of freedom are the X-axis, Y-axis, Z-axis, pitch, yaw, and roll. Tracking element 64 is communicatively coupled to processor circuit 24 via communication link 60, and supplies probe location data to processor circuit 24 via communication link 60. Tracking element 64 allows for the determination of the location of ultrasound probe 16 within detection volume 38 as depicted in FIG. 1, wherein detection volume 38 is considerably larger (more than 20 times larger) than the three-dimensional imaging volume 68 of ultrasound probe 16 depicted in FIG. 5A.

Figure 6A:
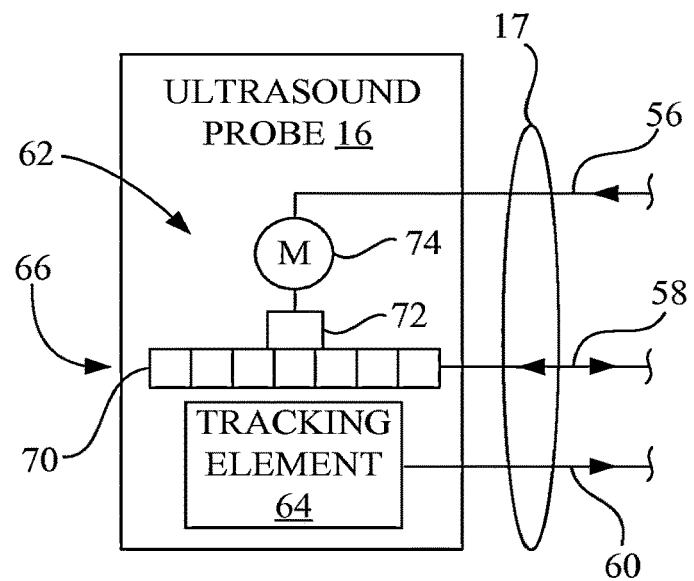
FIG. 6A is a block diagram of an embodiment of the ultrasound probe of FIG. 1, having a movable one-dimensional transducer array.
Figure 6B:
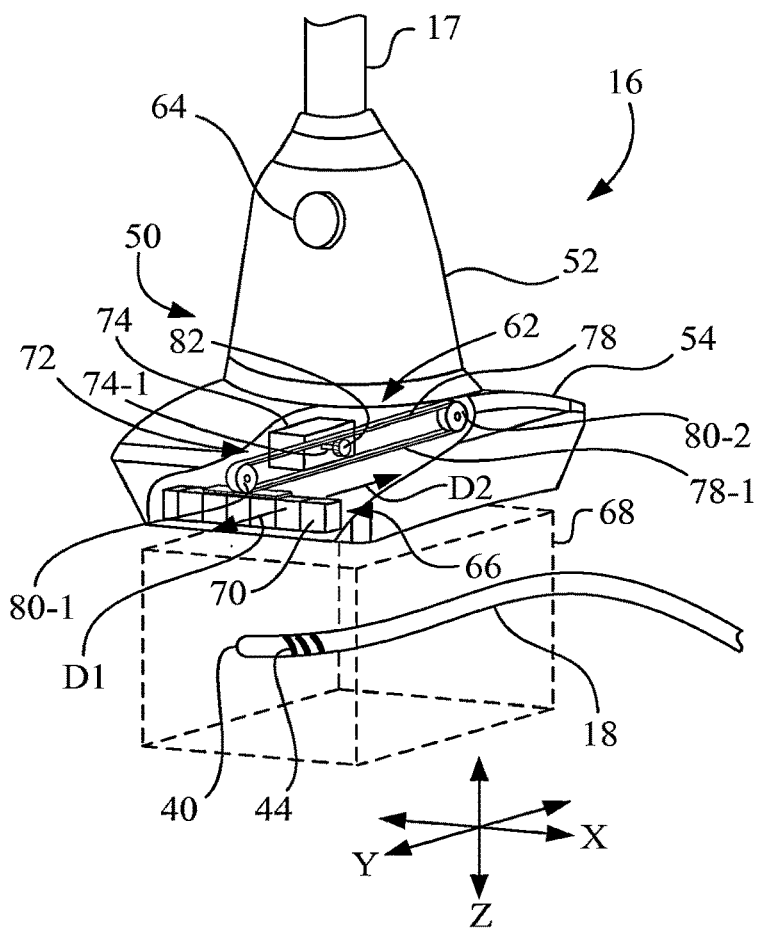
FIG. 6B shows the ultrasound probe of FIGS. 1 and 6A, with a portion broken away to expose an ultrasound transducer mechanism having a movable one-dimensional transducer array, a carriage, and a stepper motor.
Figure 7A:
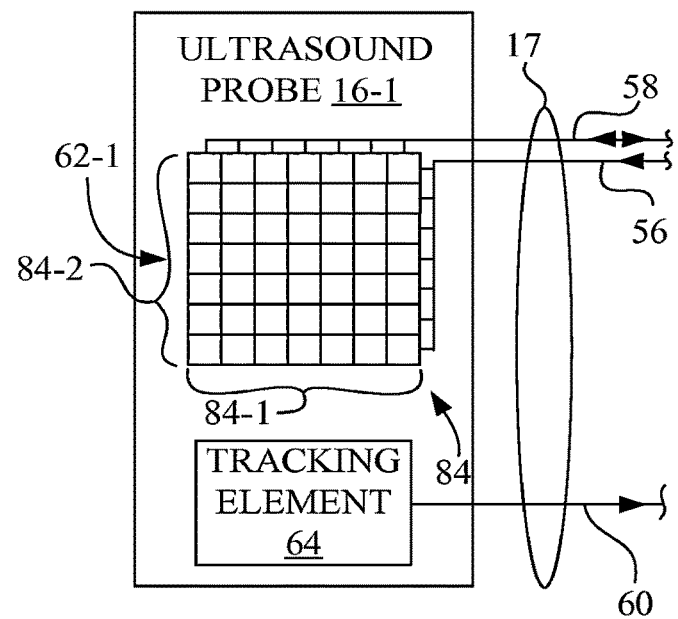
FIG. 7A is a block diagram of another embodiment of the ultrasound probe of FIG. 1, having a stationary two-dimensional transducer array.
Figure 7B:
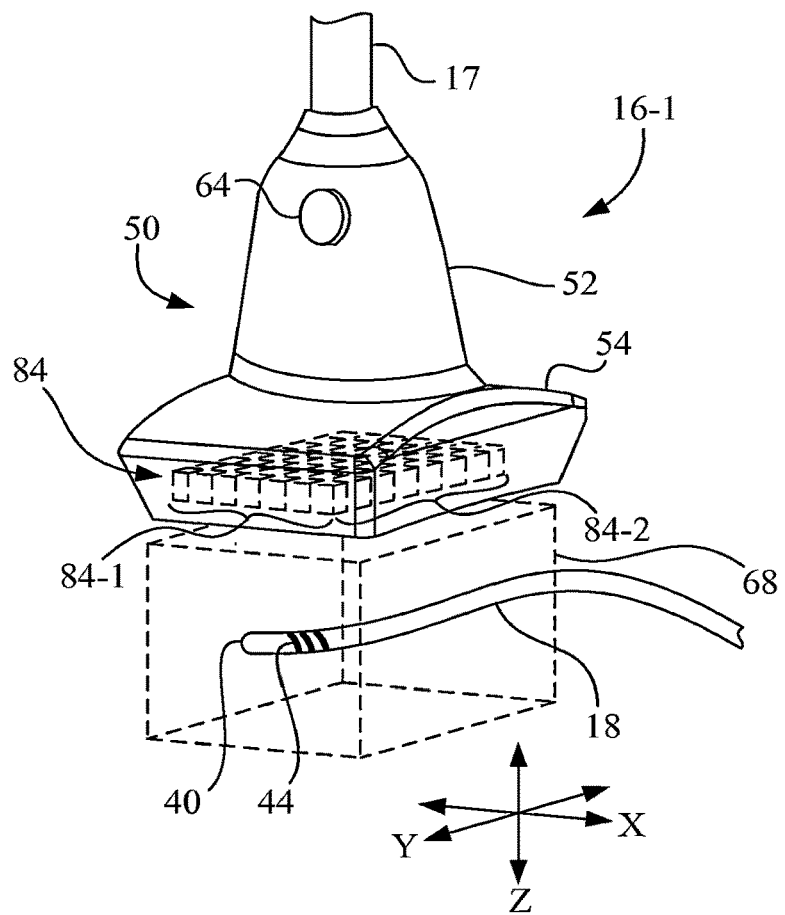
FIG. 7B shows the ultrasound probe of FIG. 7A, depicting the two-dimensional transducer array in phantom (dashed) lines.

In accordance with the present invention, active ultrasound transducer array 66 of ultrasound transducer mechanism 62 of ultrasound probe 16 may incorporate a movable one-dimensional (1D) transducer array, as in the embodiment depicted in FIGS. 6A and 6B. Alternatively, as depicted in FIGS. 7A and 7B, active ultrasound transducer array 66 of ultrasound transducer mechanism 62 of ultrasound probe 16 may be in the form of a selectable portion of a two-dimensional (2D) matrix transducer array.

In the embodiment depicted in FIGS. 6A and 6B, active ultrasound transducer array 66 is physically movable relative to the probe housing 50, i.e., is dynamically positioned within probe housing 50, in order to capture ultrasound images of locations within the three-dimensional imaging volume 68 (diagrammatically illustrated cube volume, for convenience) beneath ultrasound probe 16.

In the embodiment of FIGS. 6A and 6B, ultrasound transducer mechanism 62 includes a one-dimensional (1D) ultrasound transducer array 70, a carriage 72, and a stepper motor 74. In the present embodiment, one-dimensional ultrasound transducer array 70 serves as the active ultrasound transducer array 66. The one-dimensional ultrasound transducer array 70 has a row of a plurality of discrete ultrasound transducer elements.

Carriage 72 is connected to one-dimensional ultrasound transducer array 70, such that one-dimensional ultrasound transducer array 70 moves in unison with carriage 72. Carriage 72 converts a rotation of a rotatable shaft 74-1 of stepper motor 74 into a linear translation of carriage 72, and in turn, into a linear translation of one-dimensional ultrasound transducer array 70 relative to head portion 54 of probe housing 50, in a determined one of two translation directions D1, D2.

Stepper motor 74 is operably connected (electrically and communicatively) to probe position control circuit 31 (see FIG. 2) via communication link 56 of electrical cable 17. In the present embodiment, probe position control circuit 31 is in the form of a motor control circuit, which converts the digital positioning signal supplied by processor circuit 24 into a stepper motor positioning signal, which may include multiple stepper motor control signals, and which are supplied by motor control circuit 76 to stepper motor 74 to command rotation of rotatable shaft 74-1 by an amount corresponding to the amount and position dictated by the digital positioning signal. In the present embodiment, the digital positioning signal and the stepper motor positioning signal may be referred to herein collectively as the "positioning signal", since the stepper motor positioning signal is a form change of the digital positioning signal, and the "positioning signal" is considered herein to have been generated by processor circuit 24.

Carriage 72 converts the rotation of rotatable shaft 74-1 of stepper motor 74 into a linear translation of carriage 72, and in turn, moves one-dimensional ultrasound transducer array 70 relative to head portion 54 of probe housing 50 in a determined one of two translation directions D1, D2, to a location thus dictated by the digital positioning signal generated by processor circuit 24. Thus, based on the positioning signal initiated by processor circuit 24, the one-dimensional ultrasound transducer array 70 may be moved to a desired position relative to head portion 54 of probe housing 50.

FIG. 6B shows an embodiment of carriage 72, wherein carriage 72 has an endless toothed belt 78 suspended between two longitudinally spaced idler gears/pulleys 80-1, 80-2. Rotatable shaft 74-1 of stepper motor 74 is connected to a drive gear 82. Drive gear 82 is drivably engaged with the teeth of endless toothed belt 78. One-dimensional ultrasound transducer array 70 is attached to the lower run 78-1 of endless toothed belt 78, and is movable along the longitudinal extent between the two longitudinally spaced idler gears/pulleys 80-1, 80-2. As such, the arrangement of toothed belt 78 suspended between two longitudinally spaced idler gears/pulleys 80-1, 80-2 converts a rotation of the rotatable shaft 74-1 of the stepper motor 74 into a translation of the one-dimensional ultrasound transducer array 70 in a selectable one of the two translation directions D1, D2.

In the alternative embodiment depicted in FIGS. 7A and 7B, and identified as ultrasound probe 16-1, an alternative ultrasound transducer mechanism 62-1 includes a two-dimensional (2D) ultrasound transducer array 84, and probe position control circuit 31 (see FIG. 2) is in the form of a matrix address circuit of the type used in addressing electronic memory. Two-dimensional ultrasound transducer array 84 has a plurality of columns 84-1 and a plurality of addressable rows 84-2 of discrete ultrasound transducer elements arranged in a matrix pattern. The two-dimensional ultrasound transducer array 84 may be a planar transducer arrangement, or alternatively may be a concave or convex arrangement. Two-dimensional ultrasound transducer array 84 is communicatively coupled to processor circuit 24 via communications link 58 to supply two-dimensional ultrasound data from two-dimensional ultrasound transducer array 84 to processor circuit 24.

In the embodiment of FIGS. 7A, 7B, with reference to FIG. 2, probe position control circuit 31 is electrically connected to processor circuit 24 to receive the digital positioning signal generated by processor circuit 24. In the present embodiment, probe position control circuit 31 operates as a matrix address circuit to convert the digital positioning signal supplied by processor circuit 24 into a row selection positioning signal which is supplied to two-dimensional (2D) ultrasound transducer array 84 via communications link 56 to dynamically select one row of the plurality of rows 84-2 of discrete ultrasound transducer elements as the active linear ultrasound transducer array 66. Thus, the row selection positioning signal corresponds to the position dictated by the digital positioning signal generated by processor circuit 24.

In the embodiment of FIGS. 7A and 7B, since the row selection positioning signal is a form change of the digital positioning signal, the digital positioning signal and the row selection positioning signal may be referred to herein collectively as the "positioning signal", and the "positioning signal" is considered herein to have been generated by processor circuit 24.

As such, the embodiment of FIGS. 7A and 7B emulates the dynamic positioning of the one-dimensional ultrasound transducer array 70 discussed above with respect to FIGS. 6A and 6B, and allows for similar control of where the ultrasound probe will image within the three-dimensional imaging volume 68 beneath the ultrasound probe (see FIG. 5A).

In accordance with the present invention, and in view of the embodiments discussed above, ultrasound imaging system 10 provides a "lock-on" functionality, wherein the position of each of the ultrasound probe 16 and interventional medical device 18 are tracked, and the active ultrasound transducer array 66 in ultrasound probe 16 is dynamically positioned at a convergence of the tracking information, which is further described with reference to the flowchart of FIG. 8. Recall that processor circuit 24 is communicatively coupled to each of the tracking element 44 of interventional medical device 18, tracking element 64 of ultrasound probe 16, ultrasound transducer mechanism 62 of ultrasound probe 16, and to the graphical user interface 22 having display screen 28.

Figure 8:
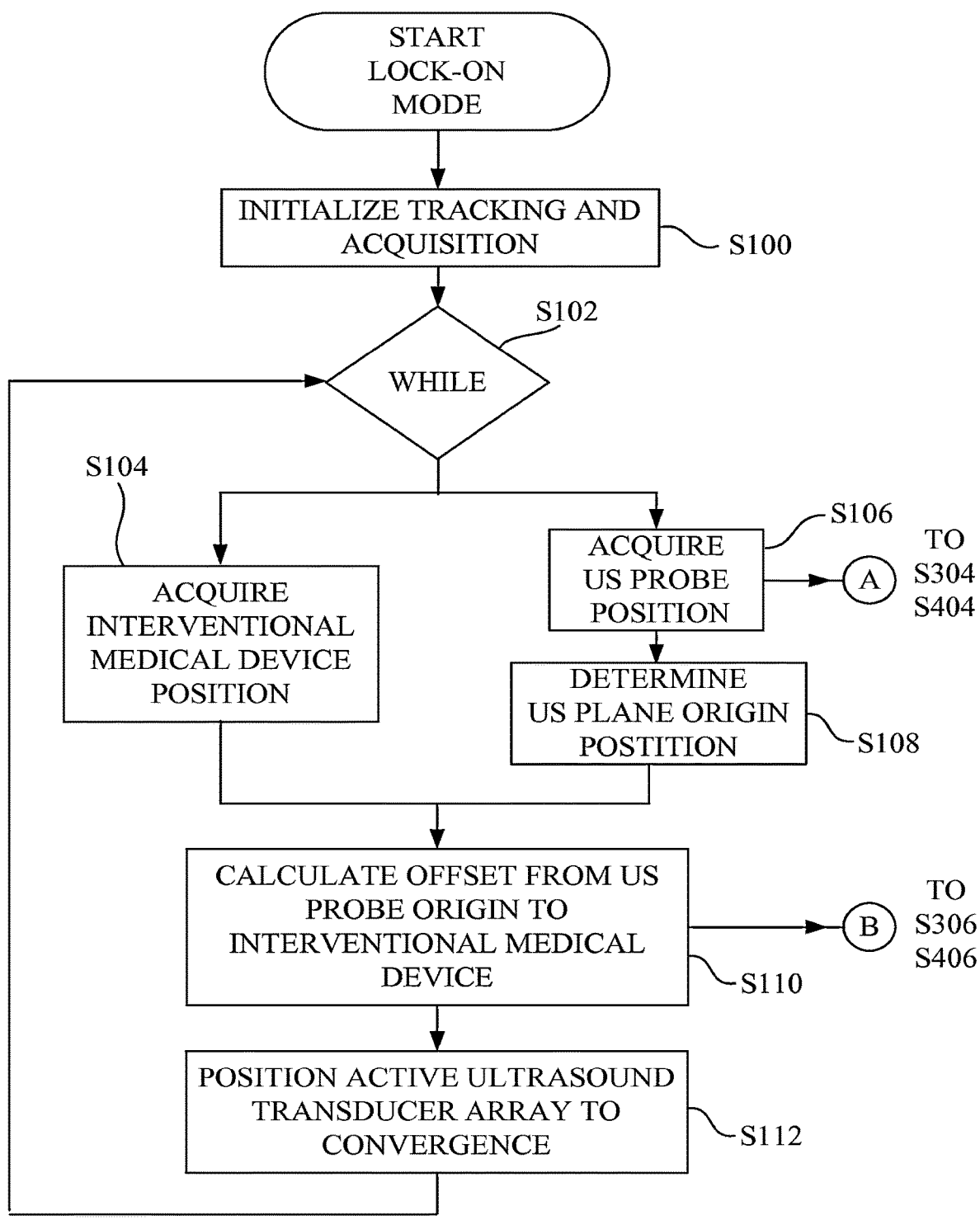
FIG. 8 is a flowchart depicting a lock-on tracking mode in accordance with an aspect of the present invention.

Referring to FIG. 8, at step S100, the tracking and data acquisition aspects of ultrasound imaging system 10 are initialized. In particular, processor circuit 24 executes program instructions to determine the type of tracking elements that are associated with each of ultrasound probe 16 and interventional medical device 18, the communications rate between processor circuit 24 and each of ultrasound probe 16 and interventional medical device 18, the rate of data acquisition updating, and probe parameters. Such probe parameters may include, scan extent start point and end point, and the desired velocity of the movement of active ultrasound transducer array 66, with respect to the origin point 71 (see FIG. 5A), defining the 0, 0, 0 location in the X, Y, and Z axes. Also, the location of tracking elements of ultrasound probe 16 and interventional medical device 18 may be calibrated with respect to the 3D detection volume 38 defined by EM field generator 12 (see FIG. 1).

At step S102, "WHILE" defines the entry into a continuous loop to virtually converge the position of the ultrasound imaging plane of active ultrasound transducer array 66 of ultrasound probe 16 with the position of tracking element 44, and in turn distal tip 40, of interventional medical device 18. Processor circuit 24 remains in this continuous loop until the program execution is stopped.

At step S104, the current position of tracking element 44 of interventional medical device 18 is determined in relation to the 3D detection volume 38 defined by EM field generator 12. In particular, tracking element 44 of interventional medical device 18, generates tip location data as physical coordinates based on the EM locator field 36 generated by EM field generator 12, and provides the tip location data associated with the physical coordinates to processor circuit 24.

At step S106, in parallel to step S104, the current position of tracking element 64 of ultrasound (US) probe 16 is determined in relation to the 3D detection volume 38 defined by EM field generator 12. In particular, tracking element 64 of ultrasound probe 16 generates probe location data as physical coordinates based on the EM locator field 36 generated by EM field generator 12, and provides the probe location data associated with the physical coordinates to processor circuit 24.

At step S108, an ultrasound plane position (B-scan position) is determined based on the probe location data. In particular, processor circuit 24 executes program instructions to define a unit vector, i.e., the Z-axis at origin point 71 (0,0,0) of FIG. 5A, that is perpendicular to (e.g., points downwardly from) the surface of head portion 54 of ultrasound probe 16, wherein the unit vector initially lies on a current ultrasound image plane. Processor circuit 24 executes program instructions to virtually rotate the vector to be normal to the current ultrasound image plane. Processor circuit 24 then executes program instructions to rotate the normal vector about the Z-axis using the probe location data acquired at step S106, which corresponds to the orientation angle of ultrasound probe 16. Processor circuit 24 then executes program instructions to determine the position of the current ultrasound image plane, with respect to the origin, using the following equation:

Equation 1: ultrasound plane position=$(Ax+By+Cz+D)$, where A, B, C are coefficients of the x, y, z position coordinates (of the probe location data) defining the plane of ultrasound probe 16, and D is the length of the distance vector from the origin point 71 to the Ax+By+Cz plane.

At step S110, processor circuit 24 executes program instructions to calculate an offset distance between the position of interventional medical device 18, as defined by the tip location data, and the ultrasound plane position (determined at step S108) of ultrasound probe 16, by using the equation:

Equation 2: OFFSET=$(Ax1+By1+Cz1+D)/\sqrt{A^2+B^2+C^2}$, where: A, B, C, and D are coefficients of the ultrasound plane position (see step S108), and x1, y1, z1 are the position coordinates (of the tip location data) of interventional medical device 18.

The Equation 2 offset calculation gives the minimum, or perpendicular, distance from tracking element 44 of interventional medical device 18 to the ultrasound plane position, which is the distance (and direction) that ultrasound transducer mechanism 62 needs to move active ultrasound transducer array 66 so that there is a convergence (intersection) of the ultrasound position plane with the tracking element 44, and in turn distal tip 40, of interventional medical device 18. Thus, in essence, the calculation determines the offset used to achieve a convergence of the tip location data with the ultrasound plane position associated with the probe location data.

At step S112, ultrasound transducer mechanism 62 is driven to position active ultrasound transducer array 66 at the determined point of convergence as defined by the OFFSET calculated at step S110. In particular, processor circuit 24 executes program instructions to process the OFFSET to generate the positioning signal corresponding to the point of convergence, and the positioning signal is communicatively coupled to ultrasound transducer mechanism 62 to dynamically position active ultrasound transducer array 66 at a desired imaging location of the plurality of discrete imaging locations, so that the two-dimensional ultrasound slice data captured by active ultrasound transducer array 66 includes an image of at least the distal tip 40 of interventional medical device 18, so long as distal tip 40 of the interventional medical device 18 remains in the three-dimensional imaging volume 68 under the surface of the head portion of ultrasound probe 16.

In the embodiment of FIGS. 6A and 6B, the positioning signal will culminate in stepper motor control signal that are supplied to stepper motor 74. In the embodiment of FIGS. 7A and 7B, the positioning signal will culminate in a row selection signal supplied to two-dimensional ultrasound transducer array 84. As used herein, the terms "under" or "underlying" with respect to ultrasound probe 16, means within the possible imaging view extent of ultrasound probe 16.

Thereafter, the process returns to step S102, "WHILE", to continue in the continuous loop in maintaining a convergence of the position of the active ultrasound transducer array 66 of ultrasound probe 16 with tracking element 44, and in turn distal tip 40, of interventional medical device 18.

Figure 9:
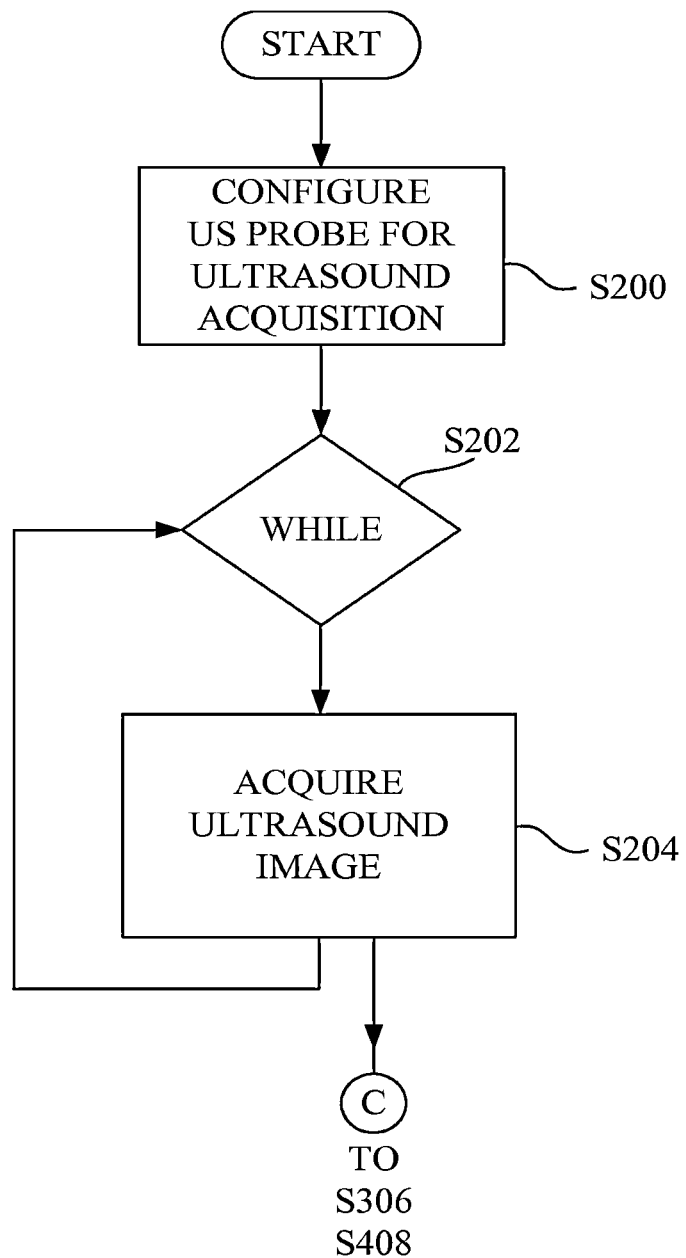
FIG. 9 is a flowchart depicting ultrasound data acquisition in accordance with an aspect of the present invention.

Referring to FIG. 9, there is shown a flowchart describing the acquisition of ultrasound data concurrently with, i.e., during, the "lock-on" function described above with respect to FIG. 8.

At step S200, ultrasound probe 16 is configured for acquisition of ultrasound data. For example, parameters such as the desired resolution, and emission strength of active ultrasound transducer array 66 to achieve a desired depth of penetration, may be set. For two-dimensional image scanning, ultrasound imaging system 10 is configured to collect a series of two-dimensional ultrasound imaging slices (ultrasound B-scan) data. For volume scan imaging, ultrasound imaging system 10 is configured to collect a series of ultrasound B-scan data to form three-dimensional ultrasound volumetric data representing the three-dimensional imaging volume 68, from which C-scan data, or other plane oriented data, may be derived.

At step S202, "WHILE" defines the entry into a continuous loop for acquisition of ultrasound data with active ultrasound transducer array 66 of ultrasound probe 16.

At step S204, ultrasound image data is acquired. More particularly, with reference to FIGS. 2 and 5A, processor circuit 24 is configured to execute program instructions, or alternatively includes circuitry, to process two-dimensional ultrasound slice data generated by the active ultrasound transducer array 66 of ultrasound transducer mechanism 62 of ultrasound probe 16, and to generate the ultrasound image for display at display screen 28 of graphical user interface 22. Also, processor circuit 24 may execute program instructions to automatically store the two-dimensional ultrasound slice data in non-transitory electronic memory 24-2, and thus accumulate multiple image data sets of the location of interest. Alternatively, graphical user interface 22 may provide a user command to processor circuit 24 to store the two-dimensional ultrasound slice data in non-transitory electronic memory 24-2 on demand at the command from a user.

For two-dimensional image scanning, a series of two-dimensional ultrasound imaging slices (ultrasound B-scan) data is collected and stored in non-transitory electronic memory 24-2. For volume scan imaging, active ultrasound transducer array 66 is scanned along the Y-axis across all, or a selected portion, of the three-dimensional imaging volume 68 to take a detailed volumetric scan of the underlying area beneath head portion 54 of ultrasound probe 16, such that a series of ultrasound B-scan data representing the three-dimensional imaging volume is collected and stored in non-transitory electronic memory 24-2.

Thereafter, the process returns to step S202, "WHILE", to continue in the acquisition and updating of the ultrasound data.

While relative movement of ultrasound probe 16 and the distal tip 40 of interventional medical device 18 will result in a movement of the location of distal tip 40 of interventional medical device 18 in the three-dimensional imaging volume 68, so long as tracking element 44 and thus distal tip 40 of interventional medical device 18 remains in the three-dimensional imaging volume 68 of ultrasound probe 16, ultrasound imaging system 10 is able to dynamically position active ultrasound transducer array 66 to converge at a desired imaging location of the plurality of discrete imaging locations in the three-dimensional imaging volume 68 so that the two-dimensional ultrasound slice data includes an image of at least the distal tip 40 of interventional medical device 18 in generating the ultrasound image displayed on display screen 28.

However, referring again to FIG. 5A, in the event that tracking element 44 of interventional medical device 18 is outside the three-dimensional imaging volume 68, a motion indicator 88 located on at least one of the ultrasound probe 16 and the display screen 28 of graphical user interface 22 (see also FIG. 2) is provided to guide the user to an acceptable placement of ultrasound probe 16 relative to the tracked interventional medical device 18. Motion indicator 88 is operably coupled to processor 24, and may be in the form of directional arrows that may be selectively illuminated by processor circuit 24 so as to guide the user to an acceptable placement of ultrasound probe 16 relative to the tracked interventional medical device 18.

In particular, based on the tip location data provided by tracking element 44 of interventional medical device 18 and the probe location data tracking element 64 of ultrasound probe 16 processed by processor circuit 24, processor circuit 24 executes program logic to determine whether tracking element 44 of interventional medical device 18 is outside the three-dimensional imaging volume 68, and thus is outside the imageable range of ultrasound probe 16.

For example, when ultrasound probe 16 having tracking element 64 and interventional medical device 18 having tracking element 44 are placed within detection volume 38 of the EM field generator 12, the location of both tracking element 44 and tracking element 64, and the relative distance between tracking element 44 and tracking element 64, are calculated by processor circuit 24. Using this location and distance information, processor circuit 24 executes program instructions to determine whether the distal tip 40 of the interventional medical device 18 is presently located outside the three-dimensional imaging volume 68. If so, processor circuit 24 of ultrasound imaging system 10 further executes program instructions to generate a visual prompt at motion indicator 88 to prompt the user to move head portion 54 of ultrasound probe 16 in a particular direction to a general location such that tracking element 44, and thus distal tip 40, of interventional medical device 18 resides in the three-dimensional imaging volume 68 under ultrasound probe 16, thereby permitting the active ultrasound transducer array 66 of ultrasound probe 16 to automatically capture ultrasound image data containing the tracking element 44 and distal tip 40 of interventional medical device 18 for display on display screen 28.

Thus, in practicing the "lock-on" functionality mode of action of the present invention, if the tracking element 44, and thus distal tip 40, of the interventional medical device 18 is outside the three-dimensional imaging volume 68 of ultrasound probe 16, manual probe positioning prompts will be generated, in the form of motion indicator 88, which is present on ultrasound probe 16 and/or on graphical user interface 22 to prompt the user to move ultrasound probe 16 to the general location that contains the interventional medical device 18 having tracking element 44, such that tracking element 44 and distal tip 40 of interventional medical device 18 lies within the three-dimensional imaging volume 68 of ultrasound probe 16. As interventional medical device 18 traverses the three-dimensional imaging volume 68, the user may operate graphical user interface 22 to store a reference location, i.e., a seed point, in memory 24-2 at each of one or more particular regions of interest within the three-dimensional imaging volume 68, so as to facilitate a quick and accurate return to a marked location within the three-dimensional imaging volume 68. Because the location of distal tip 40 of interventional medical device 18 is known within the physical environment, a specific location may be designated via its coordinates within ultrasound imaging system 10. A visual marker indicating this location may also be displayed to the user within the 3D virtual environment, and persist on display screen 28 for a period of time designated by the user at graphical user interface 22. These markers may be used to denote clinically relevant locations that the user may return to during a vascular procedure.

Once the user has placed ultrasound probe 16 over the general area to be visualized, location information from ultrasound probe 16 and interventional medical device 18 is further used to move the position of the active ultrasound transducer array 66 of ultrasound probe 16, which allows ultrasound imaging system 10 to converge on a two-dimensional ultrasound image slice that includes the underlying interventional medical device 18, even if ultrasound probe 16 is not placed directly over tracking element 44/distal tip 40 of interventional medical device 18. If desired, a linear offset may be selected at graphical user interface 22 to shift the location of convergence along the length of the interventional medical device 18, in the event that the desired ultrasound image slice does not directly coincide with the position of the tracking element 44/distal tip 40. Such an offset may be either proximal or distal to the position of the tracking element 44, and may be in the form of a distance. Also, a rotational offset may be selected at graphical user interface 22 to change a rotational position of the two-dimensional ultrasound image slice relative to a longitudinal axis of interventional medical device 18, and may be in the form of an angular increment.

The position of the active ultrasound transducer array 66 of ultrasound probe 16 is dynamically adjusted in near real time, limited by data acquisition and processing speed, which allows ultrasound imaging system 10 to adapt to small changes in position of ultrasound probe 16, the position of the tracking element 44 of interventional medical device 18, and/or the patient position, such that an ultrasound image of the underlying interventional medical device 18 is maintained within view of ultrasound probe 16.

If the interventional medical device 18 to be imaged moves outside of the possible three-dimensional imaging volume 68 beneath ultrasound probe 16, positioning prompts in the form of motion indicator 88 are again generated and used to prompt the user to move ultrasound probe 16 in a direction that allows ultrasound imaging system 10 to again converge on, and display, an ultrasound image of the underlying interventional medical device 18.

Ultrasound imaging system 10 also may be operated in a three-dimensional (3D) high resolution scan imaging mode, with reference to step S204 of FIG. 9.

In general, with further reference to FIG. 5A, in the three-dimensional (3D) high resolution imaging mode the ultrasound probe 16 is held in a fixed position over an area of interest, and the active ultrasound transducer array 66 is scanned along the Y-axis across all, or a selected portion, of the three-dimensional imaging volume 68 to take a detailed volumetric scan of the underlying area beneath head portion 54 of ultrasound probe 16. Ultrasound probe 16 may be held in the fixed position by the hand of the user. Metadata containing the position location from each two-dimensional slice obtained in the high resolution mode is further used to identify images taken from the same point in space, and subsequently used for image integration processing.

More particularly, in the 3D high resolution imaging mode, processor circuit 24 of ultrasound console 14 is configured to execute program instructions to generate a scanning signal that is supplied to ultrasound transducer mechanism 62 to scan active ultrasound transducer array 66 over at least a portion of the three-dimensional imaging volume 68. The active ultrasound transducer array 66 is repeatedly actuated during the scan to generate a plurality, i.e., a series, of sequential two-dimensional ultrasound slices, which are stored in memory 24-2, and combined to form the 3D ultrasound volumetric data from which a three-dimensional (3D) high resolution ultrasound image is formed and displayed on display screen 28 of graphical user interface 22 (see also FIG. 2).

The quality of the high resolution 3D images may be improved by generating a composite ultrasound image of the location of interest. Because the location of the ultrasound probe 16 is known by processor circuit 24, multiple sets of 2D or 3D, ultrasound images of a particular location in the three-dimensional imaging volume 68 underlying, e.g., perpendicular to, the surface of the head portion 54 of ultrasound probe 16 may be taken, and stored in non-transitory electronic memory 24-2, from which a compound composite ultrasound image may be generated from the multiple sets of 2D, or 3D, ultrasound images by summing together the multiple sets of ultrasound images of the same location.

In particular, processor circuit 24 is configured to execute program instructions to operate the active ultrasound transducer array 66 to generate multiple sets of ultrasound image data that includes metadata corresponding to a particular location, i.e., metadata describing the location of the scan within the three-dimensional volume 68, and save the multiple sets in non-transitory electronic memory 24-2. Processor circuit 24 is further configured to execute program instructions to sum the multiple sets of ultrasound image data to generate composite (compound) ultrasound image data, which is then stored in non-transitory memory 24-2 and/or is displayed on display screen 28 of graphical user interface 22.

Figure 10:
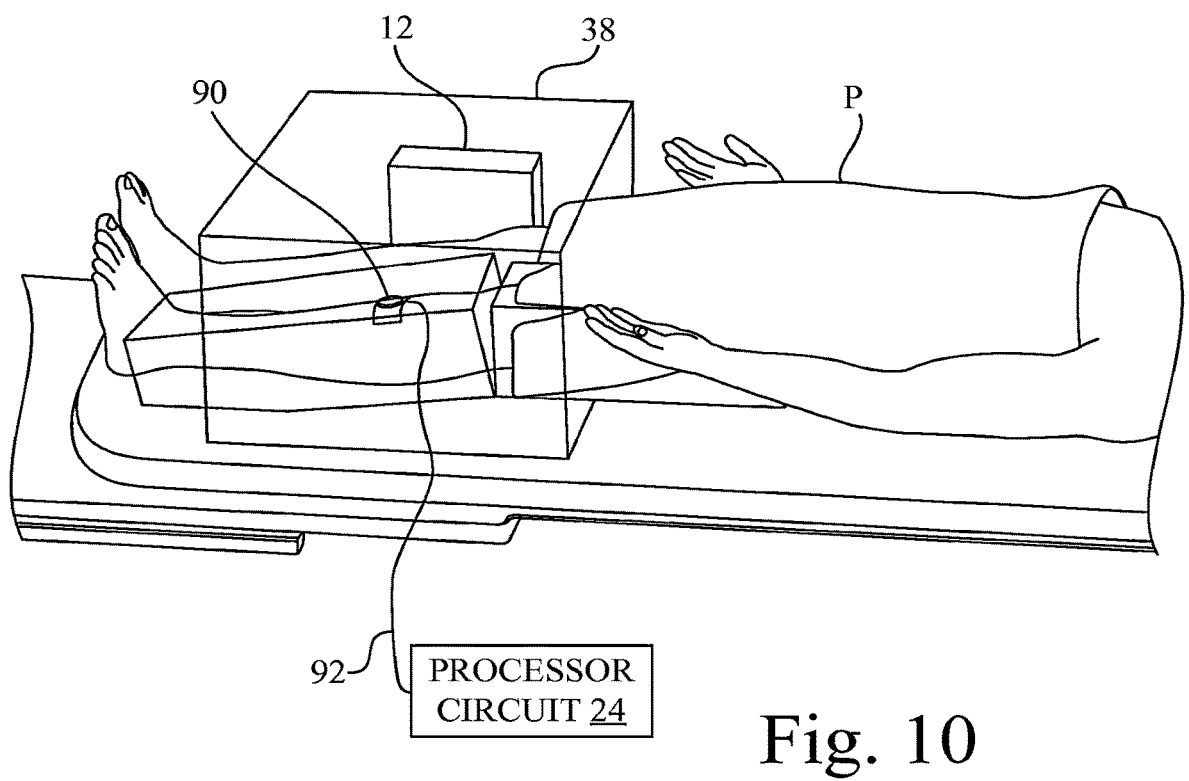
FIG. 10 shows a general side view of a patient having a position tracking element affixed to the skin.

Referring also to FIG. 10, the quality of the high resolution 3D images also may be improved by tracking the position of the patient P in relation to the position of ultrasound probe 16 to reduce motion artifacts in the 3D images. A third EM tracking element 90 (i.e., a wire electrical tracking coil), is affixed to the patient, such as by an adhesive. Tracking element 90 is communicatively coupled to processor circuit 24 of ultrasound console 14 by a communication link 92, such as a wired or wireless connection. Tracking element 90, when energized by electromagnetic (EM) field generator 12, generates three-axis patient location data, which is supplied via communications link 92 to processor circuit 24. Processor circuit 24 processes the three-axis patient location data to further adjust the position of the active ultrasound transducer array 66 of ultrasound probe 16 in response to any motion of the patient. In other words, tracking element 90 allows for the position of the patient to be known, which in turn allows ultrasound imaging system 10 to adjust the position of the active ultrasound transducer array 66 of ultrasound probe 16 to any motion created by the patient.

Ultrasound imaging system 10 also may be operated to render and display one or more synthetic (user chosen) scan planes.

Figure 11:
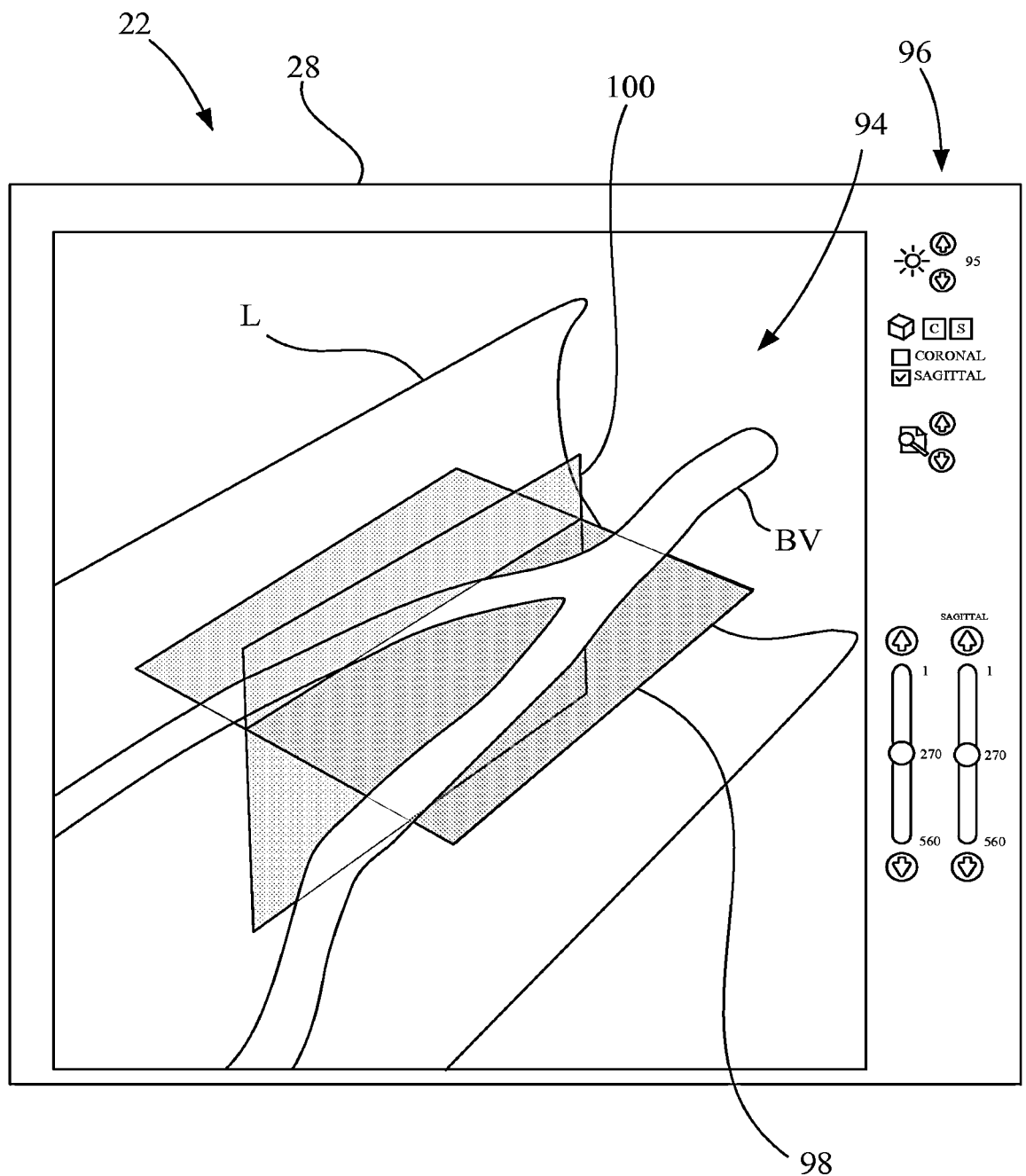
FIG. 11 shows a screen of the graphical user interface of FIG. 1, configured to display one or more synthetic (user chosen) scan planes, such as a coronal scan plane and an axial (sagittal) scan plane.

Referring also to FIG. 11, there is shown the graphical user interface 22 having a three-dimensional ultrasound image 94 and user controls 96 displayed on display screen 28. As described above, a plurality, i.e., a series, of sequential two-dimensional ultrasound slices may be generated and combined to generate 3D ultrasound volumetric data defining a three-dimensional imaging volume. Using the 3D ultrasound volumetric data acquired from ultrasound probe 16, the user may select for rendering and display one or more synthetic (user chosen) scan planes, such as a coronal scan plane 98 and an axial (sagittal) scan plane 100.

In particular, the user may define, using user controls 96, a desired synthetic plane orientation with respect to the 3D ultrasound volumetric data associated with three-dimensional ultrasound image 94. From the plane orientation inputs provided at user controls 96, processor circuit 24 of ultrasound imaging system 10 executes program instructions to identify within the 3D ultrasound volumetric data of three-dimensional ultrasound image 94 the image data associated with the desired synthetic plane orientation. The desired synthetic plane may pass through multiple two-dimensional image data slices in the 3D ultrasound volumetric data. Once the image data associated with the desired synthetic plane orientation within the 3D ultrasound volumetric data is identified, the desired one or more synthetic (user chosen) scan planes may be rendered and displayed on display screen 28 of graphical user interface 22 within the generated three-dimensional ultrasound image 94 as shown in FIG. 11, or as standalone two-dimensional images. These additional views may allow for further inspection of the underlying anatomy, beyond what is normally obtained via fluoroscopy, which in turn may result in improved clinical outcomes.

Various views, such as those associated with the sagittal plane, the transverse plane, and the coronal plane, may be visualized, and a slice from one or more, or all, of the planes, as defined by the location of the tracked device(s), e.g., tracking element 44 of interventional medical device 18 and/or tracking element 64 of ultrasound probe 16, can be displayed, individually or as a group. It is also envisioned that scan planes that do not exist at 90 degrees from each other could also be defined and selected by the user. Additionally, the user defined scan planes may not be planar, and may follow a curved path.

Another aspect of the present invention provides for a focusing of the three-dimensional imaging volume around a determined region of interest, i.e., the region around the location of tracking element 44 of interventional medical device 18, by reducing the scan extent along the Y-axis (see FIG. 5A), thus reducing the amount of three-dimensional ultrasound volumetric data required to adequately view the region surrounding interventional medical device 18. In other words, following an initial 3D ultrasound volumetric data scan, on a subsequent 3D ultrasound volumetric data scan centered on the determined region of interest, the scan extent of active ultrasound transducer array 66 along the Y-axis is reduced, i.e., focused, to that of most interest, thus reducing scanning time and the amount of data required to adequately represent the three-dimensional volume of interest.

In particular, processor circuit 24 executes program instructions to determine a region of interest in the three-dimensional ultrasound volumetric data defining the three-dimensional imaging volume 68. Processor circuit 24 also executes program instructions to reduce the scan range of the active ultrasound transducer array 66 of the ultrasound transducer mechanism 62 along the Y-axis for acquisition of subsequent three-dimensional ultrasound volumetric data at the region of interest from that of the scan range of the previous scan, so as to reduce the amount of acquired three-dimensional ultrasound volumetric data from that of the prior scan.

Figure 12:
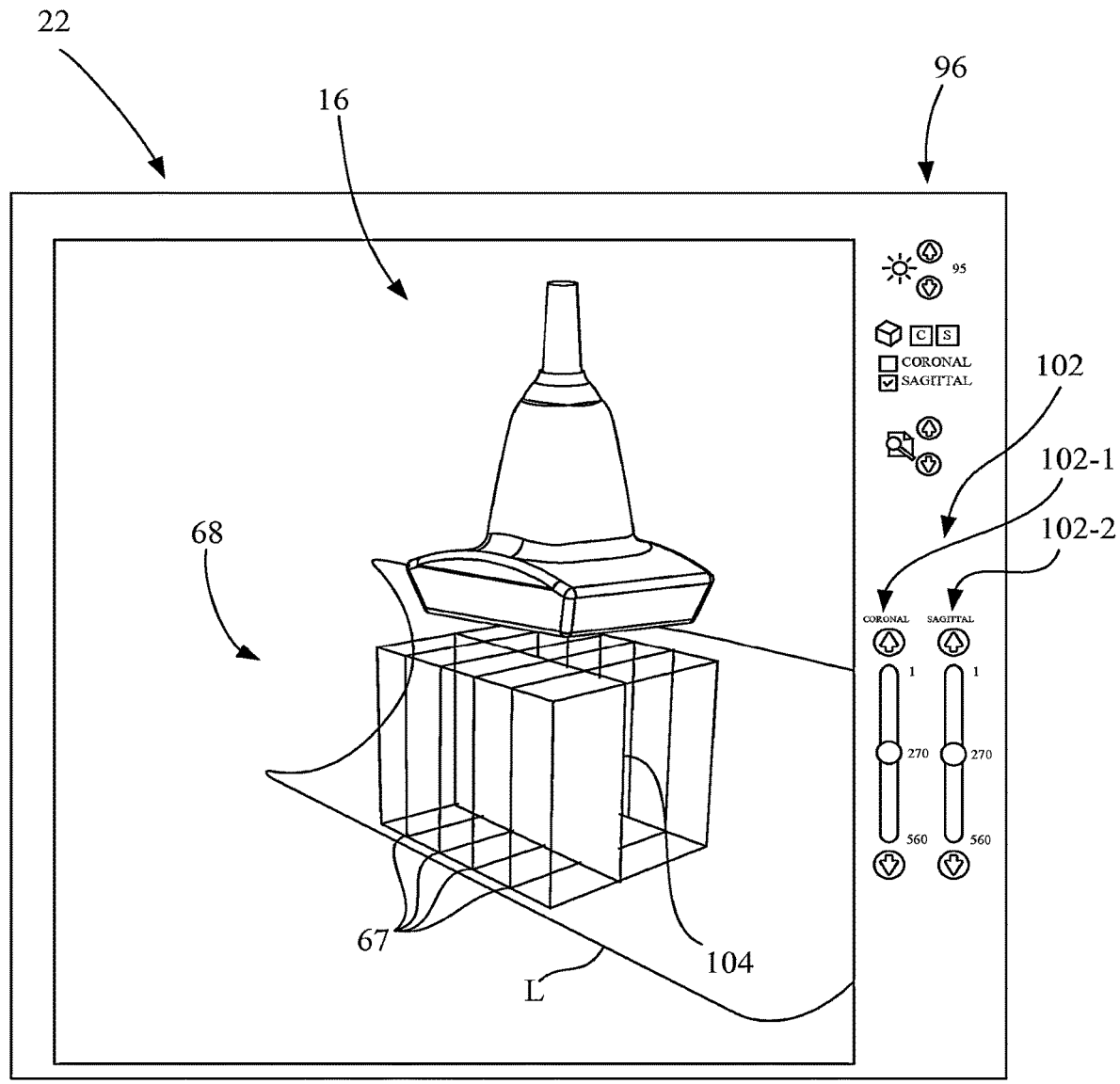
FIG. 12 is a pictorial representation of the graphical user interface of FIG. 1 depicting a sagittal plane slice extending through a series of two-dimensional ultrasound image slices in a three-dimensional imaging volume at sagittal slice location 270.
Figure 13:
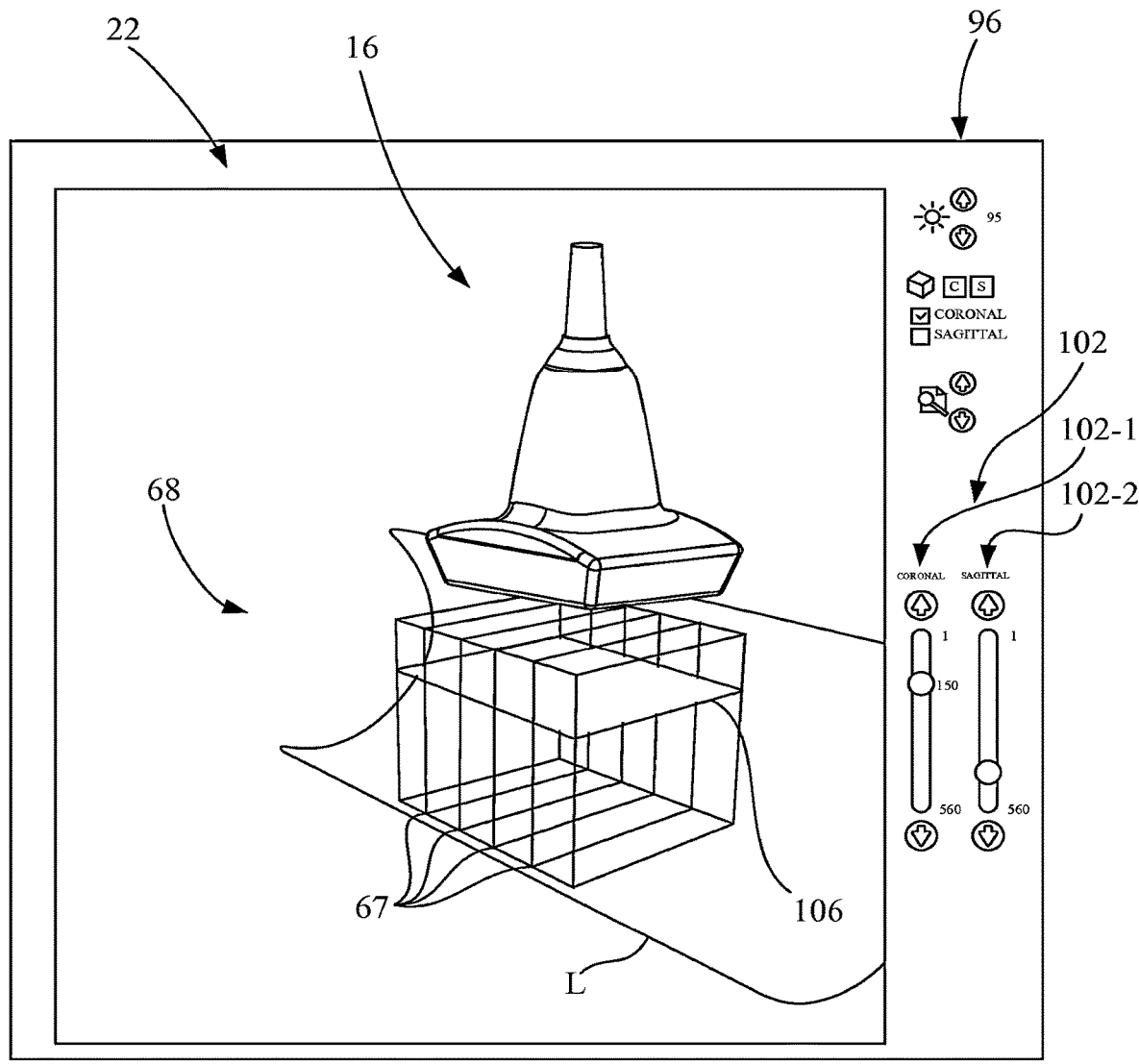
FIG. 13 is a pictorial representation of the graphical user interface of FIG. 1 depicting a coronal plane slice extending through a series of two-dimensional ultrasound image slices in a three-dimensional imaging volume at coronal slice location 150.

Referring to FIGS. 12 and 13, as another aspect of the present invention, user controls 96 of graphical user interface 22 may include one or more slice selection sliders 102, such as a coronal slider 102-1 and a sagittal slider 102-2, to provide a sequential variation from an automatically, or manually, selected two-dimensional ultrasound image slice being displayed.

Referring also to FIG. 5A, a plurality, i.e., a series, of sequential two-dimensional ultrasound B-scan imaging slices 67 may be generated and combined to generate 3D ultrasound volumetric data defining a three-dimensional imaging volume 68. As such, based on tracking of the location of tracking element 44 of interventional medical device 18 and tracking element 64 of ultrasound probe 16, a desired two-dimensional ultrasound image slice on a desired imaging plane may be generated from the 3D ultrasound volumetric data that includes a particular region of interest, such as distal tip 40 of interventional medical device 18. The desired two-dimensional ultrasound image slice may be in an imaging plane different from that of the native B-scan imaging plane of the sequential two-dimensional ultrasound imaging slices 67 that when combined form the 3D ultrasound volumetric data defining the three-dimensional imaging volume 68.

Thus, slice selection sliders 102 permit the user to select a slice in each of one or more imaging planes for display, if desired, wherein the selected two-dimensional ultrasound image slice may intersect, or lie on either side of, the two-dimensional ultrasound image slice that was automatically, or manually, selected. The slice selection sliders 102 are configured to provide a sequential parallel variation from the initially selected two-dimensional ultrasound image slice to manually select a second two-dimensional ultrasound image slice parallel to the initially selected two-dimensional ultrasound image, wherein the second two-dimensional ultrasound image slice lies on either side of the initially selected two-dimensional ultrasound image slice.

For example, FIG. 12 is a pictorial representation at graphical user interface 22 depicting a selection of a sagittal plane slice 104 extending through a series of two-dimensional ultrasound image slices 67 in the three-dimensional imaging volume 68 at sagittal slice location 270. By manipulation of sagittal slider 102-2 using one of the up-down arrows, sagittal slice location 271, or others 1-269 or 272-560, parallel to the sagittal slice location 270 may be selected for display. Likewise, FIG. 13 is a pictorial representation depicting a selection of a coronal plane slice 106 extending through a series of two-dimensional ultrasound image slices 67 in a three-dimensional imaging volume 68 at coronal slice location 150. By manipulation of coronal slider 102-1 using one of the up-down arrows, coronal slice location 151, or others 1-149 or 152-560, may be selected for display.

Figure 14:
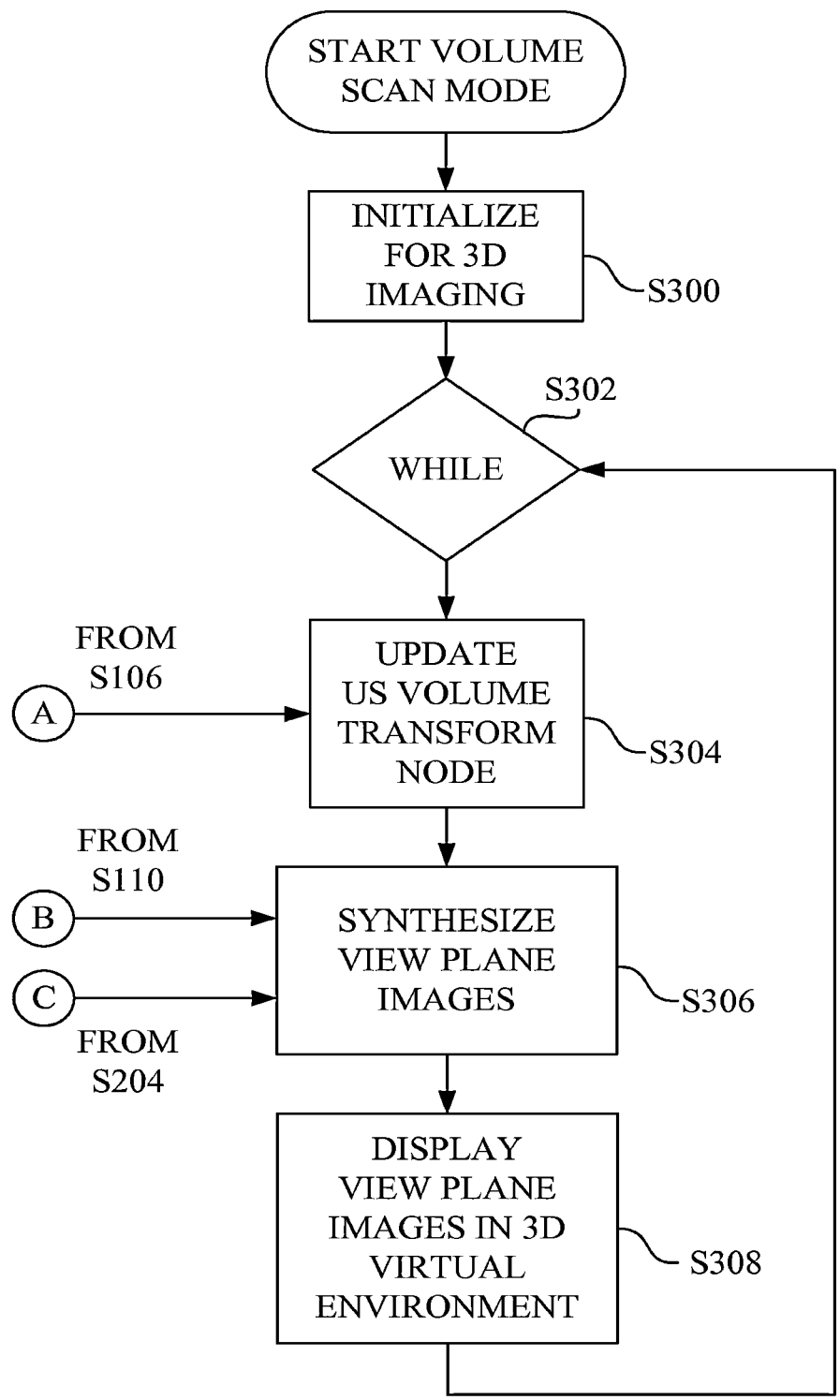
FIG. 14 is a flowchart describing the generation of a set of ultrasound images derived or synthesized from the three-dimensional volume data set, and shown in the correct location in the 3D virtual environment, in accordance with an aspect of the present invention.

Referring to FIG. 14, there is shown a flowchart describing the generation of a 3D ultrasound image as a set of three orthogonal ultrasound images.

At step S300, ultrasound imaging system 10 is initialized for rendering a 3D ultrasound image as a set of three orthogonal images, such as setting up processor circuit 24 and graphical user interface 22 for construction of 3D models.

At step S302, "WHILE" defines the entry into a continuous loop for generation and updating of the displayed 3D ultrasound image.

At step S304, an ultrasound (US) volume transform node is updated based on the position of ultrasound probe 16, as determined at step S106 of FIG. 8. In particular, processor circuit 24 executes program instructions to move the 3D model of the three-dimensional imaging volume 68 to match the current position of ultrasound probe 16.

At step S306, using the calculated OFFSET from step S110 of FIG. 8, and the 3D image data acquisition as described at step S204 of FIG. 9, processor circuit 24 executes program instructions to choose a two-dimensional ultrasound imaging slice 67 (B-scan) from a C-scan data slice that includes the tracking element 44, and in turn the distal tip 40, of interventional medical device 18.

At step S308, processor circuit 24 executes program instructions to generate 3D display data representative of three orthogonal images in a virtual 3D environment associated with the three-dimensional imaging volume 68 matched to the current position of ultrasound probe 16. Processor circuit 24 sends the 3D display data to user interface 22 for display on display screen 28 as three orthogonal images that include the tracking element 44, and in turn the distal tip 40, of interventional medical device 18.

Thereafter, the process returns to step S302, "WHILE", to continue updating the displayed 3D ultrasound image.

Referring now to FIGS. 15A, 15B, 15C and 16, there is described below a patient oriented imaging window mode. In the past, that which was rendered as "up" on the ultrasound display screen followed the orientation of the ultrasound probe. However, in this aspect of the present invention, the orientation of the displayed ultrasound image is true to the orientation of the patient, regardless of the actual orientation of the ultrasound probe.

Figure 15A:
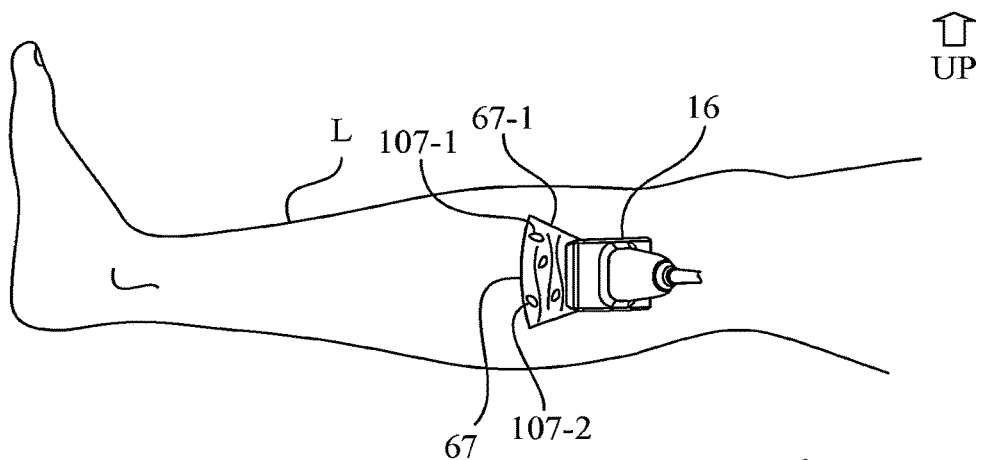
FIG. 15A is a diagrammatic illustration of the ultrasound probe of FIG. 1 taking a two-dimensional ultrasound imaging slice of a portion of a leg of a patient.

FIG. 15A shows a diagrammatic illustration of ultrasound probe 16 taking a two-dimensional ultrasound imaging slice 67 of a portion of a leg L of a patient. For purposes of comparison, note the location and orientation of the upper blood vessel 107-1, and the lower-left blood vessel 107-2, in relation to the orientation of the leg L of a patient P.

Figure 15B:
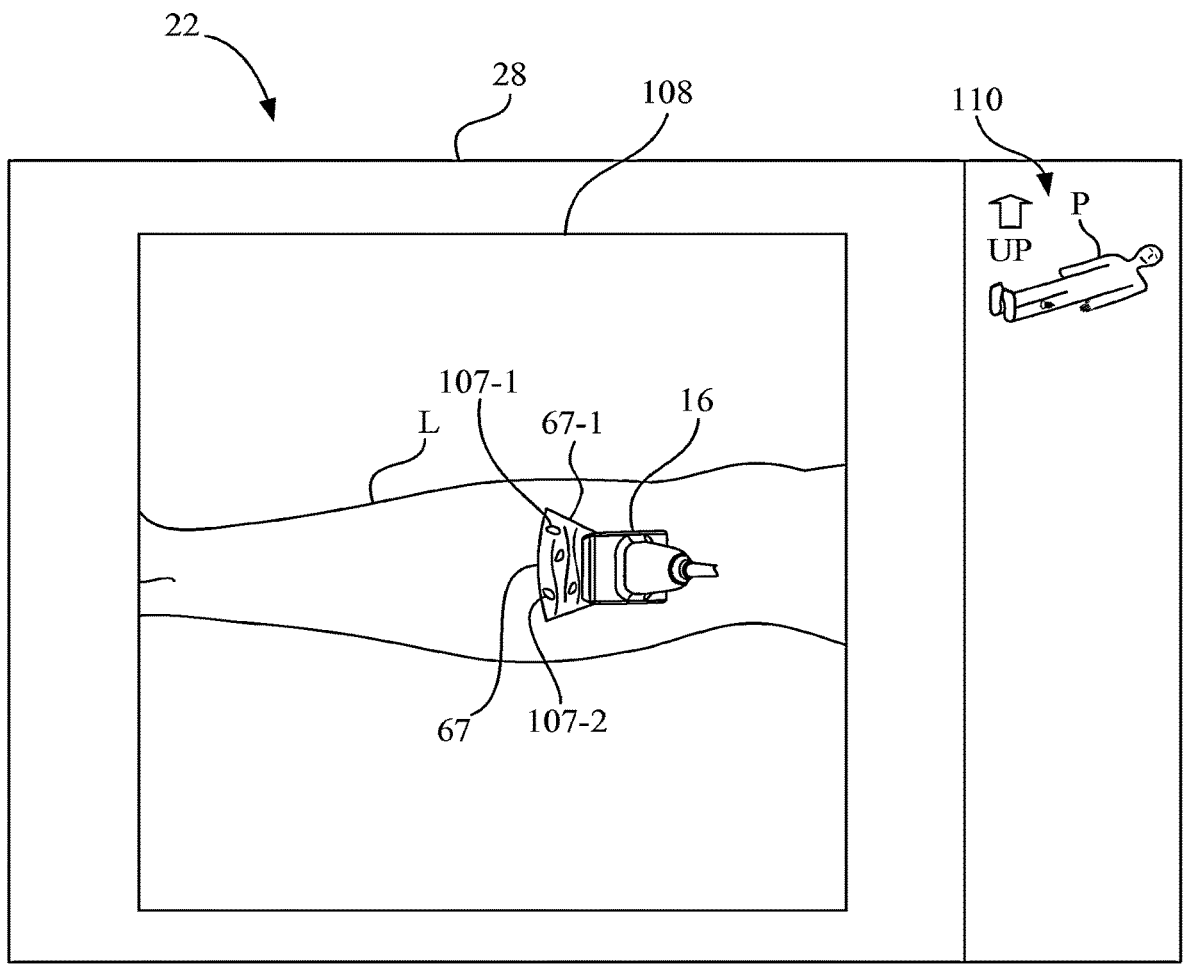
FIG. 15B is a diagrammatic illustration of the graphical user interface of FIG. 1 having a patient oriented imaging window depicting a patient oriented virtual environment, wherein the location and orientation of the acquired ultrasound image data is rendered on the display screen to correspond to the orientation of the patient, such that the orientation and location of where the image is being acquired relative to the patient can be indicated and communicated to the viewer via use of the virtual environment.

FIG. 15B is a diagrammatic illustration of graphical user interface 22 having a patient oriented imaging window 108 depicting a patient oriented virtual environment on display screen 28 of graphical user interface 22, wherein the location and orientation of the acquired ultrasound image data is rendered on the display screen 28 to correspond to the orientation of the patient P, wherein the orientation and location of where the ultrasound image is being acquired relative to a position of the patient P is indicated and communicated to the clinician via use of the virtual environment. In particular, FIG. 15B shows a diagrammatic illustration of graphical user interface 22 having patient oriented imaging window 108 including an image of leg L, rendered as an actual image of patient leg L or as a computer generated virtual rendering, and including a virtual rendering of ultrasound probe 16 and two-dimensional ultrasound imaging slice 67 that is generated by ultrasound probe 16. Also shown is a secondary imaging window 110 including a computer generated virtual rendering, i.e., a graphic, of the orientation of the body of patient P, as well as an UP arrow indicating the orientation of the UP relative to the patient.

Figure 15C:
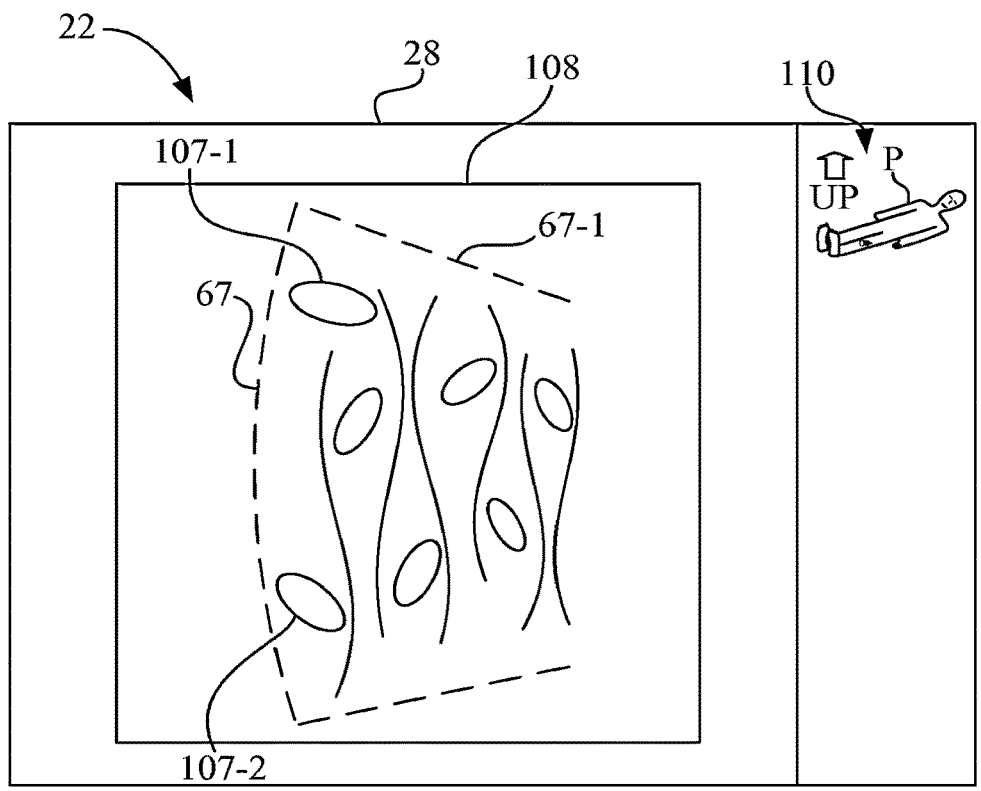
FIG. 15C is a full view of the ultrasound image shown in FIG. 15B, in which the orientation of the location and orientation of the acquired ultrasound image data is rendered on the display screen to correspond to the orientation of the patient.

Referring also to FIG. 15C, since the orientation of ultrasound probe 16 is known to ultrasound imaging system 10, as described above, the display of the ultrasound image on display screen 28 of graphical user interface 22 may be adjusted such that a vertical "top" 67-1 of the acquired ultrasound image data of two-dimensional ultrasound imaging slice 67, or the vertical top of the acquired volumetric data in 3D data acquisition, is always rendered as "UP" on display screen 28 relative to the position of the patient P, and regardless of the actual orientation of ultrasound probe 16 relative to the patient. In other words, even if the actual orientation of ultrasound probe 16 is changed relative to the position of the leg L from that depicted in FIG. 15B, such as the head of ultrasound probe 16 pointing downward, the orientation of the ultrasound image on display screen 28 of graphical user interface 22 remains as depicted in FIG. 15C. Thus, as viewed in display screen 28, features of the displayed image, such as the upper blood vessel 107-1, and the lower-left blood vessel 107-2, are always displayed in the correct orientation relative to the patient P.

Figure 15D:
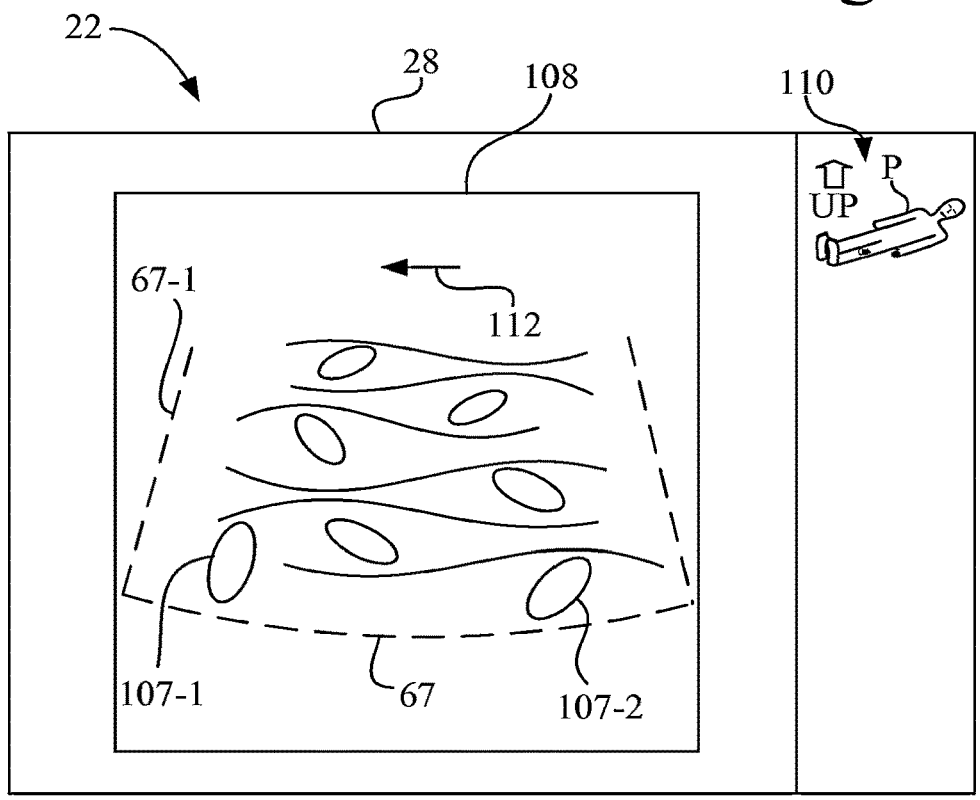
FIG. 15D is a comparative view of the ultrasound image shown in FIG. 15B when rendered in accordance with the prior art, wherein the orientation of the acquired ultrasound image data rendered on the display screen does not correspond to the orientation of the patient.

In comparison, FIG. 15D depicts the ultrasound image generated in FIG. 15A as it would be rendered in accordance with the prior art, wherein the orientation of the acquired ultrasound image data rendered on the display screen does not correspond to the orientation of the patient. This is because in the prior art, the image is rendered on the display screen wherein the ultrasound probe head is in a virtual position at the top of the display screen and the bottom on the display screen always corresponds to the distal extent of the generated ultrasound image. More particularly, with the ultrasound probe oriented as depicted in FIGS. 15A and 15B, the prior art rendered ultrasound image would position the upper blood vessel 107-1 and the lower-left blood vessel 107-2 on the display screen as shown in FIG. 15D (i.e., rotated 90 degrees from that depicted in FIG. 15C), and as such, the displayed image no longer corresponds to the orientation of the patient P. Rather, as shown in FIG. 15D, using arrow 112 to designate the true "up" orientation, the prior art ultrasound image is actually rendered to face toward the left on the display screen. Accordingly, in the prior art, the ultrasound technician was required to mentally associate the orientation of the displayed image with that of the actual orientation of the patient.

Advantageously, the patient oriented imaging window aspect of the present invention described above with respect to FIGS. 15A, 15B and 15C, generates a virtual environment that aids a clinician, including a person not experienced in ultrasound imaging, in successful image acquisition.

Figure 16:
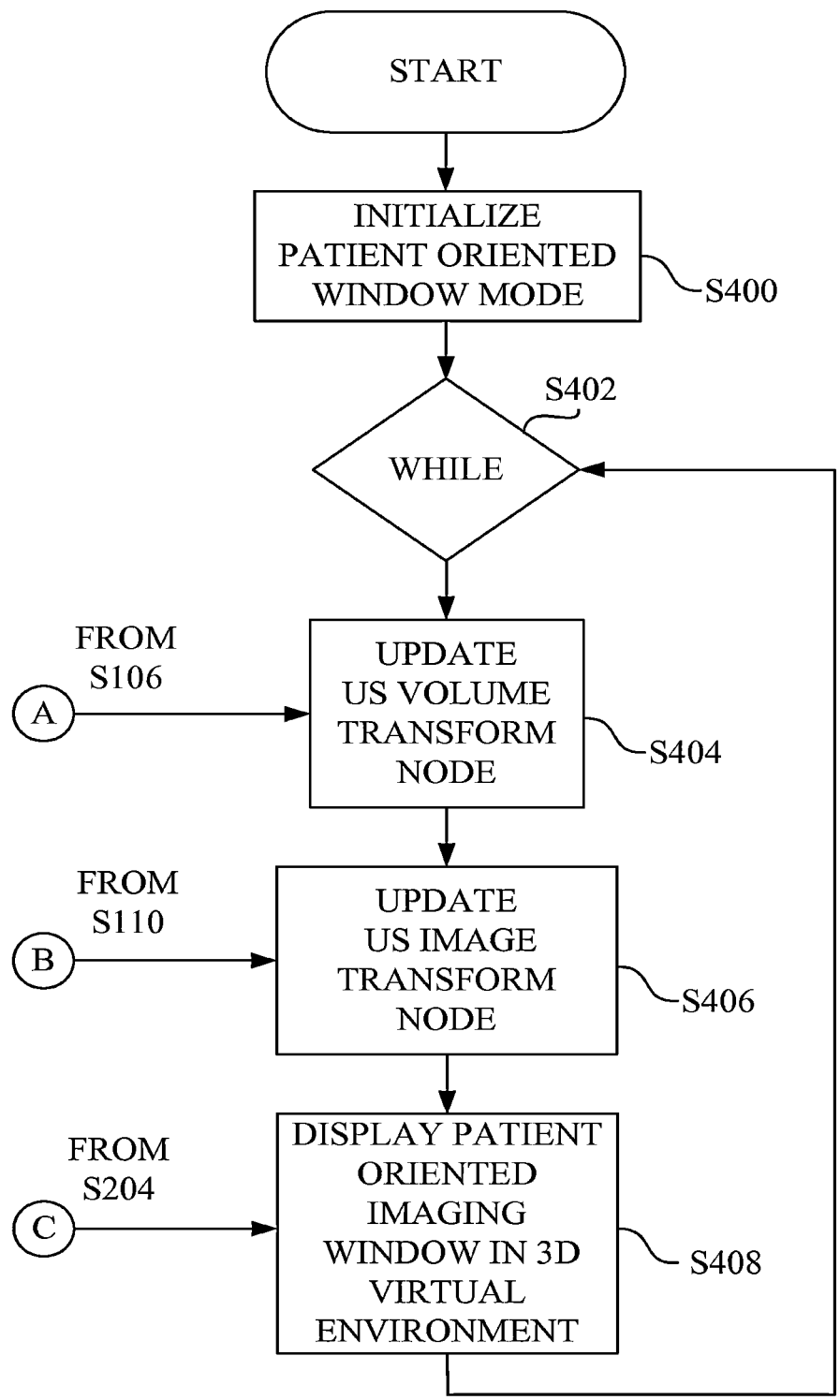
FIG. 16 is a flowchart of a patient oriented imaging window mode, or virtual environment imaging mode, associated with the depiction of the patient oriented imaging window of FIG. 15B shown in the correct location in the 3D virtual environment, in accordance with an aspect of the present invention.

More particularly, FIG. 16 is a flowchart of a patient oriented imaging window mode, i.e., a virtual environment imaging mode, associated with the generation of the patient oriented imaging window as depicted above with respect to FIGS. 15A, 15B and 15C.

At step S400, ultrasound imaging system 10 is initialized for rendering a 3D ultrasound image, such as setting up processor circuit 24 and graphical user interface 22 for construction of 3D models, initializing a camera video data transfer, and configuring appropriate patient lighting for video.

At step 402, "WHILE" defines the entry into a continuous loop for generation and updating of the displayed patient oriented imaging window 108 as depicted in FIGS. 15B and 15C.

At step S404, an ultrasound (US) volume transform node is updated based on the position of ultrasound probe 16, as determined at step S106 of FIG. 8. In particular, processor circuit 24 executes program instructions to move the 3D model of the three-dimensional imaging volume 68 (see FIG. 5A) to match the current position of ultrasound probe 16.

At step S406, an ultrasound (US) image transform node is updated based on the calculated OFFSET from step S110 of FIG. 8. In particular, processor circuit 24 executes program instructions to update the ultrasound image transform node by moving a 3D model of the three-dimensional ultrasound imaging data to match the current two-dimensional ultrasound imaging slice 67 (B-scan) acquired from ultrasound probe 16.

At step 408, based on 2D and/or 3D image data acquisition as described at step S204 of FIG. 9, processor circuit 24 executes program instructions to display the two-dimensional ultrasound imaging slice 67 (B-scan) in a 3-D environment in the patient oriented imaging window 108, such that the vertical "top" 67-1 of the acquired ultrasound image data of two-dimensional ultrasound imaging slice 67, or the vertical top of the acquired volumetric data in 3D data acquisition, is always rendered as "up" on display screen 28 relative to the position of the patient, and regardless of the actual orientation of ultrasound probe 16 relative to the patient.

Thereafter, the process returns to step 402, "WHILE", to continue in updating the patient oriented imaging window 108.

As an additional aspect, since the offset distance (z-axis) between the ultrasound probe 16 and the interventional medical device 18 can be calculated using Equations 1 and 2 (see steps S108 and S110, discussed above), this offset, or depth information, can further be used to dynamically control some of the ultrasound imaging settings in near real time, as identified below. This allows the system to optimize the image quality settings such that the best image of the interventional medical device 18 is displayed to the user at display screen 28. The ultrasound imaging settings that may be dynamically controlled because the z-axis offset from the ultrasound probe 16 can be calculated may include:

1) Ultrasound focus; such that the lateral resolution is optimized at the depth that contains the interventional medical device 18. Using the z-axis offset between the ultrasound probe 16 and the interventional medical device 18, the focus can be automatically adjusted to the depth that contains the interventional medical device 18.
2) Depth setting; because the z-axis offset from the ultrasound probe 16 can be calculated, the Depth setting can be dynamically controlled such that the depth of imaging is automatically adjusted to match the depth of the interventional medical device 18.
3) Zoom; because the z-axis offset from the ultrasound probe 16 can be calculated, the imaging window can be "zoomed" such that a larger view of the area of interest may be automatically displayed to the user.
4) Doppler flow window; because the z-axis offset from the ultrasound probe 16 can be calculated, a Doppler flow calculation window can be targeted to only include the area of interest that contains interventional medical device 18.

In accordance with another aspect of the invention, referring again to FIG. 1, since the location of ultrasound probe 16 is known within the detection volume 38, multiple 2D ultrasound, e.g., B-mode, image slices acquired from different points within the detection volume 38 may be integrated into a larger volumetric stack of images. These images may then be combined to display ultrasound images that represent a composite of multiple 2D ultrasound image slices taken at different time periods. For example, if the location of ultrasound probe 16 and distal tip 40 of interventional medical device 18 is known, the following steps may be taken to extract an extended image that exceeds the length of one 2D ultrasound image: collect a spherical amount of data at a preselected radii from distal tip 40 of interventional medical device 18 as interventional medical device 18 is advanced through a vasculature lumen; store a radial data set corresponding to the spherical amount of data to memory 24-2 as interventional medical device 18 is advanced through the vasculature lumen; and, from the stored radial data set, construct virtual scan planes that produce a virtual scan plane that exists along the length of the interventional medical device 18.

Figure 17:
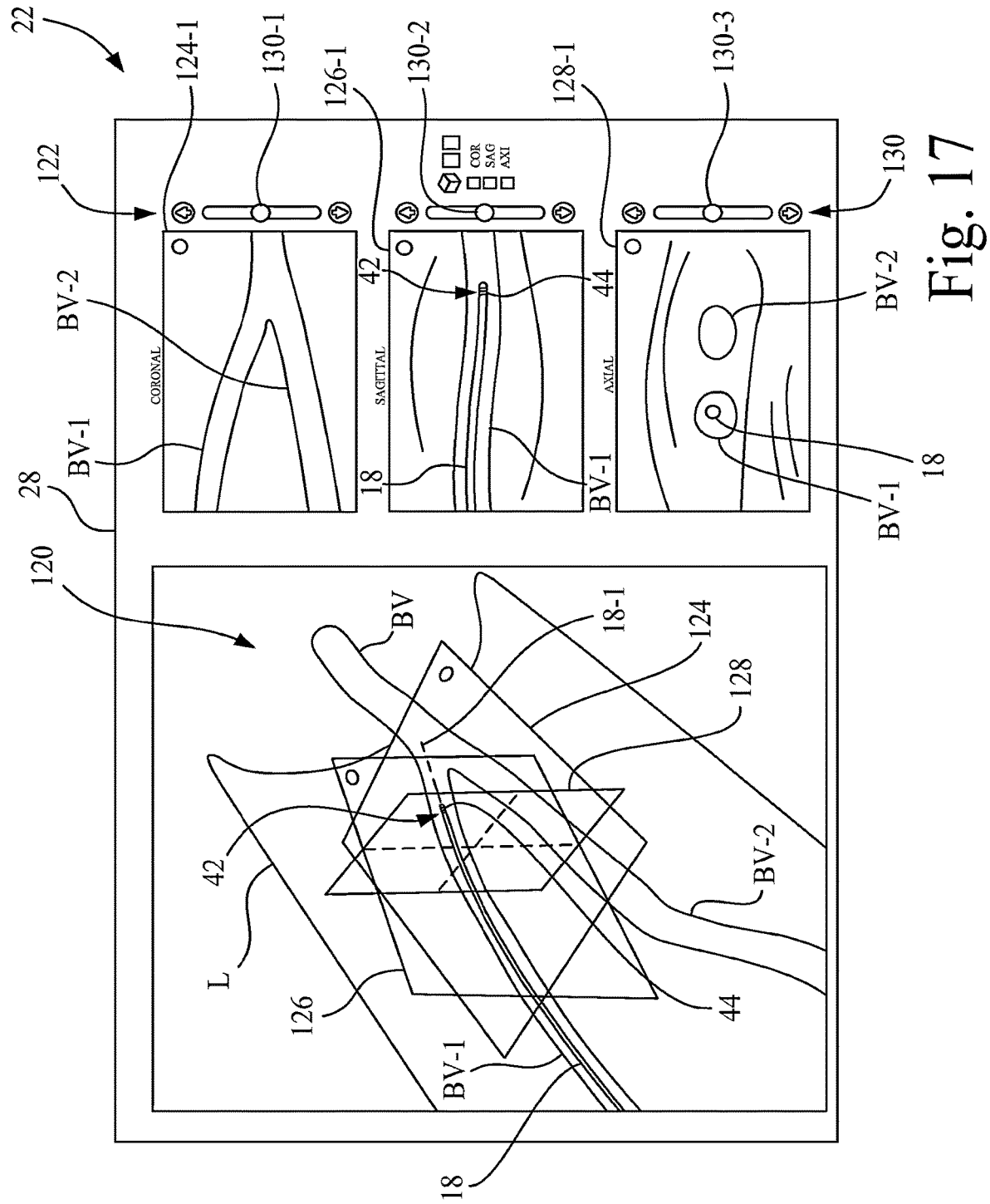
FIG. 17 shows a screen of the graphical user interface of FIG. 1, configured to display one or more synthetic scan planes that are aligned with a longitudinal axis of the interventional medical device.
Figure 18:
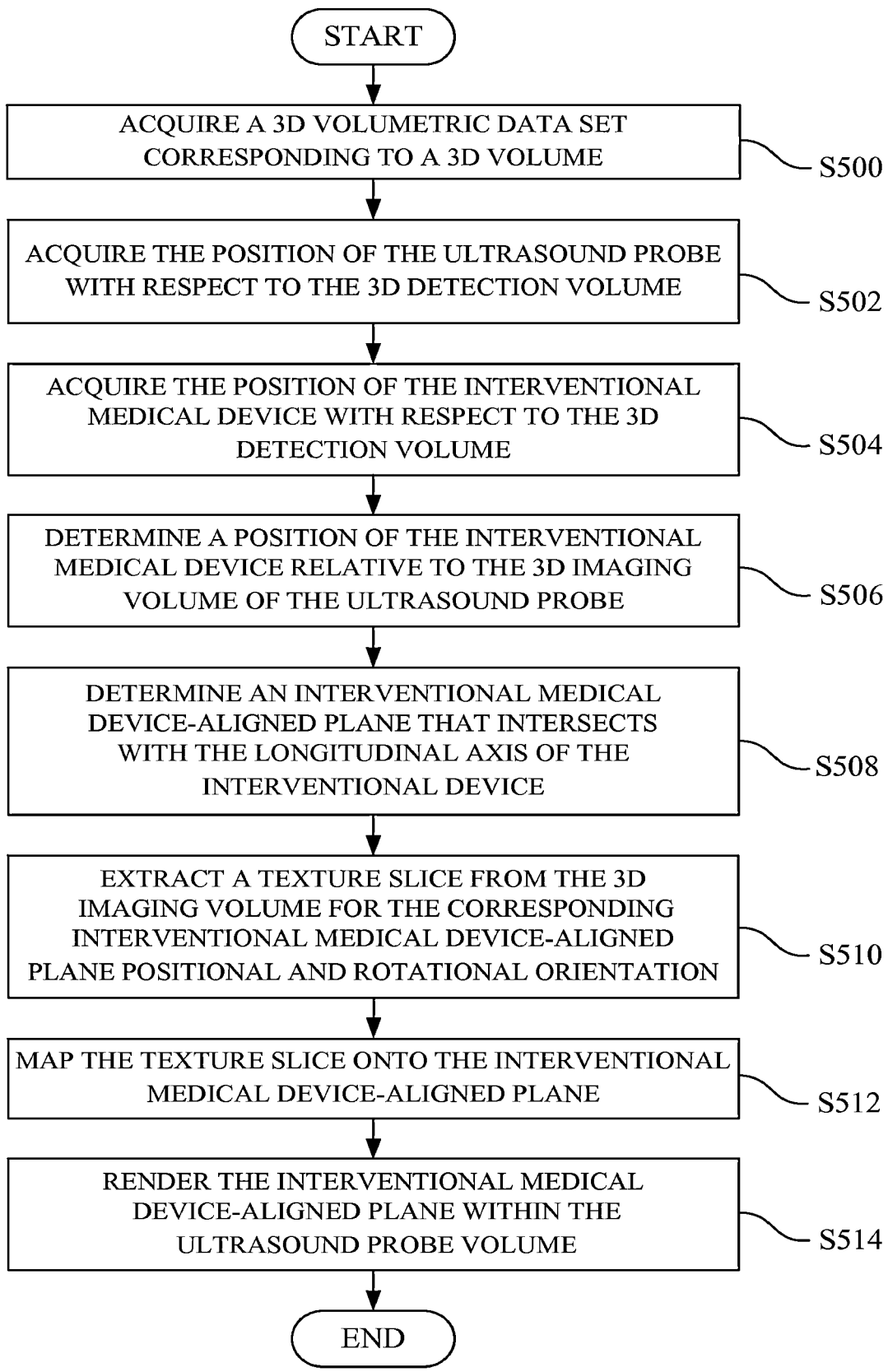
FIG. 18 is a flowchart depicting a method of implementing an interventional medical device aligned mode, associated with the depiction of FIG. 17.

Referring to the embodiment of FIGS. 17 and 18, there is described a method of implementing an interventional medical device aligned mode, wherein ultrasound imaging system 10 is configured to automatically determine, render and display one or more synthetic scan planes that are aligned with a longitudinal axis 18-1 of distal end portion 42 of interventional medical device 18. Axis 18-1 of interventional medical device 18 will be determined based on information relating to the position of tracking element 44 at distal end portion 42 of interventional medical device 18.

Referring to FIG. 17, there is shown the graphical user interface 22 having a three-dimensional (3D) ultrasound image 120 and user controls 122 displayed on display screen 28. 3D ultrasound image 120 includes an image of leg L and blood vessel BV having blood vessel branches BV-1 and BV-2. As described above, a plurality, i.e., a series, of sequential two-dimensional ultrasound slices may be generated and combined to generate 3D ultrasound volumetric data defining a 3D imaging volume.

Using the 3D ultrasound volumetric data acquired from ultrasound probe 16, ultrasound imaging system 10 will execute program instructions to automatically generate synthetic scan planes for rendering and display, such as a coronal plane 124, a sagittal plane 126, and an axial plane 128. Each of coronal plane 124 and sagittal plane 126 has a longitudinal extent corresponding to a direction of the longitudinal extent of axis 18-1 of interventional medical device 18. At least one of coronal plane 124 and sagittal plane 126 will include a lengthwise view of at least the distal end portion 42 of interventional medical device 18 and a lengthwise cross-section of blood vessel BV.

Axial plane 128 is viewed down the length of interventional medical device 18 into axis 18-1. Axial plane 128 may be orthogonal to coronal plane 124 and sagittal plane 126 and may be located to orthogonally intersect interventional medical device 18 so as to depict a transverse cross-section of interventional medical device 18 and blood vessel BV.

In particular, processor circuit 24 of ultrasound imaging system 10 executes program instructions to identify within the 3D ultrasound volumetric data of 3D ultrasound image 120 the image data associated with the desired synthetic plane orientation. The automatically generated synthetic planes may pass through multiple two-dimensional (2D) image data slices in the 3D ultrasound volumetric data. Once the image data associated with the desired synthetic plane orientation within the 3D ultrasound volumetric data is identified, the synthetic scan planes associated with axis 18-1 of distal end portion 42 of interventional medical device 18 may be rendered and displayed on display screen 28 of graphical user interface 22 within the generated 3D ultrasound image 120 as depicted as a coronal view 124-1, sagittal view 126-1, and axial view 128-1 in FIG. 17. The additional views 124-1, 126-1, 128-1 corresponding to the automatically generated synthetic planes may be displayed individually or as a group, and allow for further inspection of the underlying anatomy, beyond what is normally obtained via fluoroscopy, which in turn may result in improved clinical outcomes. It is contemplated that the scan planes may exist in orientations other than at 90 degrees from each other, if desired.

User controls 122 of graphical user interface 22 may include one or more slice selection sliders 130, such as a coronal slider 130-1, a sagittal slider 130-2, and an axial slider 130-3, to provide a sequential variation from an automatically generated two-dimensional synthetic ultrasound image slice(s) being displayed. More particularly, the slice selection sliders 130 are configured to provide a sequential parallel variation, like that discussed above with respect to FIGS. 11-13, from the initially automatically generated two-dimensional ultrasound image slice to manually select a second two-dimensional ultrasound image slice parallel to the initially automatically generated two-dimensional ultrasound image, wherein the second two-dimensional ultrasound image slice lies on either side of the initial synthetically generated two-dimensional ultrasound image slice (plane).

Referring to FIG. 18, there is shown a flowchart describing a method of implementing an interventional medical device aligned mode, associated with the depiction of FIG. 17. Each of the steps, i.e., acts, of the method of FIG. 18 may be implemented as program instructions executed by processor circuit 24.

At step S500, a 3D volumetric data set is acquired that corresponds to the three-dimensional (3D) imaging volume 68 (e.g., a 3D ultrasound probe volume) in the 3D detection volume 38 (see FIGS. 1, 5A and 5B). Recall that a series of sequential two-dimensional ultrasound B-scan imaging slices 67 are generated and combined to generate 3D ultrasound volumetric data defining the three-dimensional imaging volume 68. The acquisition may be performed as in step S100 of FIG. 8, wherein ultrasound imaging system 10 is initialized for rendering a 3D ultrasound image as a set of three orthogonal images, such as setting up processor circuit 24 and graphical user interface 22 for construction of 3D models.

At step S502, the position (e.g., the four axes of freedom, x, y, z, and rotational) of ultrasound probe 16 is acquired with respect to the 3D detection volume 38, i.e., the 3D world space. This may be acquired as in step S106 of FIG. 8, wherein the current position of tracking element 64 of ultrasound probe 16 is determined in relation to the 3D detection volume 38 defined by EM field generator 12 (see also FIG. 1).

At step S504, the position (e.g., the four axes of freedom, x, y, z, and rotational) of interventional medical device 18 is acquired with respect to the 3D detection volume 38, i.e., the 3D world space. This may be acquired as in step S104 of FIG. 8, wherein the current position of tracking element 44 of interventional medical device 18 is determined in relation to the 3D detection volume 38 defined by EM field generator 12 (see also FIG. 1).

Steps S502 and S504 are performed in a continuous loop for generation and updating of the displayed 3D ultrasound image.

At step S506, a position (e.g., the four axes of freedom, x, y, z, and rotational) of interventional medical device 18 is determined relative to the 3D imaging volume 68, i.e., the ultrasound probe volume, of ultrasound probe 16. This may be performed by calculating a world to local transform matrix for the 3D imaging volume 68 with respect to the 3D detection volume 38, then multiplying the local transform matrix by an interventional device transform matrix. The result is the local location of interventional medical device 18 relative to the zero position of the 3D imaging volume 68.

At step S508, an interventional medical device-aligned plane that intersects with the longitudinal axis of the interventional device is determined. The interventional medical device-aligned plane may be, for example, sagittal plane 126 depicted in FIG. 17, from which the coronal and axial plane 128 also may be determined. The interventional medical device-aligned plane may be defined with a normal in the direction of the cross-product of the longitudinal axis 18-1 of interventional medical device 18 and a vertical unit vector. This is described as $\bar{p}=\bar{a}\times\bar{e}_v$, where $\bar{p}$ is the normal to the plane, $\bar{a}$ is the axis 18-1 of interventional medical device 18, and $\bar{e}_v$ is the vertical unit vector of the ultrasound probe volume, e.g., the 3D imaging volume 68. An additional coordinate, d, is required to describe the offset of the interventional medical device-aligned plane relative to the origin of the ultrasound probe volume. The vector describing the plane is then: $a\hat{x}+b\hat{y}+c\hat{z}+d$.

At step S510, a texture slice is extracted from the 3D imaging volume for the corresponding interventional medical device-aligned plane positional and rotational orientation. As used herein, the term "texture slice" is a synthetically generated ultrasound imaging slice that may traverse multiple B-scan imaging slices that define the three-dimensional imaging volume 68. For example, the texture slice extraction may be accomplished by calculating a position and rotation transform for the interventional medical device-aligned plane, normalizing the position and rotation transform, and applying the normalized transform to a 3D Texture, $\bar{y}=M\bar{x}$, where $\bar{y}$ is the transformed 3D texture coordinate vector, M is the transformation matrix, and $\bar{x}$ is the untransformed 3D texture coordinate.

At step S512, the texture slice generated at step S510 is mapped onto the interventional medical device-aligned plane. In other words, the texture coordinates of the texture slice are mapped to the coordinates of the interventional medical device-aligned plane within the ultrasound probe volume, e.g., 3D imaging volume 68.

At step S514, the interventional medical device-aligned plane, e.g., sagittal plane 126, within the ultrasound probe volume, e.g., 3D imaging volume 68, is rendered as the 3D ultrasound image 120 and displayed on display screen 28 of graphical user interface 22, as depicted in FIG. 17. As described above, views of the 3D ultrasound image 120, including interventional medical device 18, with respect to the interventional medical device-aligned synthetic scan planes, such as a coronal plane 124, sagittal plane 126, and an axial plane 128, are automatically generated in the probe volume, e.g., the 3D imaging volume 68, for rendering and display at display screen 28 of graphical user interface 22.

The respective positions, i.e., locations and rotations, of ultrasound probe 16 and interventional medical device 18 relative to the 3D detection volume 38 (see also FIG. 1) may be dynamically and continuously updated by repeating steps S500 through S514.

Thus, in the embodiment of FIGS. 17 and 18, advantageously, ultrasound imaging system 10 automatically generates one or more synthetic scan planes and renders one or more views that contain the intravascular device, i.e., interventional medical device 18. This automatically targeted ultrasound image may assist in the utilization of ultrasound during vascular therapy procedures, such that the use of fluoroscopy is reduced or eliminated.

Figure 19:
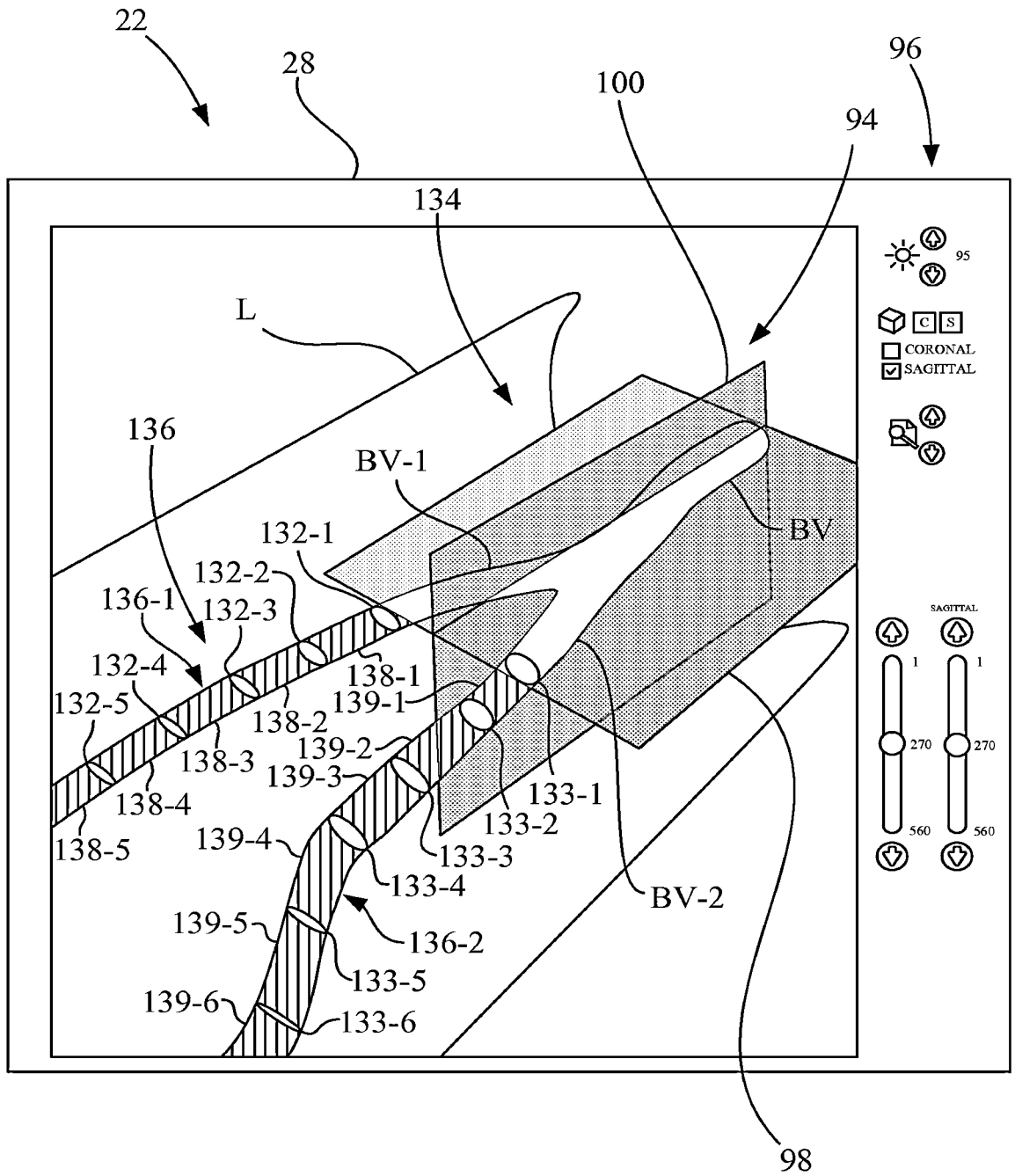
FIG. 19 shows a screen of the graphical user interface of FIG. 1, configured to display a semi-transparent virtual image portion that includes two 3D segmentation models.
Figure 20A:
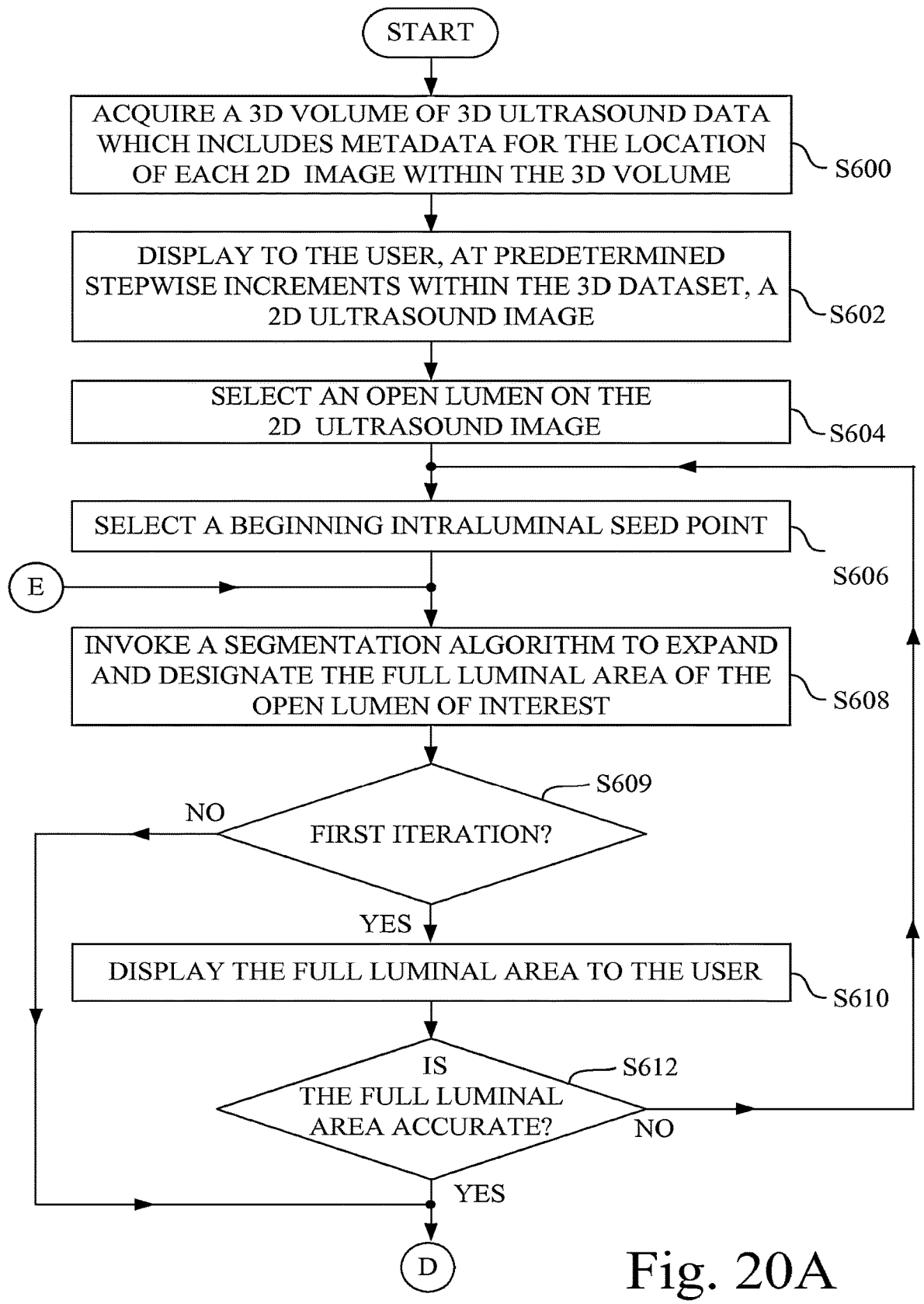
FIGS. 20A and 20B form a flowchart of a segmentation method to achieve 2D virtual image segmentation from which a 3D segmentation model is rendered and displayed, associated with the depiction of FIG. 19, in accordance with an aspect of the present invention.
Figure 20B:
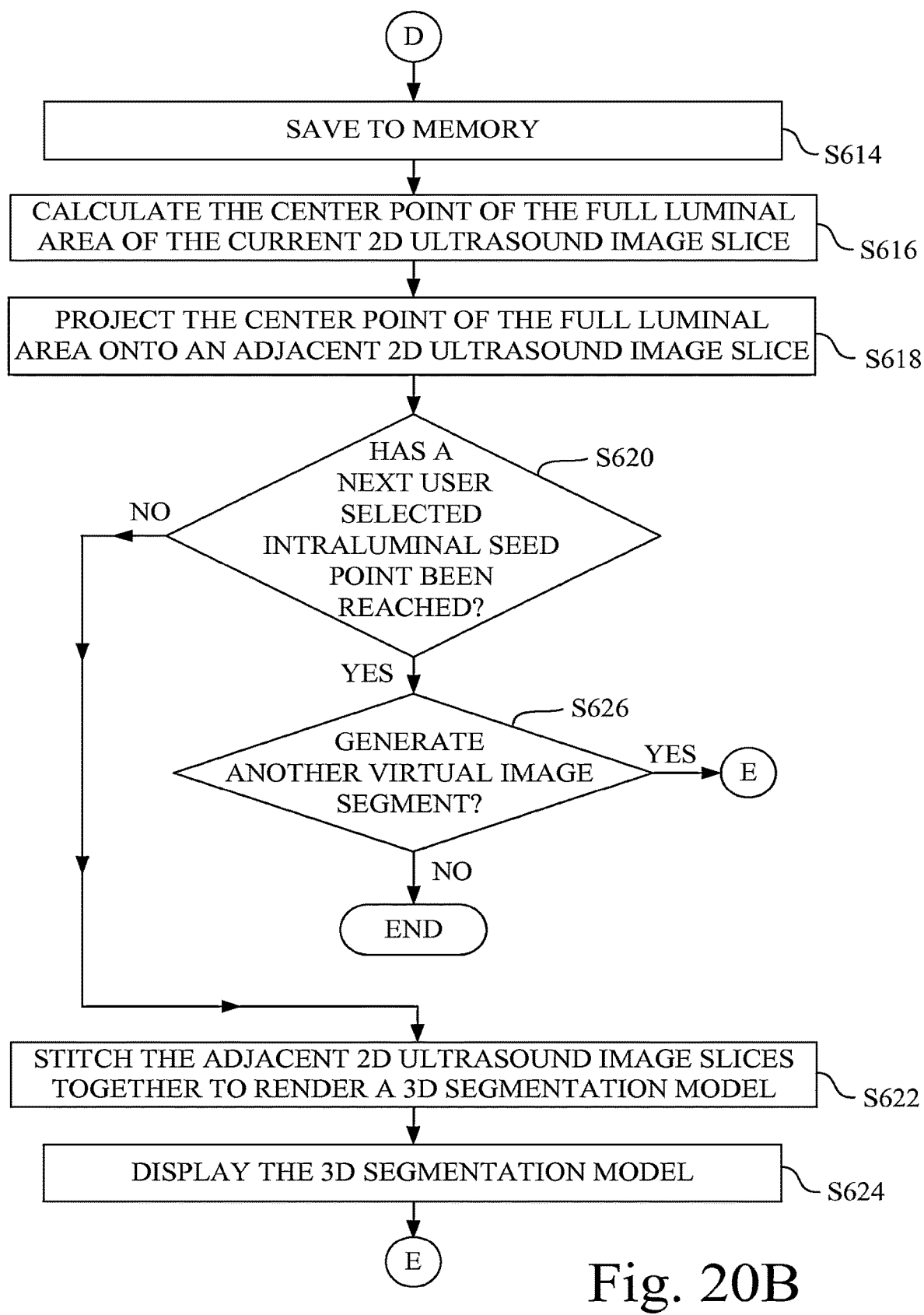

Referring to FIGS. 19, 20A, and 20B, with respect to the embodiments described herein, optionally, a segmentation mode may be provided wherein multiple sets of 3D ultrasound volumetric data corresponding to portions of the detection volume 38 may be generated by ultrasound probe 16 and stored in memory 24-2, as described above. As interventional medical device 18 traverses the vasculature, e.g., blood vessel BV, of the three-dimensional imaging volume 68, the user may operate graphical user interface 22 to store reference locations, i.e., seed points, in memory 24-2 at each of one or more particular regions of interest within the vasculature BV of the three-dimensional imaging volume 68, so as to facilitate a quick and accurate return to a marked location within the vasculature BV within the detection volume 38. In the present embodiment, referring to FIG. 19, the seed points associated with blood vessel branch BV-1 are designated as 132-1, 132-2, 132-3, 132-4 and 132-5, and the seed points associated with blood vessel branch BV-2 are designated as 133-1, 133-2, 133-3, 133-4, 133-5, and 133-6, and are graphically represented on display screen 28 as circular (oval) features representing the edges of the vasculature tubes of blood vessel branches BV-1 and BV-2.

As shown in FIG. 19, the display includes a 3D ultrasound image portion 134 (corresponding to three-dimensional ultrasound image 94) and a virtual image portion 136. Virtual image portion 136 is distinguished from the 3D ultrasound image portion 134 on display screen 28 by an identifying contrast, such a differing color, e.g., red (shown by convention as parallel vertical lines). Advantageously, the virtual image portion 136 depicts the corresponding blood vessel structure without the surrounding tissue structure.

In the present example, virtual image portion 136 includes a 3D segmentation model 136-1 corresponding to blood vessel branch BV-1 and a 3D segmentation model 136-2 corresponding to blood vessel branch BV-2. As such, in the example of FIG. 19, 3D segmentation model 136-1 is rendered from a plurality of connected virtual image segments individually identified as virtual image segments 138-1, 138-2, 138-3, 138-4, and 138-5. 3D segmentation model 136-2 is rendered from a plurality of connected virtual image segments individually identified as virtual image segments 139-1, 139-2, 139-3, 139-4, 139-5 and 139-6. As used herein, the term "virtual image segment" means an extrapolated portion that extends from a reference point to an end point, such as between a pair of adjacent seed points, or within a range of a predetermined number of consecutive 2D ultrasound images, e.g., a range that includes 30 consecutive 2D ultrasound images.

For example, as shown in the example of FIG. 19, virtual image segment 138-1 lies between seed points 132-1 and 132-2, virtual image segment 138-2 lies between seed points 132-2 and 132-3, etc. Likewise, virtual image segment 139-1 lies between seed points 133-1 and 133-2, virtual image segment 139-2 lies between seed points 133-2 and 133-3, etc.

Thus, as shown in FIG. 19, and in accordance with the present aspect of the invention, a 3D rendering of the underlying vasculature may be extracted from a set of 2D ultrasound, e.g., B-mode, images acquired by the ultrasound probe 16, and a virtual representation of the 3D vasculature may be displayed along with other 2D display data on display screen 28. This virtual representation thus serves as a 3D virtual map of the vasculature to further orient the user as to the location of vessels, bifurcations, and other adjacent anatomy that is not displayed via a particular 2D ultrasound slice.

FIGS. 20A and 20B form a flowchart of a segmentation method to achieve 2D virtual image segmentation that may be used to implement the segmentation mode in the generation of a 3D segmentation model as a virtual representation of the vasculature in accordance with an aspect of the present invention. Each of the steps, i.e., acts, of the method of FIGS. 20A and 20B may be implemented as program instructions executed by processor circuit 24, unless otherwise indicated.

At step S600, a 3D volume of 3D ultrasound data which includes metadata for the location of each 2D ultrasound image, i.e., slice, within the 3D volume is acquired via a scanning of ultrasound probe 16 to form a 3D dataset.

At step S602, at predetermined stepwise increments within the 3D dataset, a 2D ultrasound image is displayed to the user on display screen 28, from which the user can select an open lumen of interest of the vasculature, as a basis for segmentation. As a secondary method, the presence of Doppler flow within a candidate lumen of the vasculature may be used to select an area on the image for designation as an intraluminal space.

At step S604, the user selects an open lumen of interest of the vasculature on the displayed 2D ultrasound image. The user selection of the open lumen may be accomplished via graphical user interface 22, e.g., via touch screen display 26, via a cursor on display screen 28, or other method used to indicate a location on the displayed 2D ultrasound image.

At step S606, the user selects a beginning point, e.g., a previously stored intraluminal seed point, associated with vasculature, e.g., BV-1, as a point to begin the virtual image segmentation. The beginning seed point may be, for example, seed point 132-1 of the prior user defined seed points (see FIG. 19). The user selection may be accomplished via graphical user interface 22, e.g., via touch screen display 26, via a cursor on display screen 28, etc.

At step S608, a segmentation algorithm, such as an edge detection algorithm, is invoked to further expand and designate the full luminal area of the open lumen of interest of a current 2D ultrasound image slice. In the initial pass, the segmentation algorithm will be invoked with respect to the beginning seed point of the current 2D ultrasound image slice. Thereafter, the segmentation algorithm will be invoked with respect to the selected open lumen of the next adjacent 2D ultrasound image slice.

At step S609, it is determined whether this is the first iteration from the current seed point. If NO, then the process proceeds to step S614.

However, if the determination at step S609 is YES, then the process proceeds to step S610.

At step S610, the full luminal area of the open lumen of interest of the current 2D ultrasound image is then displayed to the user at display screen 28.

At step S612, if the user designates, at graphical user interface 22, that the full luminal area of the open lumen of interest being displayed is not accurate (decision is NO), then the process returns to step S606 to re-select a beginning seed point, or alternatively, the process may end.

At step S612, if the user designates, at graphical user interface 22, that the full luminal area of the open lumen of interest being displayed is accurate (decision is YES), then the process proceeds to step S614.

At step S614, the data associated with the full luminal area of the open lumen is saved to memory 24-2.

At step S616, a center point of the full luminal area of the current 2D ultrasound image slice is then calculated, such as by using a 2d mean squared calculation.

At step S618, the center point is then projected onto an adjacent 2D ultrasound image slice of the set of 2D ultrasound images. In the present context, the term "adjacent" refers to two 2D ultrasound images that are sequentially next to one another.

At step S620, it is determined whether the next user selected seed point, e.g., seed point 132-2 as approached from seed point 132-1 (see FIG. 19), has been reached.

If the result at S620 is NO, then the process proceeds to step S622.

At step S622, the adjacent 2D ultrasound image slices are then joined, i.e., stitched together, to render a semi-transparent 3D segmentation model, e.g., at this stage, a portion of the 3D segmentation model 136-1 depicted in FIG. 19.

At step S624, the current rendering of the 3D segmentation model is persistently displayed within a 3D scene graph on display screen 28, as shown in FIG. 19. The process then returns to step S608, and steps S608-S118 are repeated.

If the result at step S620 is YES, i.e., that the next seed point, e.g., seed point 132-2 (see FIG. 19), has been reached, then the current virtual image segment, e.g., virtual image segment 138-1, has been completed, and the process proceeds to step S626.

At step S626, it is determined whether it is desired to generate another virtual image segment. Step S626 may be a user intervention point in the process, wherein the process waits on a user entered determination at graphical user interface 22, or alternatively, may be a decision made by the program logic based on a predetermined selection made by the user at graphical user interface 22 (e.g., the user selects a quantity of virtual image segments that will form the 3D segmentation model.

If the determination is YES, then the process returns to step S608 to start assembling the next virtual image segment, e.g., virtual image segment 138-2, for rendering as the 3D segmentation model, which is dynamically expanding at each iteration of the process, and which may continue until the entirety of the 3D segmentation model 136-1 depicted in FIG. 19 is complete.

However, if the determination at step S626 is NO, then the desired segmentation and dynamic formation of the 3D segmentation model is complete, and the process ends. It is to be understood, however, that the process described above may be repeated to render and display the 3D segmentation model 136-2 also depicted in FIG. 19.

Thus, based on the above, it is to be understood that each 3D segmentation model may be made up of at least one virtual image segment, e.g., virtual image segment 138-1, and may include a plurality of virtual image segments, e.g., virtual image segments 138-1, 138-2, 138-3, 138-4, etc.

Also, if desired, 2D ultrasound images, i.e., image slices, that bisect the vasculature may also be rendered and displayed to the user within this 3D user environment. Further, additional ultrasound planes such as the coronal plane, may be rendered and displayed to the user.

As a further alternative, rather than using sequential seed points as the beginning and ending points of a virtual image segment, it is to be understood that the process described above may designate the number of 2D ultrasound image slices, e.g., 25-50 slices, that are to constitute a virtual image segment, and the process described above is repeated for the selected number of 2D ultrasound image slices.

In each of the embodiments described above, the slice selection/localization is performed based on magnetic tracking. However, it is contemplated that other tracking methods may be used in accordance with the present invention.

Figure 21:
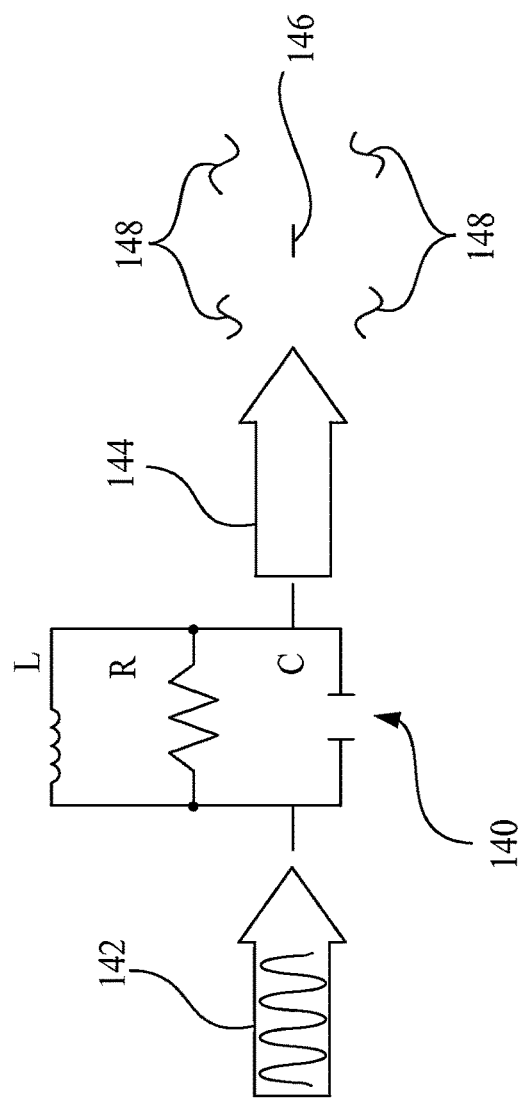
FIG. 21 is a diagrammatic depiction of Doppler image localization utilized in ultrasound image slice selection/localization, in accordance with another embodiment of the present invention.

For example, referring to FIG. 21, in another implementation, Doppler image localization may be utilized in ultrasound image slice selection/localization. FIG. 21 depicts an LRC tissue model 140 that represents tissue as an inductor (L), resistor (R), capacitor (C) circuit which receives a high frequency source signal 142, in a frequency range of 19 k Hertz to 2M Hertz. In this embodiment, the system detects the Doppler frequency shift that is created in the ultrasound return signal 144 due to fluid motion (e.g., blood) or due to the motion of the surrounding tissues that resonate, such as for example, as a result of the Bard Crosser® Catheter treatment frequency of 20.5 k Hertz. The ultrasound return signal 144 will not only include high frequency waves 146, but will also include scattered lower frequency waves 148. Although the Crosser Catheter resonates at a higher frequency than can normally be detected via Doppler, it is believed that the surrounding tissues create a dampening and superposition effect on the propagating waves, which creates lower frequency waves 148 that register as a Doppler shift via ultrasound. This Doppler signal may be detected and used to display only the relevant slice that contains the Doppler motion.

In accordance with the above, a method of using an ultrasound imaging system having an ultrasound probe 16 and a display screen 28 for imaging a region of interest in a patient, includes the steps of operating ultrasound probe 16 to generate a 3D image volume from a plurality of individual 2D ultrasound image slices; detecting a Doppler shift that is created in an ultrasound return signal due to motion of surrounding tissues that resonate as a result of a vibration source positioned inside the patient (e.g., such as a Bard Crosser Catheter treatment frequency); selecting a 2D ultrasound image slice, of plurality of individual 2D ultrasound image slices, that contains the Doppler shift, the selected 2D ultrasound image slice providing a visualization of the vibration source and the surrounding tissues; and displaying the selected 2D ultrasound image slice on the display screen 28. Each of the steps may be implemented as program instructions executed by processor circuit 24.

Figure 22:
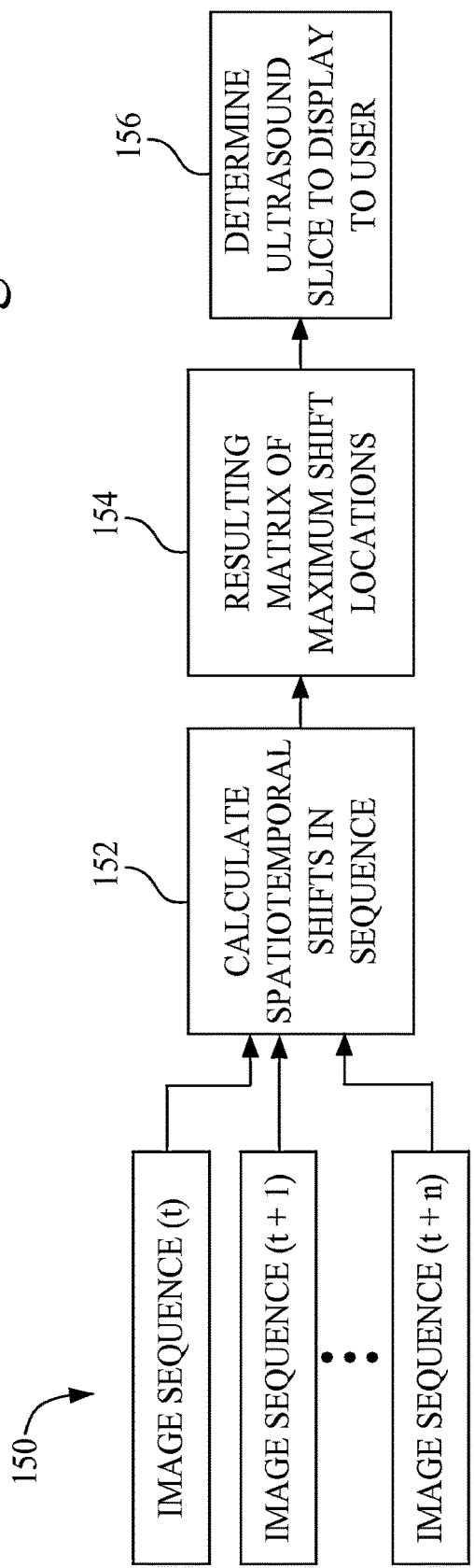
FIG. 22 is a block diagram depiction of a method of motion image localization utilized in ultrasound image slice selection/localization, in accordance with another embodiment of the present invention.

Referring to FIG. 22, in another implementation, motion image localization may be utilized in ultrasound 2D ultrasound image slice selection/localization, utilizing a comparison of multiple sets of 3D ultrasound datasets 150 represented in FIG. 22 as image sequence (t), image sequence (t+1), . . . image sequence (t+n), wherein t is time and n is the last time offset in the sequence. Because the ultrasound system can acquire a sequence of 3D ultrasound datasets 150 from a fixed location over the skin, the 3D ultrasound datasets 150 can be compared at block 152 in a spatiotemporal domain, and filtered for motion using any of a number of motion detection algorithm calculations that incorporate spatiotemporal shifts, or local amplitude variation. The result of the calculation at block 154 is a matrix of maximum shift locations. At block 156, the matrix of maximum shift locations are be used to compute a motion likelihood indicator for the dataset, which is associated with an (x, y, z) coordinate under the ultrasound sensor. This coordinate, once converged upon, can subsequently be used to select the relevant 2D ultrasound image slice that contains this coordinate. The motion image localization may also incorporate last known location seeding to speed up the motion detection.

In accordance with the above, a method of using an ultrasound imaging system having ultrasound probe 16 and display screen 28 for imaging a region of interest in a patient, includes the steps of: operating the ultrasound probe 16 to acquire a sequence of 3D data sets from a fixed location relative to the patient, each 3D data set representing the same 3D image volume, the 3D image volume being formed from a plurality of individual 2D ultrasound image slices; processing the sequence of 3D data sets in a spatiotemporal domain using a motion filter algorithm to identify Cartesian coordinates of a location of motion within the 3D image volume; selecting a 2D ultrasound image slice, of plurality of individual 2D ultrasound image slices, that contains the Cartesian coordinates of the location of motion; and displaying the selected 2D ultrasound image slice on the display screen. Each of the steps may be implemented as program instructions executed by processor circuit 24.

In the embodiments set forth above, ultrasound scanning was performed using ultrasound probe 16 having a single transducer array. However, referring to FIGS. 23 and 24, as an alternative to a single transducer scanning mechanism, and in accordance with another aspect to the present invention, there is provided an ultrasound probe 160 configured with multiple electromechanically scanned one-dimensional, e.g., linear, ultrasound transducer arrays. It is contemplated that ultrasound probe 160 may be a substitute for ultrasound probe 16 in the embodiments described above.

Figure 23:
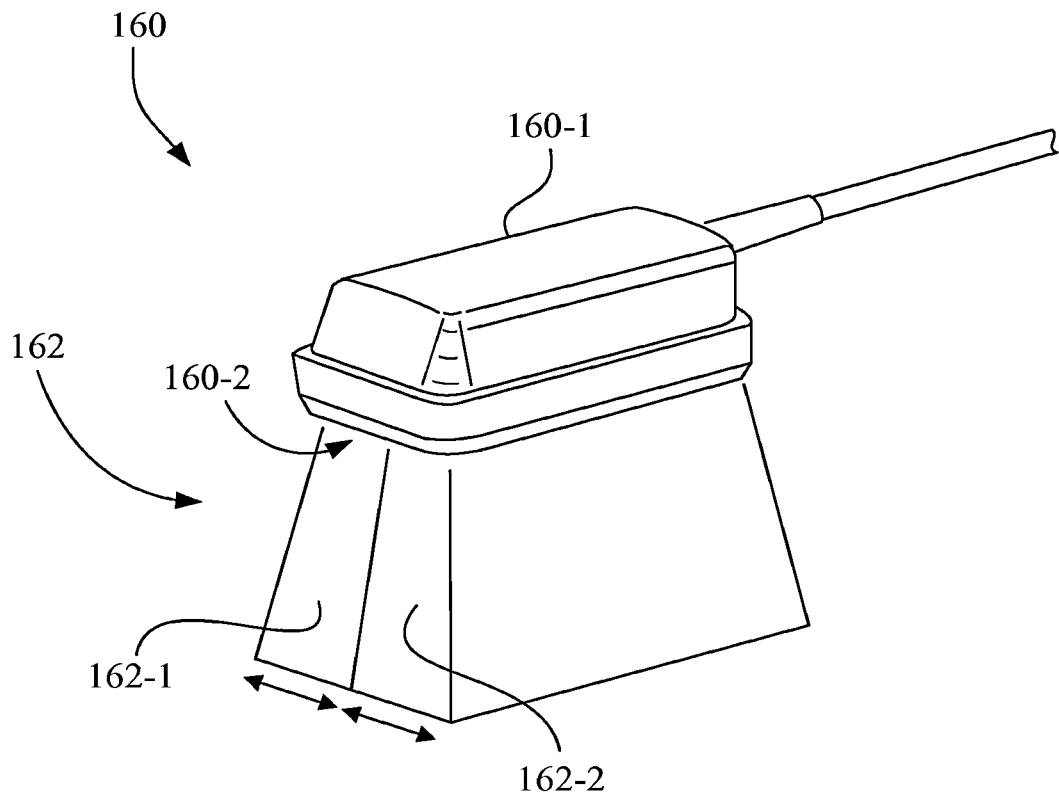
FIG. 23 depicts an ultrasound probe having multiple electromechanically scanned one-dimensional ultrasound transducer arrays, in accordance with another aspect of the present invention.
Figure 24:
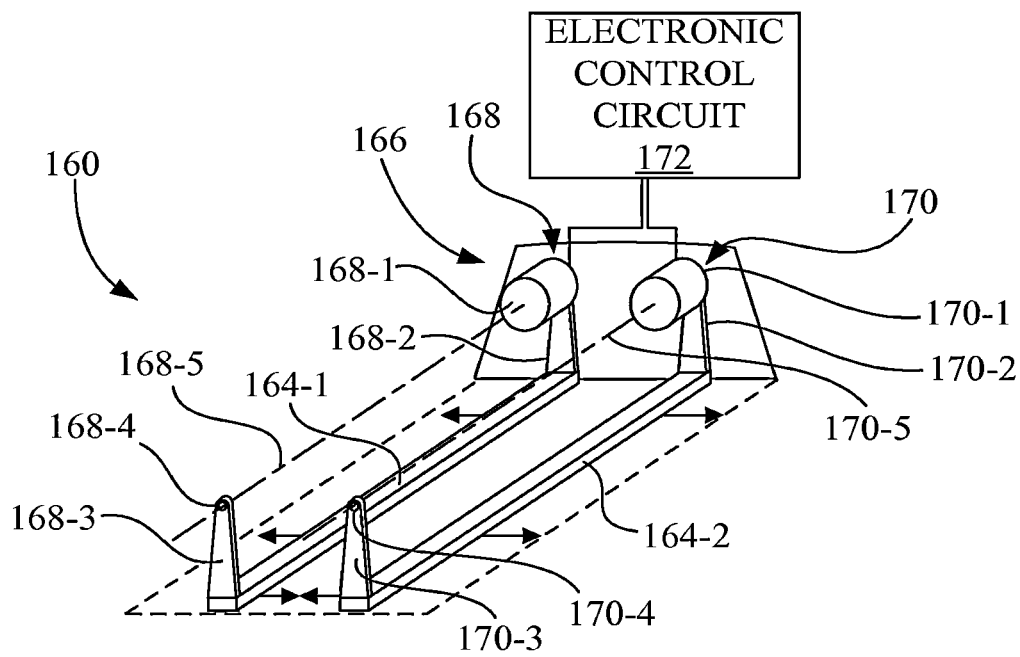
FIG. 24 is a diagrammatic depiction of the electromechanical scanning mechanism of FIG. 23.

Referring to FIGS. 23 and 24, ultrasound probe 160 is configured to define a 3D imaging volume 162. Ultrasound probe 160 includes a housing 160-1 and a scanning aperture 160-2. The 3D imaging data associated with 3D imaging volume 162 is acquired using multiple, e.g., two, electromechanically scanned one-dimensional ultrasound transducer arrays, individually identified as one-dimensional ultrasound transducer array 164-1 and one-dimensional ultrasound transducer array 164-2 housed in housing 160-1.

In the present embodiment, of the entire 3D imaging volume 162, a sweeping range of one-dimensional ultrasound transducer array 164-1 will define a first 3D imaging volume portion 162-1 and a sweeping range of one-dimensional ultrasound transducer array 164-2 will define a second 3D imaging volume portion 162-2. Each of one-dimensional ultrasound transducer array 164-1 and one-dimensional ultrasound transducer array 164-2 may be configured as described above with respect to one-dimensional ultrasound transducer array 70 depicted in FIG. 6B, discussed above.

In the configuration depicted in FIG. 24, one-dimensional ultrasound transducer array 164-1 and one-dimensional ultrasound transducer array 164-2 are independent and parallel linear ultrasound transducer arrays, which may be electromechanically scanned individually or simultaneously using an electromechanical drive unit 166. Electromechanical drive unit 166 includes two dedicated electromechanical drives 168, 170 electrically coupled to an electronic control circuit 172 via a wired cable connection.

Electromechanical drive 168 includes a motor 168-1 electrically and communicatively coupled to electronic control circuit 172. Motor 168-1, such as a stepper motor, has a shaft coupled to a proximal end of a cantilever arm 168-2. A distal end of cantilever arm 168-2 is connected to one end of one-dimensional ultrasound transducer array 164-1. A distal end of a second cantilever arm 168-3 is connected an opposite end of one-dimensional ultrasound transducer array 164-1. A proximal end of cantilever arm 168-3 is rotatably coupled to a pivot pin 168-4. Pivot pin 168-4 is axially aligned with the shaft of motor 168-1 on a pivot axis 168-5.

Electromechanical drive 170 includes a motor 170-1 electrically and communicatively coupled to electronic control circuit 172. Motor 170-1, such as a stepper motor, has a shaft coupled to a proximal end of a cantilever arm 170-2. A distal end of cantilever arm 170-2 is connected to one end of one-dimensional ultrasound transducer array 164-2. A distal end of a second cantilever arm 170-3 is connected to an opposite end of one-dimensional ultrasound transducer array 164-2. A proximal end of cantilever arm 170-3 is rotatably coupled to a pivot pin 170-4. Pivot pin 170-4 is axially aligned with the shaft of motor 170-1 on a pivot axis 170-5.

One or both of one-dimensional ultrasound transducer array 164-1 and one-dimensional ultrasound transducer array 164-2 may be electromechanically swept from side to side by the respective electromechanical drive 168, 170 in order to acquire a 3D dataset corresponding to the 3D imaging volume 162 shown in FIG. 23. Moreover, the drive range of each of electromechanical drives 168, 170 is adjustable, e.g., by changing the amount of shaft rotation and rotational orientation of the respective motor 168-1, 170-1, to provide a desired 3D sweep area to produce a desired 3D ultrasound data set. Each of one-dimensional ultrasound transducer array 164-1 and one-dimensional ultrasound transducer array 164-2 is configured longitudinally, so paging motion is reduced and ultrasound probe 160 can automatically produce a sagittal slice of a vessel oriented under the probe and running the length of ultrasound probe 160.

Referring to FIGS. 25A, 25B, 26A, 26B, ultrasound probe 160 is configured to produce multiple sweep patterns when acquiring a 3D dataset. Large sweeping patterns can acquire a 3D dataset covering an entire area beneath the ultrasound probe, and can be used for general scanning.

Figures 25A, 25B:
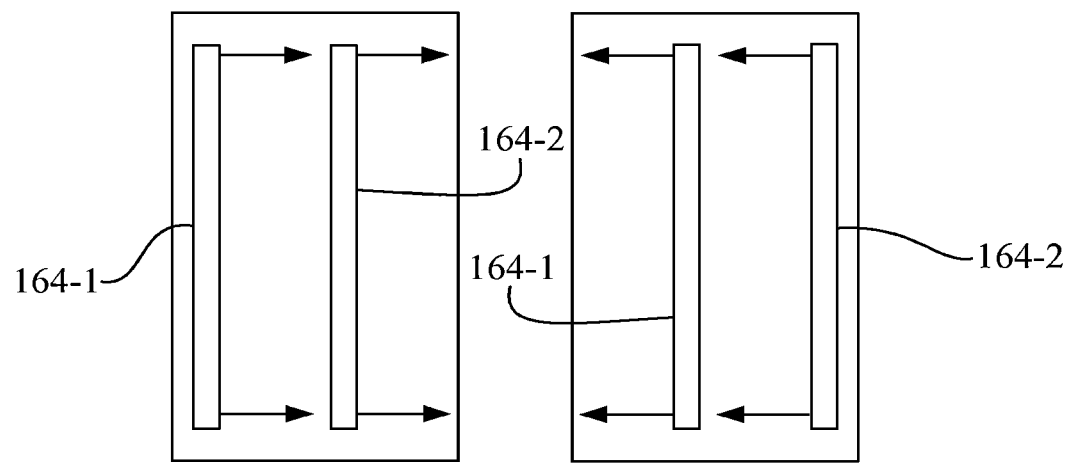
FIG. 25A depicts an exemplary sweeping pattern of the two one-dimensional ultrasound transducer arrays of FIGS. 23 and 24 to acquire a 3D dataset covering the entire area beneath the ultrasound probe, wherein each of the two one-dimensional ultrasound transducer arrays are swept in the same direction left-to-right.
FIG. 25B depicts an exemplary sweeping pattern of the two one-dimensional ultrasound transducer arrays of FIGS. 23 and 24 to acquire a 3D dataset covering the entire area beneath the ultrasound probe, wherein each of the two one-dimensional ultrasound transducer arrays are swept in the same direction right-to-left.

For example, FIG. 25A depicts an exemplary sweeping pattern of the two one-dimensional ultrasound transducer arrays 164-1, 164-2 to acquire a 3D dataset covering the entire area beneath the ultrasound probe 160, wherein both of one-dimensional ultrasound transducer array 164-1 and one-dimensional ultrasound transducer array 164-2 are swept in the same direction left-to-right. Similarly, FIG. 25B depicts an exemplary sweeping pattern of the two one-dimensional ultrasound transducer arrays 164-1, 164-2 to acquire a 3D dataset covering the entire area beneath ultrasound probe 160, wherein both of one-dimensional ultrasound transducer array 164-1 and one-dimensional ultrasound transducer array 164-2 are swept in the same direction right-to-left, which may be the return sweep of that depicted in FIG. 25A.

Figures 26A, 26B:
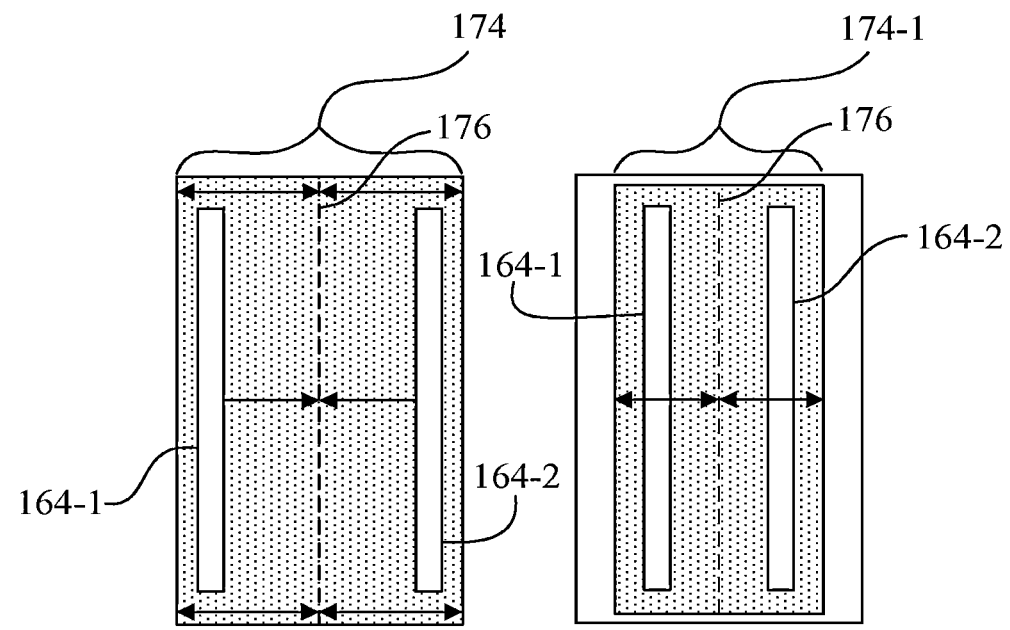
FIG. 26A depicts a sweeping pattern to acquire a 3D dataset covering the entire area beneath the ultrasound probe of FIGS. 23 and 24, wherein the two one-dimensional ultrasound transducer arrays are swept in opposite directions.
FIG. 26B depicts a sweeping pattern to acquire a 3D dataset covering only a portion of the entire area beneath the ultrasound probe depicted in FIG. 26A, thereby providing a reduction of the sweeping pattern, or aperture, of the ultrasound probe of FIGS. 23 and 24.

FIG. 26A depicts a sweeping pattern to acquire a 3D dataset covering the entire area 174 beneath ultrasound probe 160, wherein one-dimensional ultrasound transducer array 164-1 and one-dimensional ultrasound transducer array 164-2 are swept in opposite directions. Once a preferred location has been defined, e.g., as depicted by the dashed line 176, the sweeping pattern or aperture can be reduced. For example, FIG. 26B depicts a sweeping pattern of one-dimensional ultrasound transducer array 164-1 and one-dimensional ultrasound transducer array 164-2 to acquire a 3D dataset covering only a portion 174-1 of the entire area 174 beneath ultrasound probe 160, thereby providing a reduction of the sweeping pattern or aperture of ultrasound probe 160.

In accordance with the above, ultrasound probe 160 includes a housing 160-1 containing a first one-dimensional ultrasound transducer array 164-1 and a second one-dimensional ultrasound transducer array 164-2. The first one-dimensional ultrasound transducer array 164-1 has a first longitudinal extent in a first direction, i.e., parallel to pivot axes 168-5, 170-5. The second one-dimensional ultrasound transducer array 164-2 has a second longitudinal extent in the first direction. The second one-dimensional ultrasound transducer array 164-2 is arranged parallel to the first one-dimensional ultrasound transducer array 164-1. A first electromechanical drive 168 is configured to move the first one-dimensional ultrasound transducer array 164-1 in a transverse direction perpendicular to the first direction 168-5, 170-5 to define a first adjustable sweep pattern. A second electromechanical drive 170 is configured to move the second one-dimensional ultrasound transducer array 164-2 in a transverse direction perpendicular to the first direction 168-5, 170-5 to define a second adjustable sweep pattern. Each of the first electromechanical drive 168 and the second electromechanical drive 170 is configured for independent operation. Each of the first electromechanical drive 168, the first one-dimensional ultrasound transducer array 164-1, the second electromechanical drive 170, and the second one-dimensional ultrasound transducer array 164-2 is contained within housing 160-1. The electronic control circuit 172 is electrically coupled to the first electromechanical drive 168 and to the second electromechanical drive 170.

Electronic control circuit 172 is configured with a processor and associated circuitry, such as processor circuit 24, to provide first control signals to each of the first electromechanical drive 168 and the second electromechanical drive 170 to generate a first composite sweep pattern of the first one-dimensional ultrasound transducer array 164-1 and the second one-dimensional ultrasound transducer array 164-2 as a combination of the first adjustable sweep pattern and the second adjustable sweep pattern. The first composite sweep pattern has a first composite sweep area in which the first one-dimensional ultrasound transducer array 164-1 and the second one-dimensional ultrasound transducer array 164-2 generate a first 3-D ultrasound data set.

Electronic control circuit 172 may include a selection device, as described above, configured to select a desired 2-D slice location within the first 3-D ultrasound data set. Alternatively, the selection device may be incorporated into the controls of ultrasound console 14.

Electronic control circuit 172 is configured to provide second control signals, representative of the desired 2-D slice location, to each of the first electromechanical drive 168 and second electromechanical drive 170 to modify a sweeping range of each of the first adjustable sweep pattern and the second adjustable sweep pattern to generate a second composite sweep pattern. The second composite sweep pattern has a second composite sweep area in which the first one-dimensional ultrasound transducer array 164-1 and the second one-dimensional ultrasound transducer array 164-2 generate a second 3-D ultrasound data set. The second composite sweep area is smaller than the first composite sweep area and the second 3-D ultrasound data set contains less data than the first 3-D ultrasound data set while including the desired 2-D slice location.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for generation of a virtual representation of a vasculature, comprising:
   acquiring a 3D volume of 3D ultrasound data which includes metadata for a location of each 2D ultrasound image within the 3D volume to form a 3D data set;
   displaying, at predetermined stepwise increments within the 3D dataset, a 2D ultrasound image to a user;
   selecting an open lumen of interest of the vasculature on the displayed 2D ultrasound image;
   selecting a beginning point in the selected open lumen of interest of the vasculature;
   invoking a segmentation algorithm to expand and designate a full luminal area of the open lumen of interest of a current 2D ultrasound image slice;
   displaying the full luminal area of the open lumen of interest of the current 2D ultrasound image slice to the user for evaluation;
   saving data associated with the full luminal area;
   calculating a center point of full luminal area;
   projecting the center point associated with the current 2D image slice onto an adjacent 2D ultrasound image slice; and
   repeating the steps of invoking, saving, calculating and projecting until an ending point has been reached, at which time a first 2D virtual image segment has been generated.

2. The method according to claim 1, further comprising prior to the act of repeating:
   stitching the adjacent 2D ultrasound image slices together to form a 3D segmentation model; and
   displaying the 3D segmentation model on a display screen.

3. The method according to claim 1, wherein each of the beginning point and the ending point is a predetermined seed point of a plurality of predetermined seed points.

4. The method according to claim 1, wherein the beginning point and the ending point is a numerical range of 2D ultrasound image slices.

5. The method according claim 1, wherein each of the acts of the method is implemented as program instructions executed by a processor circuit.

* * * * *

UNITED STATES PATENT AND TRADEMARK OFFICE
CERTIFICATE OF CORRECTION

PATENT NO. : 12,274,581 B2
APPLICATION NO. : 18/323130
DATED : April 15, 2025
INVENTOR(S) : Jeremy B. Cox et al.

Page 1 of 1

It is certified that error appears in the above-identified patent and that said Letters Patent is hereby corrected as shown below:

In the Claims

In Column 34, Line(s) 56, Claim 5, after "according", insert --to--.

Signed and Sealed this
Twenty-seventh Day of May, 2025

Coke Morgan Stewart
*Acting Director of the United States Patent and Trademark Office*